US012703759B2

(12) United States Patent
Fan et al.

(10) Patent No.: US 12,703,759 B2
(45) Date of Patent: Aug. 11, 2026

(54) CD19 BINDING MOLECULES AND USES THEREOF

(71) Applicant: Legend Biotech USA Inc., Somerset, NJ (US)

(72) Inventors: Xiaohu Fan, Edmonton (CA); Zhe Zhou, Nanjing (CN); Qiuchuan Zhuang, Nanjing (CN); Xu Fang, Nanjing (CN); Yue Han, Nanjing (CN); Youguo Peng, Nanjing (CN); Manman Lu, Nanjing (CN)

(73) Assignee: Legend Biotech USA Inc., Somerset, NJ (US)

( * ) Notice: Subject to any disclaimer, the term of this patent is extended or adjusted under 35 U.S.C. 154(b) by 794 days.

(21) Appl. No.: 18/015,508

(22) PCT Filed: Jul. 16, 2021

(86) PCT No.: PCT/CN2021/106892

§ 371 (c)(1),
(2) Date: Jan. 10, 2023

(87) PCT Pub. No.: WO2022/012683

PCT Pub. Date: Jan. 20, 2022

(65) Prior Publication Data

US 2023/0192883 A1 Jun. 22, 2023

(30) Foreign Application Priority Data

Jul. 16, 2020 (WO) ................ PCT/CN2020/102457

(51) Int. Cl.

| | |
|---|---|
| ***C07K 16/28*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C12N 5/0783*** | (2010.01) |
| ***C12N 15/63*** | (2006.01) |

(52) U.S. Cl.

CPC .......... *C07K 16/2896* (2013.01); *A61K 40/11* (2025.01); *A61K 40/31* (2025.01); *A61K 40/4211* (2025.01); *A61P 35/00* (2018.01); *C12N 5/0636* (2013.01); *C12N 15/63* (2013.01); *A61K 2239/31* (2023.05); *A61K 2239/38* (2023.05); *A61K 2239/48* (2023.05); *C07K 2317/20* (2013.01); *C07K 2317/565* (2013.01); *C07K 2317/567* (2013.01); *C07K 2319/02* (2013.01); *C07K 2319/03* (2013.01)

(58) Field of Classification Search

None

See application file for complete search history.

(56) References Cited

U.S. PATENT DOCUMENTS

| | | | |
|---|---|---|---|
| 30,985 | A | 12/1860 | Pye |
| 4,179,337 | A | 12/1979 | Davis et al. |
| 4,301,144 | A | 11/1981 | Iwashita et al. |
| RE30,985 | E | 6/1982 | Cartaya |
| 4,496,689 | A | 1/1985 | Mitra |
| 4,526,938 | A | 7/1985 | Churchill et al. |
| 4,560,655 | A | 12/1985 | Baker |
| 4,640,835 | A | 2/1987 | Shimizu et al. |
| 4,657,760 | A | 4/1987 | Kung et al. |
| 4,657,866 | A | 4/1987 | Kumar |
| 4,670,417 | A | 6/1987 | Iwashita et al. |
| 4,690,915 | A | 9/1987 | Rosenberg |
| 4,767,704 | A | 8/1988 | Cleveland et al. |
| 4,791,192 | A | 12/1988 | Nakagawa et al. |
| 4,816,567 | A | 3/1989 | Cabilly et al. |
| 4,927,762 | A | 5/1990 | Darfler |
| 5,112,946 | A | 5/1992 | Maione |
| 5,122,469 | A | 6/1992 | Mather et al. |
| 5,128,326 | A | 7/1992 | Balazs et al. |
| 5,206,344 | A | 4/1993 | Katre et al. |
| 5,208,020 | A | 5/1993 | Chari et al. |
| 5,225,212 | A | 7/1993 | Martin et al. |
| 5,225,539 | A | 7/1993 | Winter |
| 5,264,365 | A | 11/1993 | Georgiou et al. |
| 5,336,603 | A | 8/1994 | Capon et al. |
| 5,349,053 | A | 9/1994 | Landolfi |
| 5,359,046 | A | 10/1994 | Capon et al. |
| 5,416,064 | A | 5/1995 | Chari et al. |
| 5,447,851 | A | 9/1995 | Beutler et al. |
| 5,500,362 | A | 3/1996 | Robinson et al. |
| 5,508,192 | A | 4/1996 | Georgiou et al. |

(Continued)

FOREIGN PATENT DOCUMENTS

| | | | |
|---|---|---|---|
| CN | 106939048 | A | 7/2017 |
| CN | 105555310 | | 7/2019 |

(Continued)

OTHER PUBLICATIONS

Kussie "A Single Engineered Amino Acid Substitution Changes Antibody Fine Specificity" J immunol 152(1):146-52 (Year: 1994).*
Allen et al., "Acute eosinophilic pneumonia as a reversible cause of noninfectious respiratory failure," N. Engl. J. Med., Aug. 31, 1989, 321(9):569-574.
Altschul et al., "Basic local alignment search tool," Journal of Molecular Biology, Oct. 1990, 215(3):403-410.
Altschul et al., "Gapped BLAST and PSI-BLAST: a new generation of protein database search programs," Nucleic Acids Res., Sep. 1, 1997, 25(17):3389-3402.

(Continued)

*Primary Examiner* — Adam Weidner
(74) *Attorney, Agent, or Firm* — Fish & Richardson P.C.

(57) ABSTRACT

The present disclosure provides single domain antibodies that bind to CD19, and chimeric antigen receptors comprising same. Further provided are engineered immune effector cells (such as T cells) comprising the chimeric antigen receptors. Pharmaceutical compositions, kits and methods of treating a disease or disorder are also provided.

20 Claims, 17 Drawing Sheets

Specification includes a Sequence Listing.

(56) References Cited

U.S. PATENT DOCUMENTS 5,530,101 A 6/1996 Queen et al.
5,545,807 A 8/1996 Surani et al.
5,565,332 A 10/1996 Hoogenboom et al.
5,585,089 A 12/1996 Queen et al.
5,605,793 A 2/1997 Stemmer
5,622,929 A 4/1997 Willner et al.
5,624,821 A 4/1997 Winter et al.
5,635,483 A 6/1997 Pettit et al.
5,639,635 A 6/1997 Joly et al.
5,648,237 A 7/1997 Carter
5,648,260 A 7/1997 Winter et al.
5,679,377 A 10/1997 Bernsein et al.
5,712,374 A 1/1998 Kuntsmann et al.
5,714,586 A 2/1998 Kuntsmann et al.
5,723,125 A 3/1998 Chang et al.
5,739,116 A 4/1998 Hamann et al.
5,766,886 A 6/1998 Studnicka et al.
5,767,285 A 6/1998 Hamann et al.
5,770,196 A 6/1998 Studnicka
5,770,701 A 6/1998 McGahren et al.
5,770,710 A 6/1998 McGahren et al.
5,773,001 A 6/1998 Hamann et al.
5,780,588 A 7/1998 Pettit et al.
5,783,181 A 7/1998 Browne et al.
5,811,238 A 9/1998 Stemmer et al.
5,821,123 A 10/1998 Studnicka
5,821,337 A 10/1998 Carter et al.
5,827,690 A 10/1998 Meade et al.
5,830,721 A 11/1998 Stemmer et al.
5,834,252 A 11/1998 Stemmer et al.
5,837,458 A 11/1998 Minshull et al.
5,844,095 A 12/1998 Linsley et al.
5,858,358 A 1/1999 June et al.
5,869,619 A 2/1999 Studnicka et al.
5,877,296 A 3/1999 Hamann et al.
5,883,223 A 3/1999 Gray
5,908,626 A 6/1999 Chang et al.
5,912,015 A 6/1999 Bernsein et al.
5,916,597 A 6/1999 Lee et al.
5,989,463 A 11/1999 Tracy et al.
6,027,888 A 2/2000 Georgiou et al.
6,054,297 A 4/2000 Carter et al.
6,075,181 A 6/2000 Kucherlapati et al.
6,083,715 A 7/2000 Georgiou et al.
6,150,584 A 11/2000 Kucherlapati et al.
6,194,551 B1 2/2001 Idusogie et al.
6,352,694 B1 3/2002 June et al.
6,407,213 B1 6/2002 Carter et al.
6,534,055 B1 3/2003 June et al.
6,602,684 B1 8/2003 Umana et al.
6,630,579 B2 10/2003 Chari et al.
6,639,055 B1 10/2003 Carter et al.
6,692,964 B1 2/2004 June et al.
6,719,971 B1 4/2004 Carter et al.
6,737,056 B1 5/2004 Presta
6,797,514 B2 9/2004 Berenson et al.
6,800,738 B1 10/2004 Carter et al.
6,867,041 B2 3/2005 Berenson et al.
6,887,466 B2 5/2005 June et al.
6,905,680 B2 6/2005 June et al.
6,905,681 B1 6/2005 June et al.
6,905,874 B2 6/2005 Berenson et al.
6,989,250 B2 1/2006 Soderlind et al.
7,052,906 B1 5/2006 Lawson et al.
7,067,318 B2 6/2006 June et al.
7,144,575 B2 12/2006 June et al.
7,172,869 B2 2/2007 June et al.
7,175,843 B2 2/2007 June et al.
7,232,566 B2 6/2007 June et al.
7,332,581 B2 2/2008 Presta
7,371,826 B2 5/2008 Presta
7,498,298 B2 3/2009 Doronina et al.
7,741,465 B1 6/2010 Eshhar et al.
7,985,840 B2 7/2011 Fuh et al.
8,603,930 B2 12/2013 Doesburg et al.
8,685,897 B2 4/2014 Bowers et al.
8,754,287 B2 6/2014 Macdonald et al.
2002/0164328 A1 11/2002 Shinkawa et al.
2003/0115614 A1 6/2003 Kanda et al.
2003/0157108 A1 8/2003 Presta
2003/0170238 A1 9/2003 Gruenberg et al.
2003/0186374 A1 10/2003 Hufton et al.
2004/0005709 A1 1/2004 Hoogenboom et al.
2004/0093621 A1 5/2004 Shitara et al.
2004/0101519 A1 5/2004 June et al.
2004/0109865 A1 6/2004 Niwa et al.
2004/0110282 A1 6/2004 Kanda et al.
2004/0110704 A1 6/2004 Yamane et al.
2004/0132140 A1 7/2004 Satoh et al.
2005/0014934 A1 1/2005 Hinton et al.
2005/0042664 A1 2/2005 Wu et al.
2005/0123546 A1 6/2005 Umana et al.
2006/0034810 A1 2/2006 Riley et al.
2006/0121005 A1 6/2006 Berenson et al.
2009/0075378 A1 3/2009 Horlick et al.
2009/0307787 A1 12/2009 Grosveld et al.
2010/0122358 A1 5/2010 Bruggemann
2011/0183855 A1 7/2011 Horlick et al.
2012/0028301 A1 2/2012 Horlick et al.
2014/0094392 A1 4/2014 Bowers et al.
2014/0170705 A1 6/2014 Bowers et al.
2014/0287509 A1 9/2014 Sharei et al.
2015/0289489 A1 10/2015 Macdonald et al.
2015/0299317 A1 10/2015 Orentas et al.
2017/0355756 A1* 12/2017 Julien .................... C07K 16/18
2018/0094044 A1 4/2018 Roessig et al.

FOREIGN PATENT DOCUMENTS

CN 110396128 A 11/2019
EP 0239400 9/1987
EP 0307434 3/1989
EP 0367166 5/1990
EP 0368684 5/1990
EP 0394827 10/1990
EP 0425235 5/1991
EP 0519596 12/1992
EP 0592106 4/1994
EP 3293199 3/2018
EP 3564266 11/2019
JP 2018525033 A 9/2018
WO WO 87/00195 1/1987
WO WO 90/03430 4/1990
WO WO 91/05548 5/1991
WO WO 91/06570 5/1991
WO WO 91/09967 7/1991
WO WO 93/11794 6/1993
WO WO 93/17105 9/1993
WO WO 94/04678 3/1994
WO WO 94/11026 5/1994
WO WO 94/29351 12/1994
WO WO 96/04388 2/1996
WO WO 96/20698 7/1996
WO WO 96/22024 7/1996
WO WO 96/34103 10/1996
WO WO 97/30087 8/1997
WO WO 97/34631 9/1997
WO WO 97/49805 12/1997
WO WO 98/58964 12/1998
WO WO 99/04813 2/1999
WO WO 99/15154 4/1999
WO WO 99/20253 4/1999
WO WO 99/22764 5/1999
WO WO 99/37681 7/1999
WO WO 99/51642 10/1999
WO WO 00/32776 6/2000
WO WO 00/43507 7/2000
WO WO 00/61739 10/2000
WO WO 01/29246 4/2001
WO WO 01/90190 11/2001
WO WO 02/031140 4/2002
WO WO 03/011878 2/2003
WO WO 03/014161 2/2003
WO WO 03/025020 3/2003

(56) References Cited

FOREIGN PATENT DOCUMENTS

| | | | |
|---|---|---|---|
| WO | WO 03/035694 | 5/2003 | |
| WO | WO 03/084570 | 10/2003 | |
| WO | WO 03/085107 | 10/2003 | |
| WO | WO 03/085119 | 10/2003 | |
| WO | WO 2004/049794 | 6/2004 | |
| WO | WO 2004/056312 | 7/2004 | |
| WO | WO 2005/035586 | 4/2005 | |
| WO | WO 2005/035778 | 4/2005 | |
| WO | WO 2005/053742 | 6/2005 | |
| WO | WO 2005/100402 | 10/2005 | |
| WO | WO 2006/003388 | 1/2006 | |
| WO | WO 2006/029879 | 3/2006 | |
| WO | WO 2006/030220 | 3/2006 | |
| WO | WO-2008068048 A2 * | 6/2008 | ............. A61P 31/10 |
| WO | WO 2008/077546 | 7/2008 | |
| WO | WO-2010130832 A2 * | 11/2010 | ............ C07K 14/51 |
| WO | WO 2015/158671 | 10/2015 | |
| WO | WO 2016/014789 | 1/2016 | |
| WO | WO 2016/102965 | 6/2016 | |
| WO | WO 2017/025038 A1 | 2/2017 | |
| WO | WO 2017/133175 | 8/2017 | |
| WO | WO 2018/067992 | 4/2018 | |
| WO | WO 2020/018922 | 1/2020 | |
| WO | WO 2020/113234 | 6/2020 | |

OTHER PUBLICATIONS

Arie et al., "Chaperone function of FkpA, a heat shock prolyl isomerase, in the periplasm of *Escherichia coli*," Mol. Microbiol., 2001, 39(1):199-210.
Ashkenazi et al., "Protection against endotoxic shock by a tumor necrosis factor receptor immunoadhesin," PNAS USA, Dec. 1, 1991, 88: 10535-10539.
Baca et al., Antibody Humanization Using Monovalent Phage Display, J. Biol. Chem., Apr. 18, 1997, 272(16):10678-10684.
Barnes et al., "Methods for growth of cultured cells in serum-free medium," Anal. Biochem., Mar. 1980, 102(2):255-270.
Bass et al., "Hormone phage: an enrichment method for variant proteins with altered binding properties," Proteins, 1990, 8(4):309-314.
Beck et al., "Trends in glycosylation, glycoanalysis and glycoengineering of therapeutic antibodies and Fc-fusion proteins," Curr. Pharm. Biotechnol., Dec. 2008, 9(6):482-501 (21 pages).
Berg et al, "Selective Expansion of a Peripheral Blood CD8+ Memory T Cell Subset Expressing Both Granzyme B and L-Selectin During Primary Viral Infection in Renal Allograft Recipients," Transplant Proc., 1998, 30(8):3975-3977.
Bierer et al., "Cyclosporin A and FK506: molecular mechanisms of immunosuppression and probes for transplantation biology," Curr. Opin. Immun., 1993, 5:763-773.
Bird et al, "Single-chain antigen-binding proteins," Science, Oct. 21, 1988, 242(4877):423-426.
Bitter et al., "[33] Expression and Secretion Vectors for Yeast," Methods in Enzymol., 1987, 153:516-544.
Blaise et al., "Construction and diversification of yeast cell surface displayed libraries by yeast mating: application to the affinity maturation of Fab antibody fragments," Gene, Nov. 24, 2004, 342(2):211-218.
Boder et al., "Yeast surface display for screening combinatorial polypeptide libraries, " Nat. Biotech., Jun. 1997, 15(6):553-557.
Boerner et al., "Production of antigen-specific human monoclonal antibodies from in vitro-primed human splenocytes," J. Immunol., Jul. 1, 1991, 147(1):86-95.
Bond et al., "A structure-based database of antibody variable domain diversity," J. Mol. Biol., May 6, 2005, 348(3):699-709.
Bothmann et al., "The periplasmic *Escherichia coli* peptidylprolyl cis,trans-isomerase FkpA. I. Increased functional expression of antibody fragments with and without cis-prolines," J. Biol. Chem., Jun. 2, 2000, 275(22):17100-17105.
Bradbury et al., "Antibodies from phage antibody libraries," J. Immunol. Methods, Jul. 2004, 290(1-2):29-49.
Bruggemann et al., "Comparison of the effector functions of human immunoglobulins using a matched set of chimeric antibodies," J. Exp. Med., Nov. 1987, 166(5):1351-1361.
Bruggemann et al., "Production of human antibody repertoires in transgenic mice," Curr. Opin. Biotechnol., Aug. 1997, 8(4):455-458.
Caldas et al., "Design and synthesis of germline-based hemi-humanized single-chain Fv against the CD18 surface antigen," Protein Eng., 2000, 13(5):353-360.
Carter et al., "Humanization of an anti-p185HER2 antibody for human cancer therapy," Proc. Natl. Acad Sci. USA, May 1992, 89:4285-4289.
Carter et al., "Signaling by the CD19/CD21 complex on B cells," Curr Dir Autoimmun., 2004, 7:4-32.
Carter, Paul, "Review Article: Site-directed mutagenesis," Biochem J., 1986, 237:1-7.
Chao et al., "Isolating and engineering human antibodies using yeast surface display," Nature Protocols, 2006, 1(2): 755-768.
Chen et al., "Chaperone activity of DsbC," J Bio Chem, Jul. 9, 1999, 274(28):19601-19605.
Chen et al., "Selection and analysis of an optimized anti-VEGF antibody: crystal structure of an affinity-matured Fab in complex with antigen," J. Mol Biol., Nov. 5, 1999, 293(4):865-881.
Chothia et al., Canonical structures for the hypervariable regions of immunoglobulins, J Mal. Biol., Aug. 20, 1987, 196(4):901-917.
Chowdhury, Partha S., "Engineering hot spots for affinity enhancement of antibodies," Methods Mol. Biol., 2003, 207:179-196.
Clackson et al., "Making antibody fragments using phage display libraries," Nature, Aug. 15, 1991, 352:624-628.
Clynes et al., "Fc receptors are required in passive and active immunity to melanoma," PNAS USA, Jan. 1998, 95:652-656.
Colberre-Garapin et al., "A new dominant hybrid selective marker for higher eukaryotic cells," J. Mol. Biol., Jul. 25, 1981, 150(1):1-14.
Colcher et al., "In Vivo Tumor Targeting of a Recombinant Single-Chain Antigen-Binding Protein," J. Nat. Cancer Inst., Jul. 18, 1990, 82(14):1191-1197.
Couto et al., "Anti-BA46 Monoclonal Antibody Mc3: Humanization Using a Novel Positional Consensus and in Vivo and in Vitro Characterization," Cancer Res., Apr. 15, 1995, 55(8): 1717-1722.
Couto et al., "Designing Human Consensus Antibodies with Minimal Positional Templates, " Cancer Res., Dec. 1, 1995, 55(23 Supp):5973s-5977s.
Cragg et al., "Antibody specificity controls in vivo effector mechanisms of anti-CD20 reagents," Blood, Apr. 2004, 103(7):2738-2743.
Cragg et al., "Complement-mediated lysis by anti-CD20 mAb correlates with segregation into lipid rafts," Blood, Feb. 2003, 101(3):1045-1052.
Crouse et al., "Expression and amplification of engineered mouse dihydrofolate reductase minigenes," Mol. Cell. Biol., Feb. 1983, 3(2):257-266.
Cunningham et al., "High-Resolution Epitope Mapping of hGH-Receptor Interactions by Alanine-Scanning Mutagenesis," Science, Jun. 2, 1989, 244:1081-1085.
Dall' Acqua et al., "Antibody humanization by framework shuffling," Methods, 2005, 36:43-60 (19 pages).
Damschroder et al., "Framework shuffling of antibodies to reduce immunogenicity and manipulate functional and biophysical properties," Mol. Immunol., 2007, 44(11):3049-3060.
Davies et al., "'Camelising' human antibody fragments: NMR studies on VH domains, " FEBS Letters, 1994, 339: 285-290.
Davies et al., "Single antibody domains as small recognition units: design and in vitro antigen selection of camelized, human VH domains with improved protein stability," Protein Engineering, 1996, 9(6):531-537.
Davila et al., "CD19 CAR-Targeted T Cells Induce Long-Term Remission and B Cel 1Aplasia in an Immunocompetent Mouse Model of B Cell Acute Lymphoblastic Leukemia," PLoS ONE, Apr. 2013, 8(4): e61338 (14 pages).

(56) References Cited

OTHER PUBLICATIONS

De Groot et al., "Evolutionary deimmunization: An ancillary mechanism for self-tolerance?," Cell. Immunol., Dec. 2006, 244(2):148-153.
Deschacht et al., "A Novel Promiscuous Class of Camelid Single-Domain Antibody Contributes to the Antigen-Binding Repertoire," J Immunol., May 15, 2010, 184(10):5696-5704.
Dubowchik et al., "Doxorubicin immunoconjugates containing bivalent, lysosomally-cleavable dipeptide linkages," Bioorg. Med. Chem. Lett., Jun. 3, 2002, 12(11):1529-1532.
Dufner et al., "Harnessing phage and ribosome display for antibody optimisation," Trends Biotechnol., Dec. 2006, 24(11):523-529.
Duncan et al., "The binding site for C1q on IgG," Nature, Apr. 21, 1988, 322(6166):738-740.
During et al., "Controlled Release of Dopamine from a Polymeric Brain Implant: In Vivo Characterization," Ann. Neurol., 1989, 25:351-356.
Els Pardon et al., "A general protocol for the generation of Nanobodies for structural biology," Nature Protocol., Mar. 2014, 9(3): 674-693.
Feldhaus et al., "Flow Cytometric Isolation of Human Antibodies from a Nonimmune *Saccharomyces cerevisiae* Surface Display Library," Nat. Biotechnol., Jan. 2003, 21(2):163-170.
Foote et al., "Antibody Framework Resides Affecting the Conformation of the Hypervariable Loops," J. Mol. Biol. 1992, 224:487-499.
Fukuda et al, "Invitro evolution of single-chain antibodies using mRNA display," Nucleic Acids Res., 2006, 34(19):e127 (8 pages).
Garland et al, "The use of Teflon cell culture bags to expand functionally active CD8+ Cytotoxic T lymphocytes," J. Immunol Meth., 1999, 227(1-2):53-63.
Gazzano-Santoro et al., "A non-radioactive complement-dependent cytotoxicity assay for anti-CD20 monoclonal antibody," J Immunol. Methods, Mar. 28, 1997, 202(2):163-171.
Graham et al., "Characteristics of a human cell line transformed by DNA from human adenovirus type 5," J. Gen Virol., Jul. 1977, 36(1):59-72.
Guex et al., SWISS-MODEL and the Swiss-Pdb Viewer: An environment for comparative protein modeling, Electrophoresis, 1997, 18:2714-2723.
Guyer et al., "Immunoglobulin binding by mouse intestinal epithelial cell receptors," J. Immunol., Aug. 1976, 117(2):587-593.
Haanen et al., "Selective Expansion of Cross-reactive CD8 Memory T Cells by Viral Variants," J. Exp. Med., Nov. 1, 1999, 190(9):1319-1328.
Ham et al., "[5] Media and growth requirements," Meth. Enz., 1979, 58:44-93.
Hamers-Casterman et al., "Naturally occurring antibodies devoid of light chains," Nature, Jun. 3, 1993, 363:446-448.
Hansson et al., "Evolution of differential substrate specificities in Mu class glutathione transferases probed by DNA shuffling," J. Mol. Biol., Mar. 26, 1999, 287(2):265-276.
Hara et al., "Overproduction of penicillin-binding protein 7 suppresses thermosensitive growth defect at low osmolarity due to an spr mutation of *Escherichia coli*," Microbial Drug Resistance, Spring 1996, 2(1):63-72.
Harayama, S., "Artificial evolution by DNA shuffling," Trends Biotechnol., Feb. 1998, 16(2):76-82.
Hellstrom et al., "Antitumor effects of L6, an IgG2a antibody that reacts with most human carcinomas," Proc. Nat'l Acad. Sci. USA, Sep. 1986, 83:7059-7063.
Hellstrom et al., "Strong antitumor activities of IgG3 antibodies to a human melanoma-associated ganglioside," PNAS USA, Mar. 1985, 82: 1499-1502.
Henderson et al., "Comparison of the effects of FK-506, cyclosporin A and Rapamycin on IL-2 production," Immun., 1991, 73:316-321.
Hermans et al., "The VITAL assay: a versatile fluorometric technique for assessing CTL- and NKT-mediated cytotoxicity against multiple targets in vitro and in vivo," J. Immunological Methods, Feb. 1, 2004, 285(1):25-40.
Hinman et al., "Preparation and characterization of monoclonal antibody conjugates of the calicheamicins: a novel and potent family of antitumor antibiotics," Cancer Res., Jul. 15, 1993, 53(14):3336-3342.
Ho et al., "In Vitro Antibody Evolution Targeting Germline Hot Spots to Increase Activity of an Anti-CD22 Immunotoxin*," J Biol. Chem., Jan. 7, 2005, 280:607-617.
Holt et al., "Domain antibodies: proteins for therapy," Trends Biotechnol., Nov. 2003, 21(11):484-490.
Honegger et al., "Yet Another Numbering Scheme for Immunoglobulin Variable Domains: An Automatic Modelinga nd Analysis Tool," J. Mol. Biol., 2001, 309:657-670.
Hoogenboom et al., "By-passing Immunisation Human Antibodies from Synthetic Repertoires of Germline VH Gene Segments Rearranged in Vitro," J. Mol. Biol., 1992, 227:381-388.
Hoogenboom et al., "Overview of antibody phage-display technology and its applications," Methods Mol. Biology, 2002, 178:1-37.
Hoogenboom, Hennie, "Selecting and screening recombinant antibody libraries," Nat. Biotechnol., Sep. 2005, 23(9):1105-1016.
Howard et al., "Intracerebral drug delivery in rats with lesion-induced memory deficits," J. Neurosurg., 1989, 71(1):105-112.
Huston et al., "Antigen recognition and targeted delivery by the single-chain Fv," Cell Biophysics, Jan. 1993, 22:189-224.
Idusogie et al., "Mapping of the C1q Binding Site on Rituxan, a Chimeric Antibody with a Human IgG1 Fc," J Imnnmol., 2000, 164(8):4178-4184.
Inouye et al., "Up-promoter mutations in the lpp gene of *Escherichia coli*," Nucleic Acids Res., May 10, 1985, 13(9):3101-3109.
Jakobovits, "Production of fully human antibodies by transgenic mice," Curr. Opin. Biotechnol., 1995, 6(5):561-566.
Jeffrey et al., "Dipeptide-based highly potent doxorubicin antibody conjugates," Bioorganic Med. Chem. Lett., Jan. 15, 2006, 16(2):358-362.
Jones et al., "Deimmunization of Monoclonal Antibodies," Methods Mol Biol., 2009, 525:405-423.
Jones et al., "Replacing the complementarity-determining regions in a human antibody with those from a mouse," Nature, May 29, 1986, 321:522-525.
Kanda et al., "Comparison of cell lines for stable production of fucose-negative antibodies with enhanced ADCC," Biotechnol. Bioeng., Jul. 5, 2006, 94(4):680-688.
Karlin et al., "Applications and statistics for multiple high-scoring segments in molecular sequences," Proc. Natl. Acad. Sci. U.S.A., Jun. 1993, 90:5873-5877.
Karlin et al., "Methods for assessing the statistical significance of molecular sequence features by using general scoring schemes," PNAS U.S.A., Mar. 1990, 87:2264-2268.
Kashmiri et al.,"SDR grafting-a new approach to antibody humanization," Methods, May 2005, 36(1):25-34 (11 pages).
Kim et al., "Identifying amino acid residues that influence plasma clearance of murine IgG1 fragments by site-directed mutagenesis," J Immunol., 1994, 24:542-548.
King et al., "Monoclonal antibody conjugates of doxorubicin prepared with branched peptide linkers: inhibition of aggregation by methoxytriethyleneglycol chains," J. Med. Chem., Sep. 12, 2002, 45(19):4336-4343.
Kochenderfer et al., "Construction and Pre-clinical Evaluation of an Anti-CD19 Chimeric Antigen Receptor," J. Immunotherapy, Sep. 2009, 32(7):689-702.
Kohler et al., "Continuous cultures of fused cells secreting antibody of predefined specificity," Nature, Aug. 1975, 256(5517):495-497.
Kratz et al., "Prodrugs of anthracyclines in cancer chemotherapy," Current Med. Chem., 2006, 13(5):477-523.
Langer et al., "Chemical and Physical Structure of Polymers as Carriers for Controlled Release of Bioactive Agents: A Review," J. Macromol Sci. Rev. Macromol. Chem., 1983, 23(1):61-126.
Langer, Robert, "New Methods of Drug Delivery," Science, Sep. 28, 1990, 249: 1527-1533.
Lazar et al., "A molecular immunology approach to antibody humanization and functional optimization," Mol. Immunol., 2007, 44:1986-1998.

(56) References Cited

OTHER PUBLICATIONS

Lefranc et al., "IMGT unique numbering for immunoglobulin and T cell receptor variable domains and Ig superfamily V-like domains," Dev. Comp. Immunol., Jan. 2003, 27(1):55-77.
Levy et al., "Inhibition of Calcification of Bioprosthetic Heart Valves by Local Controlled-Release Diphosphonate," Science, Apr. 12, 1985, 228: 190-192.
Li et al., "Construction and characterization of a humanized anti-human CD3 monoclonal antibody 12F6 with effective immunoregulation functions," Immunology, 2005, 116:487-498.
Li et al., "Human antibodies for immunotherapy development generated via a human B cell hybridoma technology," Proc. Natl. Acad Sci. USA, Mar. 7, 2006, 103:3557-3562.
Liu et al., "Calcineurin Is a Common Target of Cyclophilin-Cyclosporin A and FKBP-FK506 Complexes," Cell, Aug. 23, 1991, 66:807-815.
Lode et al., "Targeted therapy with a novel enediyene antibiotic calicheamicin theta(I)1 effectively suppresses growth and dissemination of liver metastases in a syngeneic model of murine neuroblastoma," Cancer Res., Jul. 15, 1998, 58(14):2925-2928.
Logan et al., "Adenovirus tripartite leader sequence enhances translation of mRNAs late after infection," Proc. Natl. Acad. Sci. USA, Jun. 1984, 81:3655-3659.
Lorenzo et al., "PCR-Based Method for the Introduction of Mutations in Genes Cloned and Expressed in Vaccinia Virus," Biotechniques, Feb. 1998, 24(2):308-313.
Lowy et al., "Isolation of Transforming DNA: Cloning the Hamster aprt Gene," Cell, Dec. 1980, 22:817-823.
Lu et al., "Tailoring in Vitro Selection for a Picomolar Affinity Human Antibody Directed against Vascular Endothelial Growth Factor Receptor 2 for Enhanced Neutralizing Activity*," J. Biol. Chem., Oct. 31, 2005, 278(44):43496-43507.
Marks et al., "By-Passing Immunization: Building High Affinity Human Antibodies by Chain Shuffling," Bio/Technology, 10:779-783 (1992).
Marks et al., "By-passing immunization: Human antibodies from V-gene libraries displayed on phage," J Mol. Biol., Dec. 5, 1991, 222(3):581-597.
Mather et al., "Culture of testicular cells in hormone-supplemented serum-free medium," Annals. NY Acad Sci., 1982, 383:44-68.
Mather, J P., "Establishment and characterization of two distinct mouse testicular epithelial cell lines," Biol. Reprod., Aug. 1980, 23(1):243-252.
McCafferty et al., Phage antibodies: filamentous phage displaying antibody variable domains, Nature, Dec. 6, 1990, 348:552-554.
Merrifield, R. B., "Solid Phase Peptide Synthesis. I. The Synthesis of a Tetrapeptide," J. Am. Chem. Soc., Jul. 1963, 85(14):2149-2154.
Milone et al., "Chimeric Receptors Containing CD137 Signal Transduction Domains Mediate Enhanced Survival of T Cells and Increased Antileukemic Efficacy In Vivo," Molecular Therapy, Aug. 2009, 17(8):1453-1464.
Morea et al., "Antibody Modeling: Implications for Engineering and Design," Methods, 2000, 20(3):267-279.
Morgan et al., "Human gene therapy," Annu. Rev. Biochem., 1993, 62:191-217.
Morrison et al., "Chimeric human antibody molecules: Mouse antigen-binding domains with human constant region domains," Proc. Natl. Acad Sci. USA, Nov. 1984, 81:6851-6855.
Mulligan et al., "Selection for animal cells that express the *Escherichia coli* gene coding for xanthine-guanine phosphoribosyltransferase," Proc. Natl. Acad. Sci. USA, Apr. 1981, 78(4):2072-2076.
Mulligan, R.C., "The basic science of gene therapy," Science, May 14, 1993, 260(5110):926-932.
Muyldermans, Serge, "Single domain camel antibodies: current status," Reviews Mol Biotech., 2001, 74:277-302 (2001).
Myers et al., "Optimal alignments in linear space," CABIOS, Mar. 1988, 4(1):11-17.
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc. Natl. Acad Sci. USA, Jan. 18, 2000, 97(2):829-834.
Ning et al., "Intratumoral radioimmunotherapy of a human colon cancer xenograft using a sustained-release gel," Radiotherapy & Oncology, May 1996, 39(2):179-189.
O'Hare et al., "Transformation of mouse fibroblasts to methotrexate resistance by a recombinant plasmid expressing a prokaryotic dihydrofolate reductase.," Proc. Natl. Acad. Sci. USA, Mar. 1981, 78(3):1527-1531.
Okazaki et al., "Fucose depletion from human IgG1 oligosaccharide enhances binding enthalpy and association rate between IgG1 and FcgammaRIIIa," J Mol. Biol., Mar. 5, 2004, 336(5): 1239-1249.
Padlan et al., "Identification of specificity-determining residues in antibodies," FASEB J., Jan. 1995, 9(1):133-139.
Padlan, E. A., "A possible procedure for reducing the immunogenicity of antibody variable domains while preserving their ligand-binding properties," Mal. Immunol., Apr.-May 1991, 28(4-5):489-498.
Patten et al., "Applications of DNA shuffling to pharmaceuticals and vaccines," Curr. Opinion Biotechnol., Dec. 1997, 8(6):724-733.
PCT International Search Report and Written Opinion in International Appln. No. PCT/CN2021/106892, mailed on Oct. 25, 2021, 10 pages.
Pedersen et al., "Comparison of Surface Accessible Residues in Human and Murine Immunoglobulin Fv Domains: Implication for Humanization of Murine Antibodies," J. Mol. Biol., 1994, 235(3):959-973.
Petkova et al., "Enhanced half-life of genetically engineered human IgG1 antibodies in a humanized FcRn mouse model: potential application in humorally meditated autoimmune disease," Int'l. Immunol., 2006, 18(12): 1759-1769.
Pluckthun et al., "Expression of functional antibody Fv and Fab fragments in *Escherichia coli*," Meth. Enzymol., 1989, 178:497-515.
Pluckthun, Andreas, "Mono-and bivalent antibody fragments produced in *Escherichia coli*: engineering, folding and antigen binding," Immunol. Revs., Dec. 1992, 130: 151-188.
Presta et al., "Humanization of an antibody directed against IgE," J Immunol., 1993, 151(5):2623-2632.
Presta, Leonard G., "Antibody engineering," Curr. Op. Struct. Biol., 1992, 2:593-596.
Quiroz et al., "Engineering antibody fragments: replicating the immune system and beyond," Revista Ingeneria Biomedica, 2010, 4(7):39-51.
Rabinovich et al., "Synthetic Messenger RNA as a Tool for Gene Therapy," Human Gene Therapy, Oct. 2006, 17:1027-1035.
Ramm et al., "The periplasmic *Escherichia coli* peptidylprolyl cis, trans-isomerase FkpA. II. Isomerase-independent chaperone activity in vitro," J. Biol. Chem., Jun. 2, 2000, 275(22):17106-17113.
Riechmann et al., "Reshaping human antibodies for therapy," Nature, Mar. 1988, 332:323-329.
Riechmann et al., "Single domain antibodies: comparison of camel VH and camelised human VH domains," J. Immunol. Meth., 1999, 231: 25-38.
Riechmann, Lutz, "Rearrangement of the Former VL Interface in the Solution Structure of a Camelised, Single Antibody VH Domain," J. Mol. Biol., Jun. 28, 1996, 259(5): 957-969.
Ripka et al. "Two Chinese hamster ovary glycosylation mutants affected in the conversion of GDP-mannose to GDP-fucose," Arch. Biochern. Biophys., Sep. 1986, 249(2):533-545.
Rivollier et al., "Immature dendritic cell transdifferentiation into osteoclasts: a novel pathway sustained by the rheumatoid arthritis microenvironment," Blood, Dec. 15, 2004, 104(13):4029-4037.
Roguska et al, "Humanization of murine monoclonal antibodies through variable domain resurfacing," PNAS, Feb. 1994, 91:969-973.
Roguska et al., "A comparison of two murine monoclonal antibodies humanized by CDR-grafting and variable domain resurfacing," Protein Eng., 1996, 9(10):895-904.
Rosenberg, Steven A., "Cell transfer immunotherapy for metastatic solid cancer—what clinicians need to know," Nat Rev Clin Oncol., Aug. 2, 2011, 8(10):577-585.

(56) References Cited

OTHER PUBLICATIONS

Ruther et al., "Easy identification of cDNA clones," EMBO, Oct. 1983, 2(10):1791-1794.
Sali et al., "Comparative Protein Modelling by Satisfaction of Spatial Restraints," J. Mol. Biol., 1993, 234:779-815.
Sandhu, J.S., "A rapid procedure for the humanization of monoclonal antibodies," Gene, Dec. 15, 1994, 150(2):409-410.
Santerre et al., "Expression of prokaryotic genes for hygromycin B and G418 resistance as dominant-selection markers in mouse L cells," Gene, Oct. 1984, 30(1-3):147-156.
Schlapschy et al., "Functional humanization of an anti-CD30 Fab fragment for the immunotherapy of Hodgkin's lymphoma using an in vitro evolution approach," Protein Eng. Des. Sel., Dec. 2004, 17(12):847-860.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol. Chem., Mar. 2, 2001, 276(9): 6591-6604.
Shusta et al., "Yeast polypeptide fusion surface display levels predict thermal stability and soluble secretion efficiency," J. Mol. Biol., Oct. 8, 1999, 292(5):949-956.
Siebenlist et al., "*E. coli* RNA Polymerase Interacts Homologously with Two Different Promoters," Cell, Jun. 1980, 20: 269-281.
Simmons et al., "Expression of full-length immunoglobulins in *Escherichia coli*: rapid and efficient production of aglycosylated antibodies," J. Immunol. Methods, May 2002, 263(1-2):133-147.
Sims et al., "A humanized CD18 antibody can block function without cell destruction," J Immunol., Aug. 15, 1993, 151(4):2296-2308.
Skerra et al., "Bacterial expression of immunoglobulin fragments," Curr. Opinion in Immunol., Apr. 1993, 5(2):256-262.
Streltsov et al., "Structure of a shark IgNAR antibody variable domain and modeling of an early-developmental isotype," Protein Sci., 2005, 14:2901-2909.
Studnicka et al, "Human-engineered monoclonal antibodies retains full specific binding activity by preserving non-CDR complementarity-modulating residues," Protein Engineering, 1994, 7(6):805-814.
Tan et al., ""Superhumanized" Antibodies: Reduction of Immunogenic Potential by Complementarity-Determining Region Grafting with Human Germline Sequences: Application to an Anti-CD281," J.Immunol., Jul. 15, 2002, 169(2): 1119-1125.
Taylor et al., "A transgenic mouse that expresses adiversity of human sequence heavy and light chain immunoglobulins," Nucl. Acids Res., 1992, 20(23):6287-6295.
Terpe, K., "Overview of tag protein fusions: from molecular and biochemical fundamentals to commercial systems," Appl. Microbiol. Biotechnol., Jan. 2003, 60(5):523-533.
Themeli et al., "Generation of tumor-targeted human T lymphocytes from induced pluripotent stem cells for cancer therapy," Nat Biotechnol., 2013, 31(10):928-933.
Thorpe et al., "The preparation and cytotoxic properties of antibody-toxin conjugates," Immunol. Rev., 1982, 62:119-158.
Tolstoshev, P., "Gene therapy, concepts, current trials and future directions," Annu. Rev Pharmacol. Toxicol., 1993, 32:573-596.
Torgov et al., "Generation of an intensely potent anthracycline by a monoclonal antibody-beta-galactosidase conjugate," Bioconjug. Chem., May-Jun. 2005, 16(3):717-721.
Traunecker et al., "Soluble CD4 molecules neutralize human immunodeficiency virus type 1," Nature, Jan. 1988, 331(6151):84-86.
Tsukahara et al., "CD19 target-engineered T-cells accumulate at tumor lesions in human B-cell lymphoma xenograft mouse models," Biochem Biophys Res Commun., 2013, 438(1):84-89.
Ui-Tei et al., "Sensitive assay of RNA interference in *Drosophila* and Chinese hamster cultured cells using firefly luciferase gene as target," FEBS Letters, 2000, 479:79-82.
Urlaub et al., "Isolation of Chinese hamster cell mutants deficient in dihydrofolate reductase activity," Pnas USA, Jul. 1980, 77(7):4216-4220.
Van Dijk et al., "Human antibodies as next generation therapeutics," Curr. Opin. Chemical Biolo., 2001, 5:368-374.
Van Heeke et al., "Expression of human asparagine synthetase in *Escherichia coli*," J. Biol. Chem., Apr. 5, 1989, 24(10):5503-5509.
Verhoeyen et al., "Reshaping Human Antibodies: Grafting an Antilysozyme Activity," Science, 1988, 239:1534-1136.
Vil et al., "Human fusion proteins between interleukin 2 and IgM heavy chain are cytotoxic for cells expressing the interleukin 2 receptor," Proc. Natl. Acad. Sci. USA, Dec. 1992, 89(23):11337-11341.
Vincke et al., "General Strategy to Humanize a Camelid Single-domain Antibody and Identification of a Universal Humanized Nanobody Scaffold," J. Biol. Chem, Jan. 30, 2009, 284(5):3273-3284.
Vitetta et al., "Redesigning nature's poisons to create anti-tumor reagents," Science, Nov. 20, 1987, 238(4830):1098-1104 (9 pages).
Walsh, Gary, "Post-translational modifications of protein biopharmaceuticals," Drug Discov. Today, Sep. 2010, 15(17-18):773-780.
Wang et al., "CD19: a biomarker for B cell development, lymphoma diagnosis and therapy, " Exp Hematol Oncol., Nov. 29, 2012, 1(1): 36 (7 pages).
Ward et al., "Binding activities of a repertoire of single immunoglobulin variable from *Escherichia coli*," Nature, Oct. 12, 1989, 341:544-546.
Waterhouse et al., "Combinatorial infection and in vivo recombination: a strategy for making large phageantibody repertoires," Nucl. Acids Res., 1993, 21(9):2265-2266.
Wells et al., "Cassette mutagenesis: an efficient method for generation of multiple mutations at defined sites," Gene, 1985, 34(2-3):315-323.
Whitelegg et al., "WAM: an improved algorithm for modelling antibodies on the WEB," Protein Eng., 2000, 13(12):819-824.
Wigler et al., "Transfer of Purified Herpes Virus Thymidine Kinase Gene to Cultured Mouse Cells," Cell, May 1977, 11:223-232.
Wilson et al., "The use of mRNA display to select high-affinity protein-binding peptides," Proc. Natl. Acad. Sci. USA, Mar. 27, 2001, 98(7):3750-3755.
Wright et al., "Effect of glycosylation on antibody function: implications for genetic engineering," TIBTECH, Jan. 1997, 15(1):26-32.
Wu et al., "Delivery systems for gene therapy," Biotherapy, 1991, 3(1):87-95.
Yamane-Ohnuki et al., "Establishment of FUT8 knockout Chinese hamster ovary cells: An ideal host cell line for producing completely defucosylated antibodies with enhanced antibody-dependent cellular cytotoxicity," Biotech. Bioeng., 2004, 87(5):614-622.
Yaniv, M., "Enhancing elements for activation of eukaryotic promoters," Nature, May 6, 1982, 297(5861):17-18.
Yu et al., "Next generation chimeric antigen receptor T cells: safety strategies to overcome toxicity," Molecular Cancer, 2019, 18(1):125 (13 pages).
Zheng et al., "Administration of noncytolytic IL-10/Fc in murine models of lipopolysaccharide-induced septic shock and allogeneic islet transplantation," J. Immunol., May 15, 1995, 154(10):5590-5600.
Zhou et al., "Structure of the genes encoding the CD19 antigen of human and mouse B lymphocytes," Immunogenetics., 1992, 35(2): 102-111.
Zoller et al., "Oligonucleotide-directed mutagenesis using M13-derived vectors: an efficient and general procedure for the production of point mutations in any fragment of DNA," Nucl. Acids Res., Oct. 25, 1982, 10(20):6487-6500.
Zurfluh et al., "Auxin-induced changes in the patterns of protein synthesis in soybean hypocotyl," Proc. Natl. Acad. Sci. USA, Jan. 1980, 77(1):357-361.
Extended European Search Report in European Appln. No. 21843054.4, mailed on Nov. 12, 2024, 16 pages.
Partial Supplementary European Search Report in European Appln. No. 21843054.4, mailed on Aug. 22, 2024, 16 pages.
GenBank Accession No. NM_001770.5, "*Homo sapiens* CD19 molecule (CD19), transcript variant 2, mRNA," Jun. 26, 2019, 6 pages.
International Preliminary Report on Patentability in International Appln. No. PCT/CN2021/106892, mailed on Jan. 26, 2023, 7 pages.

(56) References Cited

OTHER PUBLICATIONS

Munson et al., "Ligand: a versatile computerized approach for characterization of ligand-binding systems," Anal. Biochem., Sep. 1980, 107(1):220-239.
Steinfeld et al., "Epratuzumab (humanised anti-CD22 antibody) in autoimmune diseases," Expert. Opin. Biol. Ther., Sep. 2006, 6(9):943-949.
Wigler et al., "Transformation of mammalian cells with an amplifiable dominant-acting gene," Proc Natl Acad Sci U S A, Jun. 1980, 77(6):3567-3570.

* cited by examiner

SEQUENCE LISTING

```
<160> NUMBER OF SEQ ID NOS: 114

<210> SEQ ID NO 1
<211> LENGTH: 8
<212> TYPE: PRT
<213> ORGANISM: Artificial Sequence
<220> FEATURE:
<223> OTHER INFORMATION: CDR1 of VHH-083 (IMGT) or VHH-131 (IMGT)

<400> SEQUENCE: 1

Gly Asn Ile Asn Ser Arg Asn Cys
```

1 5

<210> SEQ ID NO 2
<211> LENGTH: 8
<212> TYPE: PRT
<213> ORGANISM: Artificial Sequence
<220> FEATURE:
<223> OTHER INFORMATION: CDR1 of VHH-111 (IMGT)

<400> SEQUENCE: 2

Gly Asp Thr Leu Ser Asn Lys Trp
1 5

<210> SEQ ID NO 3
<211> LENGTH: 8
<212> TYPE: PRT
<213> ORGANISM: Artificial Sequence
<220> FEATURE:
<223> OTHER INFORMATION: CDR1 of 77LICA542 (IMGT)

<400> SEQUENCE: 3

Gly Tyr Thr Tyr Ser Ser Gly Cys
1 5

<210> SEQ ID NO 4
<211> LENGTH: 8
<212> TYPE: PRT
<213> ORGANISM: Artificial Sequence
<220> FEATURE:
<223> OTHER INFORMATION: CDR1 of 77LICA519 (IMGT)

<400> SEQUENCE: 4

Gly Leu Pro Tyr Thr Gly Tyr Cys
1 5

<210> SEQ ID NO 5
<211> LENGTH: 8
<212> TYPE: PRT
<213> ORGANISM: Artificial Sequence
<220> FEATURE:
<223> OTHER INFORMATION: CDR1 of 77LICA602 (IMGT)

<400> SEQUENCE: 5

Gly Tyr Thr Ser Ser Tyr Ala Tyr
1 5

<210> SEQ ID NO 6
<211> LENGTH: 8
<212> TYPE: PRT
<213> ORGANISM: Artificial Sequence
<220> FEATURE:
<223> OTHER INFORMATION: CDR1 of LIC1157 (IMGT)

<400> SEQUENCE: 6

Gly Phe Thr Phe Ser Asp Ala Val
1 5

<210> SEQ ID NO 7
<211> LENGTH: 8
<212> TYPE: PRT
<213> ORGANISM: Artificial Sequence
<220> FEATURE:
<223> OTHER INFORMATION: CDR1 of LIC1159 (IMGT)

<400> SEQUENCE: 7

Gly Arg Thr Phe Ser Ser Leu Ala
1 5

<210> SEQ ID NO 8
<211> LENGTH: 8
<212> TYPE: PRT
<213> ORGANISM: Artificial Sequence
<220> FEATURE:
<223> OTHER INFORMATION: CDR2 of VHH-083 (IMGT) or VHH-131 (IMGT)

<400> SEQUENCE: 8

Ile Gly Gln Val Thr Gly Arg Ser
1               5

<210> SEQ ID NO 9
<211> LENGTH: 8
<212> TYPE: PRT
<213> ORGANISM: Artificial Sequence
<220> FEATURE:
<223> OTHER INFORMATION: CDR2 of VHH-111 (IMGT)

<400> SEQUENCE: 9

Ile Arg Thr Asp His Ala Gly Thr
1               5

<210> SEQ ID NO 10
<211> LENGTH: 7
<212> TYPE: PRT
<213> ORGANISM: Artificial Sequence
<220> FEATURE:
<223> OTHER INFORMATION: CDR2 of 77LICA542 (IMGT)

<400> SEQUENCE: 10

Ile Asp Ser Asp Gly Met Thr
1               5

<210> SEQ ID NO 11
<211> LENGTH: 8
<212> TYPE: PRT
<213> ORGANISM: Artificial Sequence
<220> FEATURE:
<223> OTHER INFORMATION: CDR2 of 77LICA519 (IMGT)

<400> SEQUENCE: 11

Ile Ser Thr Gly Ser Gly Gly Thr
1               5

<210> SEQ ID NO 12
<211> LENGTH: 7
<212> TYPE: PRT
<213> ORGANISM: Artificial Sequence
<220> FEATURE:
<223> OTHER INFORMATION: CDR2 of 77LICA602 (IMGT)

<400> SEQUENCE: 12

Ile Gly Ser Asn Gly Arg Thr
1               5

<210> SEQ ID NO 13
<211> LENGTH: 8
<212> TYPE: PRT
<213> ORGANISM: Artificial Sequence
<220> FEATURE:
<223> OTHER INFORMATION: CDR2 of LIC1157 (IMGT)

<400> SEQUENCE: 13

Ile Ser Asn Gly Gly Ile Thr Arg
1               5

<210> SEQ ID NO 14
<211> LENGTH: 8
<212> TYPE: PRT
<213> ORGANISM: Artificial Sequence
<220> FEATURE:
<223> OTHER INFORMATION: CDR2 of LIC1159 (IMGT)

<400> SEQUENCE: 14

Ile Ser Trp Ser Gly Gly Ser Ile
1 5

<210> SEQ ID NO 15
<211> LENGTH: 18
<212> TYPE: PRT
<213> ORGANISM: Artificial Sequence
<220> FEATURE:
<223> OTHER INFORMATION: CDR3 of VHH-083 (IMGT) or VHH-131 (IMGT)

<400> SEQUENCE: 15

Ala Ala Ala Pro Gly Cys Leu Leu Ser Ala Leu Arg Ser Ala Asp Tyr
1 5 10 15

Arg Asn

<210> SEQ ID NO 16
<211> LENGTH: 12
<212> TYPE: PRT
<213> ORGANISM: Artificial Sequence
<220> FEATURE:
<223> OTHER INFORMATION: CDR3 of VHH-111 (IMGT)

<400> SEQUENCE: 16

Ala Ala Ser Tyr Ser Gly Ala Thr Thr Phe Arg Tyr
1 5 10

<210> SEQ ID NO 17
<211> LENGTH: 19
<212> TYPE: PRT
<213> ORGANISM: Artificial Sequence
<220> FEATURE:
<223> OTHER INFORMATION: CDR3 of 77LICA542 (IMGT)

<400> SEQUENCE: 17

Ala Ala Asp Pro Asp Cys Tyr Tyr Ser Asp Tyr Ala Ile Ser Pro Ala
1 5 10 15

Phe Gly Tyr

<210> SEQ ID NO 18
<211> LENGTH: 19
<212> TYPE: PRT
<213> ORGANISM: Artificial Sequence
<220> FEATURE:
<223> OTHER INFORMATION: CDR3 of 77LICA519 (IMGT)

<400> SEQUENCE: 18

Ala Ala Gly Leu Arg Leu Pro Gly Arg Ala Cys Thr Thr Ser His Lys
1 5 10 15

Tyr Asn Tyr

<210> SEQ ID NO 19
<211> LENGTH: 19
<212> TYPE: PRT
<213> ORGANISM: Artificial Sequence
<220> FEATURE:
<223> OTHER INFORMATION: CDR3 of 77LICA602 (IMGT)

<400> SEQUENCE: 19

Ala Ala Arg Arg Trp Gly Trp Gly Glu Leu Pro Leu Thr Pro Ser Glu
1 5 10 15

Tyr Asn Asn

<210> SEQ ID NO 20
<211> LENGTH: 9
<212> TYPE: PRT
<213> ORGANISM: Artificial Sequence
<220> FEATURE:
<223> OTHER INFORMATION: CDR3 of LIC1157 (IMGT)

<400> SEQUENCE: 20

Ala Lys Arg Ala Pro Gly Asp Lys Val
1 5

<210> SEQ ID NO 21
<211> LENGTH: 15
<212> TYPE: PRT
<213> ORGANISM: Artificial Sequence
<220> FEATURE:
<223> OTHER INFORMATION: CDR3 of LIC1159 (IMGT)

<400> SEQUENCE: 21

Ala Ala Asp Arg Thr Leu Gln Ala Thr Met Ser Glu Ile Ser Tyr
1 5 10 15

<210> SEQ ID NO 22
<211> LENGTH: 10
<212> TYPE: PRT
<213> ORGANISM: Artificial Sequence
<220> FEATURE:
<223> OTHER INFORMATION: CDR1 of VHH-083 (Kabat) or VHH-131 (Kabat)

<400> SEQUENCE: 22

Gly Asn Ile Asn Ser Arg Asn Cys Met Gly
1 5 10

<210> SEQ ID NO 23
<211> LENGTH: 10
<212> TYPE: PRT
<213> ORGANISM: Artificial Sequence
<220> FEATURE:
<223> OTHER INFORMATION: CDR1 of VHH-111 (Kabat)

<400> SEQUENCE: 23

Gly Asp Thr Leu Ser Asn Lys Trp Met Gly
1 5 10

<210> SEQ ID NO 24
<211> LENGTH: 10
<212> TYPE: PRT
<213> ORGANISM: Artificial Sequence
<220> FEATURE:
<223> OTHER INFORMATION: CDR1 of 77LICA542 (Kabat)

<400> SEQUENCE: 24

Gly Tyr Thr Tyr Ser Ser Gly Cys Met Gly
1 5 10

<210> SEQ ID NO 25
<211> LENGTH: 10
<212> TYPE: PRT
<213> ORGANISM: Artificial Sequence
<220> FEATURE:
<223> OTHER INFORMATION: CDR1 of 77LICA519 (Kabat)

<400> SEQUENCE: 25

Gly Leu Pro Tyr Thr Gly Tyr Cys Met Gly
1 5 10

<210> SEQ ID NO 26
<211> LENGTH: 10
<212> TYPE: PRT
<213> ORGANISM: Artificial Sequence
<220> FEATURE:
<223> OTHER INFORMATION: CDR1 of 77LICA602 (Kabat)

<400> SEQUENCE: 26

Gly Tyr Thr Ser Ser Tyr Ala Tyr Met Gly
1 5 10

<210> SEQ ID NO 27
<211> LENGTH: 10
<212> TYPE: PRT
<213> ORGANISM: Artificial Sequence
<220> FEATURE:
<223> OTHER INFORMATION: CDR1 of LIC1157 (Kabat)

<400> SEQUENCE: 27

Gly Phe Thr Phe Ser Asp Ala Val Met Ser
1 5 10

<210> SEQ ID NO 28
<211> LENGTH: 10
<212> TYPE: PRT
<213> ORGANISM: Artificial Sequence
<220> FEATURE:
<223> OTHER INFORMATION: CDR1 of LIC1159 (Kabat)

<400> SEQUENCE: 28

Gly Arg Thr Phe Ser Ser Leu Ala Met Gly
1 5 10

<210> SEQ ID NO 29
<211> LENGTH: 17
<212> TYPE: PRT
<213> ORGANISM: Artificial Sequence
<220> FEATURE:
<223> OTHER INFORMATION: CDR2 of VHH-083 (Kabat)

<400> SEQUENCE: 29

Ala Ile Gly Gln Val Thr Gly Arg Ser Tyr Tyr Val Asp Ser Val Lys
1 5 10 15

Gly

<210> SEQ ID NO 30
<211> LENGTH: 16
<212> TYPE: PRT
<213> ORGANISM: Artificial Sequence
<220> FEATURE:
<223> OTHER INFORMATION: CDR2 of VHH-111 (Kabat)

<400> SEQUENCE: 30

Thr Ile Arg Thr Asp His Ala Gly Thr Tyr Ala Asp Ser Val Lys Gly
1 5 10 15

<210> SEQ ID NO 31
<211> LENGTH: 16
<212> TYPE: PRT
<213> ORGANISM: Artificial Sequence
<220> FEATURE:

<223> OTHER INFORMATION: CDR2 of 77LICA542 (Kabat)

<400> SEQUENCE: 31

Ala Ile Asp Ser Asp Gly Met Thr Ser Tyr Ala Asp Ser Val Lys Gly
1 5 10 15

<210> SEQ ID NO 32
<211> LENGTH: 17
<212> TYPE: PRT
<213> ORGANISM: Artificial Sequence
<220> FEATURE:
<223> OTHER INFORMATION: CDR2 of 77LICA519 (Kabat)

<400> SEQUENCE: 32

Ala Ile Ser Thr Gly Ser Gly Gly Thr Asp Tyr Ala Asp Ser Val Lys
1 5 10 15

Gly

<210> SEQ ID NO 33
<211> LENGTH: 16
<212> TYPE: PRT
<213> ORGANISM: Artificial Sequence
<220> FEATURE:
<223> OTHER INFORMATION: CDR2 of 77LICA602 (Kabat)

<400> SEQUENCE: 33

Ala Ile Gly Ser Asn Gly Arg Thr Asn Tyr Ala Asp Ser Val Lys Gly
1 5 10 15

<210> SEQ ID NO 34
<211> LENGTH: 17
<212> TYPE: PRT
<213> ORGANISM: Artificial Sequence
<220> FEATURE:
<223> OTHER INFORMATION: CDR2 of LIC1157 (Kabat)

<400> SEQUENCE: 34

Asp Ile Ser Asn Gly Gly Ile Thr Arg Arg Tyr Ser Asp Ser Val Lys
1 5 10 15

Gly

<210> SEQ ID NO 35
<211> LENGTH: 17
<212> TYPE: PRT
<213> ORGANISM: Artificial Sequence
<220> FEATURE:
<223> OTHER INFORMATION: CDR2 of LIC1159 (Kabat)

<400> SEQUENCE: 35

Ala Ile Ser Trp Ser Gly Gly Ser Ile Tyr Tyr Ala Asp Ser Val Lys
1 5 10 15

Gly

<210> SEQ ID NO 36
<211> LENGTH: 16
<212> TYPE: PRT
<213> ORGANISM: Artificial Sequence
<220> FEATURE:
<223> OTHER INFORMATION: CDR3 of VHH-083 (Kabat) or VHH-131 (Kabat)

<400> SEQUENCE: 36

Ala Pro Gly Cys Leu Leu Ser Ala Leu Arg Ser Ala Asp Tyr Arg Asn
1 5 10 15

-continued

<210> SEQ ID NO 37
<211> LENGTH: 10
<212> TYPE: PRT
<213> ORGANISM: Artificial Sequence
<220> FEATURE:
<223> OTHER INFORMATION: CDR3 of VHH-111 (Kabat)

<400> SEQUENCE: 37

Ser Tyr Ser Gly Ala Thr Thr Phe Arg Tyr
1 5 10

<210> SEQ ID NO 38
<211> LENGTH: 17
<212> TYPE: PRT
<213> ORGANISM: Artificial Sequence
<220> FEATURE:
<223> OTHER INFORMATION: CDR3 of 77LICA542 (Kabat)

<400> SEQUENCE: 38

Asp Pro Asp Cys Tyr Tyr Ser Asp Tyr Ala Ile Ser Pro Ala Phe Gly
1 5 10 15

Tyr

<210> SEQ ID NO 39
<211> LENGTH: 17
<212> TYPE: PRT
<213> ORGANISM: Artificial Sequence
<220> FEATURE:
<223> OTHER INFORMATION: CDR3 of 77LICA519 (Kabat)

<400> SEQUENCE: 39

Gly Leu Arg Leu Pro Gly Arg Ala Cys Thr Thr Ser His Lys Tyr Asn
1 5 10 15

Tyr

<210> SEQ ID NO 40
<211> LENGTH: 17
<212> TYPE: PRT
<213> ORGANISM: Artificial Sequence
<220> FEATURE:
<223> OTHER INFORMATION: CDR3 of 77LICA602 (Kabat)

<400> SEQUENCE: 40

Arg Arg Trp Gly Trp Gly Glu Leu Pro Leu Thr Pro Ser Glu Tyr Asn
1 5 10 15

Asn

<210> SEQ ID NO 41
<211> LENGTH: 7
<212> TYPE: PRT
<213> ORGANISM: Artificial Sequence
<220> FEATURE:
<223> OTHER INFORMATION: CDR3 of LIC1157 (Kabat)

<400> SEQUENCE: 41

Arg Ala Pro Gly Asp Lys Val
1 5

<210> SEQ ID NO 42
<211> LENGTH: 13
<212> TYPE: PRT
<213> ORGANISM: Artificial Sequence
<220> FEATURE:
<223> OTHER INFORMATION: CDR3 of LIC1159 (Kabat)

<400> SEQUENCE: 42

```
Asp Arg Thr Leu Gln Ala Thr Met Ser Glu Ile Ser Tyr
1               5                   10


<210> SEQ ID NO 43
<211> LENGTH: 125
<212> TYPE: PRT
<213> ORGANISM: Artificial Sequence
<220> FEATURE:
<223> OTHER INFORMATION: VHH-083 (amino acid)

<400> SEQUENCE: 43

Gln Val Gln Leu Val Glu Ser Gly Gly Gly Ser Val Gln Ala Gly Gly
1               5                   10                  15

Ser Leu Arg Leu Ser Cys Gly Ala Ser Gly Asn Ile Asn Ser Arg Asn
            20                  25                  30

Cys Met Gly Trp Phe Arg Gln Ala Pro Gly Lys Glu Arg Glu Gly Val
        35                  40                  45

Ala Ala Ile Gly Gln Val Thr Gly Arg Ser Tyr Tyr Val Asp Ser Val
    50                  55                  60

Lys Gly Arg Phe Thr Ile Ser Leu Asp Asn Ala Lys Asn Thr Leu Tyr
65                  70                  75                  80

Leu Gln Met Asn Thr Leu Lys Pro Glu Asp Thr Ala Met Tyr Tyr Cys
                85                  90                  95

Ala Ala Ala Pro Gly Cys Leu Leu Ser Ala Leu Arg Ser Ala Asp Tyr
            100                 105                 110

Arg Asn Trp Gly Gln Gly Thr Gln Val Thr Val Ser Ser
        115                 120                 125


<210> SEQ ID NO 44
<211> LENGTH: 118
<212> TYPE: PRT
<213> ORGANISM: Artificial Sequence
<220> FEATURE:
<223> OTHER INFORMATION: VHH-111 (amino acid)

<400> SEQUENCE: 44

Glu Val Gln Leu Val Glu Ser Gly Gly Gly Ser Val Gln Ala Gly Gly
1               5                   10                  15

Ser Leu Arg Leu Ser Cys Ala Ala Ser Gly Asp Thr Leu Ser Asn Lys
            20                  25                  30

Trp Met Gly Trp Phe Arg Gln Ala Pro Gly Lys Glu Arg Asp Trp Val
        35                  40                  45

Ala Thr Ile Arg Thr Asp His Ala Gly Thr Tyr Ala Asp Ser Val Lys
    50                  55                  60

Gly Arg Phe Thr Ile Ser Arg Asp Asn Phe Lys Asn Met Ile Tyr Leu
65                  70                  75                  80

Gln Met Asn Asn Leu Lys Pro Glu Asp Thr Ala Met Tyr Tyr Cys Ala
                85                  90                  95

Ala Ser Tyr Ser Gly Ala Thr Thr Phe Arg Tyr Trp Gly Gln Gly Thr
            100                 105                 110

Gln Val Thr Val Ser Ser
        115


<210> SEQ ID NO 45
<211> LENGTH: 125
<212> TYPE: PRT
<213> ORGANISM: Artificial Sequence
<220> FEATURE:
<223> OTHER INFORMATION: 77LICA542 (amino acid)
```

<400> SEQUENCE: 45

```
Gln Val Arg Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Gly
            20                  25                  30

Cys Met Gly Trp Phe Arg Gln Ala Pro Ala Lys Glu Arg Glu Gly Val
        35                  40                  45

Ala Ala Ile Asp Ser Asp Gly Met Thr Ser Tyr Ala Asp Ser Val Lys
    50                  55                  60

Gly Arg Phe Thr Ile Ser Lys Asp Asn Ala Lys Asn Thr Leu His Leu
65                  70                  75                  80

Gln Met Asn Ser Leu Lys Pro Glu Asp Thr Ala Met Tyr Tyr Cys Ala
                85                  90                  95

Ala Asp Pro Asp Cys Tyr Tyr Ser Asp Tyr Ala Ile Ser Pro Ala Phe
            100                 105                 110

Gly Tyr Arg Gly Gln Gly Thr Gln Val Thr Val Ser Ser
        115                 120                 125
```

<210> SEQ ID NO 46
<211> LENGTH: 126
<212> TYPE: PRT
<213> ORGANISM: Artificial Sequence
<220> FEATURE:
<223> OTHER INFORMATION: 77LICA519 (amino acid)

<400> SEQUENCE: 46

```
Gln Val Arg Leu Val Glu Ser Gly Gly Gly Ser Val Gln Ala Gly Gly
1               5                   10                  15

Ser Leu Arg Leu Ser Cys Ala Ala Ser Gly Leu Pro Tyr Thr Gly Tyr
            20                  25                  30

Cys Met Gly Trp Phe Arg Gln Ala Pro Gly Lys Glu Arg Glu Gly Val
        35                  40                  45

Ala Ala Ile Ser Thr Gly Ser Gly Gly Thr Asp Tyr Ala Asp Ser Val
    50                  55                  60

Lys Gly Arg Phe Thr Val Ser Lys Asp Asn Ala Gly Asn Thr Met Phe
65                  70                  75                  80

Leu Gln Met Asn Ser Leu Lys Pro Glu Asp Thr Ala Met Tyr Tyr Cys
                85                  90                  95

Ala Ala Gly Leu Arg Leu Pro Gly Arg Ala Cys Thr Thr Ser His Lys
            100                 105                 110

Tyr Asn Tyr Trp Gly Gln Gly Thr Gln Val Thr Val Ser Ser
        115                 120                 125
```

<210> SEQ ID NO 47
<211> LENGTH: 125
<212> TYPE: PRT
<213> ORGANISM: Artificial Sequence
<220> FEATURE:
<223> OTHER INFORMATION: 77LICA602 (amino acid)

<400> SEQUENCE: 47

```
Gln Val His Leu Val Glu Ser Gly Gly Gly Ser Val Gln Ser Gly Gly
1               5                   10                  15

Ser Leu Arg Leu Ser Cys Gly Ala Ser Gly Tyr Thr Ser Ser Tyr Ala
            20                  25                  30

Tyr Met Gly Trp Phe Arg Gln Val Leu Gly Lys Glu Arg Glu Gly Val
        35                  40                  45
```

-continued

```
Ala Ala Ile Gly Ser Asn Gly Arg Thr Asn Tyr Ala Asp Ser Val Lys
    50                  55                  60

Gly Arg Phe Thr Ile Ser Gln Asp Asn Ala Lys Asn Thr Leu Tyr Leu
65                  70                  75                  80

Gln Met Thr Ser Leu Lys Pro Glu Asp Thr Ala Met Tyr Tyr Cys Ala
                85                  90                  95

Ala Arg Arg Trp Gly Trp Gly Glu Leu Pro Leu Thr Pro Ser Glu Tyr
            100                 105                 110

Asn Asn Trp Gly Gln Gly Thr Gln Val Thr Val Ser Ser
        115                 120                 125
```

<210> SEQ ID NO 48
<211> LENGTH: 116
<212> TYPE: PRT
<213> ORGANISM: Artificial Sequence
<220> FEATURE:
<223> OTHER INFORMATION: LIC1157 (amino acid)

<400> SEQUENCE: 48

```
Gln Val Gln Leu Val Glu Ser Gly Gly Gly Leu Val Gln Pro Gly Gly
1               5                   10                  15

Ser Leu Ile Leu Ser Cys Ala Ala Ser Gly Phe Thr Phe Ser Asp Ala
            20                  25                  30

Val Met Ser Trp Val Arg Gln Ala Pro Gly Lys Gly Leu Glu Trp Val
        35                  40                  45

Ser Asp Ile Ser Asn Gly Gly Ile Thr Arg Arg Tyr Ser Asp Ser Val
    50                  55                  60

Lys Gly Arg Phe Thr Ile Ser Arg Asp Asn Ala Lys Asp Thr Leu Phe
65                  70                  75                  80

Leu Gln Met Thr Lys Leu Lys Pro Asp Asp Thr Ala Val Tyr Tyr Cys
                85                  90                  95

Ala Lys Arg Ala Pro Gly Asp Lys Val Arg Gly Gln Gly Thr Gln Val
            100                 105                 110

Thr Val Ser Ser
        115
```

<210> SEQ ID NO 49
<211> LENGTH: 122
<212> TYPE: PRT
<213> ORGANISM: Artificial Sequence
<220> FEATURE:
<223> OTHER INFORMATION: LIC1159 (amino acid)

<400> SEQUENCE: 49

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Ser Leu
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Ile Tyr Tyr Ala Asp Ser Val
    50                  55                  60

Lys Gly Arg Phe Thr Ile Ser Arg Gly Asn Ala Lys Asn Thr Val Tyr
65                  70                  75                  80

Leu Gln Met Asn Ser Leu Ser Pro Glu Asp Thr Ala Val Tyr Tyr Cys
                85                  90                  95

Ala Ala Asp Arg Thr Leu Gln Ala Thr Met Ser Glu Ile Ser Tyr Trp
```

100 105 110

Gly Gln Gly Thr Gln Val Thr Val Ser Ser
115 120

<210> SEQ ID NO 50
<211> LENGTH: 18
<212> TYPE: PRT
<213> ORGANISM: Artificial Sequence
<220> FEATURE:
<223> OTHER INFORMATION: CDR3 of A592H2 (IMGT)

<400> SEQUENCE: 50

Ala Lys Ala Pro Gly Cys Leu Leu Ser Ala Leu Arg Ser Ala Asp Tyr
1 5 10 15

Arg Asn

<210> SEQ ID NO 51
<211> LENGTH: 125
<212> TYPE: PRT
<213> ORGANISM: Artificial Sequence
<220> FEATURE:
<223> OTHER INFORMATION: huVHH-773 (amino acid)

<400> SEQUENCE: 51

Gln Val Gln Leu Val Glu Ser Gly Gly Gly Leu Val Gln Pro Gly Gly
1 5 10 15

Ser Leu Arg Leu Ser Cys Ala Ala Ser Gly Asn Ile Asn Ser Arg Asn
20 25 30

Cys Met Gly Trp Phe Arg Gln Ala Pro Gly Lys Gly Arg Glu Gly Val
35 40 45

Ala Ala Ile Gly Gln Val Thr Gly Arg Ser Tyr Tyr Val Asp Ser Val
50 55 60

Lys Gly Arg Phe Thr Ile Ser Leu Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Ala Pro Gly Cys Leu Leu Ser Ala Leu Arg Ser Ala Asp Tyr
100 105 110

Arg Asn Trp Gly Gln Gly Thr Leu Val Thr Val Ser Ser
115 120 125

<210> SEQ ID NO 52
<211> LENGTH: 125
<212> TYPE: PRT
<213> ORGANISM: Artificial Sequence
<220> FEATURE:
<223> OTHER INFORMATION: huVHH-776 (amino acid)

<400> SEQUENCE: 52

Gln Val Gln Leu Val Glu Ser Gly Gly Gly Val Val Gln Pro Gly Arg
1 5 10 15

Ser Leu Arg Leu Ser Cys Ala Ala Ser Gly Asn Ile Asn Ser Arg Asn
20 25 30

Cys Met Gly Trp Phe Arg Gln Ala Pro Gly Lys Gly Arg Glu Gly Val
35 40 45

Ala Ala Ile Gly Gln Val Thr Gly Arg Ser Tyr Tyr Val Asp Ser Val
50 55 60

Lys Gly Arg Phe Thr Ile Ser Leu Asp Asn Ser Lys Asn Thr Leu Tyr
65 70 75 80

```
Leu Gln Met Asn Ser Leu Arg Ala Glu Asp Thr Ala Val Tyr Tyr Cys
                85                  90                  95

Ala Ala Ala Pro Gly Cys Leu Leu Ser Ala Leu Arg Ser Ala Asp Tyr
            100                 105                 110

Arg Asn Trp Gly Gln Gly Thr Leu Val Thr Val Ser Ser
        115                 120                 125


<210> SEQ ID NO 53
<211> LENGTH: 125
<212> TYPE: PRT
<213> ORGANISM: Artificial Sequence
<220> FEATURE:
<223> OTHER INFORMATION: A592H1 (amino acid)

<400> SEQUENCE: 53

Gln Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Asn Ser Arg Asn
            20                  25                  30

Cys Met Gly Trp Phe Arg Gln Ala Pro Gly Lys Gly Leu Glu Gly Val
        35                  40                  45

Ala Ala Ile Gly Gln Val Thr Gly Arg Ser Tyr Tyr Val Asp Ser Val
    50                  55                  60

Lys Gly Arg Phe Thr Ile Ser Leu Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Pro Gly Cys Leu Leu Ser Ala Leu Arg Ser Ala Asp Tyr
            100                 105                 110

Arg Asn Trp Gly Gln Gly Thr Leu Val Thr Val Ser Ser
        115                 120                 125


<210> SEQ ID NO 54
<211> LENGTH: 125
<212> TYPE: PRT
<213> ORGANISM: Artificial Sequence
<220> FEATURE:
<223> OTHER INFORMATION: A592H2 (amino acid)

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Asn Ile Asn Ser Arg Asn
            20                  25                  30

Cys Met Gly Trp Phe Arg Gln Ala Pro Gly Lys Gly Leu Glu Gly Val
        35                  40                  45

Ala Ala Ile Gly Gln Val Thr Gly Arg Ser Tyr Tyr Val Asp Ser Val
    50                  55                  60

Lys Gly Arg Phe Thr Ile Ser Leu Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Gly Cys Leu Leu Ser Ala Leu Arg Ser Ala Asp Tyr
            100                 105                 110

Arg Asn Trp Gly Gln Gly Thr Leu Val Thr Val Ser Ser
        115                 120                 125


<210> SEQ ID NO 55
```

```
<211> LENGTH: 125
<212> TYPE: PRT
<213> ORGANISM: Artificial Sequence
<220> FEATURE:
<223> OTHER INFORMATION: A592H3 (amino acid)

<400> SEQUENCE: 55

Gln Val Gln Leu Val Glu Ser Gly Gly Gly Ser Val Gln Ala Gly Gly
1               5                   10                  15

Ser Leu Arg Leu Ser Cys Gly Ala Ser Gly Asn Ile Asn Ser Arg Asn
            20                  25                  30

Cys Met Gly Trp Val Arg Gln Ala Pro Gly Lys Gly Leu Glu Trp Val
        35                  40                  45

Ala Ala Ile Gly Gln Val Thr Gly Arg Ser Tyr Tyr Val Asp Ser Val
    50                  55                  60

Lys Gly Arg Phe Thr Ile Ser Leu Asp Asn Ala Lys Asn Thr Leu Tyr
65                  70                  75                  80

Leu Gln Met Asn Thr Leu Lys Pro Glu Asp Thr Ala Met Tyr Tyr Cys
                85                  90                  95

Ala Ala Ala Pro Gly Cys Leu Leu Ser Ala Leu Arg Ser Ala Asp Tyr
            100                 105                 110

Arg Asn Trp Gly Gln Gly Thr Gln Val Thr Val Ser Ser
        115                 120                 125


<210> SEQ ID NO 56
<211> LENGTH: 125
<212> TYPE: PRT
<213> ORGANISM: Artificial Sequence
<220> FEATURE:
<223> OTHER INFORMATION: A593H4 (amino acid)

<400> SEQUENCE: 56

Gln Val Gln Leu Val Glu Ser Gly Gly Gly Ser Val Gln Ala Gly Gly
1               5                   10                  15

Ser Leu Arg Leu Ser Cys Ser Ala Ser Gly Asn Ile Asn Ser Arg Asn
            20                  25                  30

Cys Met Gly Trp Val Arg Gln Ala Pro Gly Lys Gly Leu Glu Trp Val
        35                  40                  45

Ala Ala Ile Gly Gln Val Thr Gly Arg Ser Tyr Tyr Val Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Cys Leu Leu Ser Ala Leu Arg Ser Ala Asp Tyr
            100                 105                 110

Arg Asn Trp Gly Gln Gly Thr Gln Val Thr Val Ser Ser
        115                 120                 125


<210> SEQ ID NO 57
<211> LENGTH: 371
<212> TYPE: PRT
<213> ORGANISM: Artificial Sequence
<220> FEATURE:
<223> OTHER INFORMATION: VHH-083-CAR (amino acid)

<400> SEQUENCE: 57

Met Ala Leu Pro Val Thr Ala Leu Leu Leu Pro Leu Ala Leu Leu Leu
1               5                   10                  15
```

```
His Ala Ala Arg Pro Gln Val Gln Leu Val Glu Ser Gly Gly Gly Ser
            20                  25                  30

Val Gln Ala Gly Gly Ser Leu Arg Leu Ser Cys Gly Ala Ser Gly Asn
        35                  40                  45

Ile Asn Ser Arg Asn Cys Met Gly Trp Phe Arg Gln Ala Pro Gly Lys
    50                  55                  60

Glu Arg Glu Gly Val Ala Ala Ile Gly Gln Val Thr Gly Arg Ser Tyr
65                  70                  75                  80

Tyr Val Asp Ser Val Lys Gly Arg Phe Thr Ile Ser Leu Asp Asn Ala
                85                  90                  95

Lys Asn Thr Leu Tyr Leu Gln Met Asn Thr Leu Lys Pro Glu Asp Thr
            100                 105                 110

Ala Met Tyr Tyr Cys Ala Ala Ala Pro Gly Cys Leu Leu Ser Ala Leu
        115                 120                 125

Arg Ser Ala Asp Tyr Arg Asn Trp Gly Gln Gly Thr Gln Val Thr Val
    130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370
```

<210> SEQ ID NO 58
<211> LENGTH: 359
<212> TYPE: PRT
<213> ORGANISM: Artificial Sequence
<220> FEATURE:
<223> OTHER INFORMATION: VHH-111-CAR (amino acid)

<400> SEQUENCE: 58

-continued

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Ser
20 25 30

Val Gln Ala Gly Gly Ser Leu Arg Leu Ser Cys Ala Ala Ser Gly Asp
35 40 45

Thr Leu Ser Asn Lys Trp Met Gly Trp Phe Arg Gln Ala Pro Gly Lys
50 55 60

Glu Arg Asp Trp Val Ala Thr Ile Arg Thr Asp His Ala Gly Thr Tyr
65 70 75 80

Ala Asp Ser Val Lys Gly Arg Phe Thr Ile Ser Arg Asp Asn Phe Lys
85 90 95

Asn Met Ile Tyr Leu Gln Met Asn Asn Leu Lys Pro Glu Asp Thr Ala
100 105 110

Met Tyr Tyr Cys Ala Ala Ser Tyr Ser Gly Ala Thr Thr Phe Arg Tyr
115 120 125

Trp Gly Gln Gly Thr Gln Val Thr Val Ser Ser Thr Ser Thr Thr Thr
130 135 140

Pro Ala Pro Arg Pro Pro Thr Pro Ala Pro Thr Ile Ala Ser Gln Pro
145 150 155 160

Leu Ser Leu Arg Pro Glu Ala Cys Arg Pro Ala Ala Gly Gly Ala Val
165 170 175

His Thr Arg Gly Leu Asp Phe Ala Cys Asp Ile Tyr Ile Trp Ala Pro
180 185 190

Leu Ala Gly Thr Cys Gly Val Leu Leu Leu Ser Leu Val Ile Thr Leu
195 200 205

Tyr Cys Lys Arg Gly Arg Lys Lys Leu Leu Tyr Ile Phe Lys Gln Pro
210 215 220

Phe Met Arg Pro Val Gln Thr Thr Gln Glu Glu Asp Gly Cys Ser Cys
225 230 235 240

Arg Phe Pro Glu Glu Glu Glu Gly Gly Cys Glu Leu Arg Val Lys Phe
245 250 255

Ser Arg Ser Ala Asp Ala Pro Ala Tyr Gln Gln Gly Gln Asn Gln Leu
260 265 270

Tyr Asn Glu Leu Asn Leu Gly Arg Arg Glu Glu Tyr Asp Val Leu Asp
275 280 285

Lys Arg Arg Gly Arg Asp Pro Glu Met Gly Gly Lys Pro Arg Arg Lys
290 295 300

Asn Pro Gln Glu Gly Leu Tyr Asn Glu Leu Gln Lys Asp Lys Met Ala
305 310 315 320

Glu Ala Tyr Ser Glu Ile Gly Met Lys Gly Glu Arg Arg Arg Gly Lys
325 330 335

Gly His Asp Gly Leu Tyr Gln Gly Leu Ser Thr Ala Thr Lys Asp Thr
340 345 350

Tyr Asp Ala Leu His Met Gln
355

<210> SEQ ID NO 59
<211> LENGTH: 371
<212> TYPE: PRT
<213> ORGANISM: Artificial Sequence
<220> FEATURE:
<223> OTHER INFORMATION: 77LICA542-CAR (amino acid)

<400> SEQUENCE: 59

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Tyr Ser Ser Gly Cys Met Gly Trp Phe Arg Gln Ala Pro Ala Lys
    50                  55                  60

Glu Arg Glu Gly Val Ala Ala Ile Asp Ser Asp Gly Met Thr Ser Tyr
65                  70                  75                  80

Ala Asp Ser Val Lys Gly Arg Phe Thr Ile Ser Lys Asp Asn Ala Lys
                85                  90                  95

Asn Thr Leu His Leu Gln Met Asn Ser Leu Lys Pro Glu Asp Thr Ala
            100                 105                 110

Met Tyr Tyr Cys Ala Ala Asp Pro Asp Cys Tyr Tyr Ser Asp Tyr Ala
        115                 120                 125

Ile Ser Pro Ala Phe Gly Tyr Arg Gly Gln Gly Thr Gln Val Thr Val
    130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370
```

```
<210> SEQ ID NO 60
<211> LENGTH: 372
<212> TYPE: PRT
<213> ORGANISM: Artificial Sequence
<220> FEATURE:
<223> OTHER INFORMATION: 77LICA519-CAR (amino acid)
```

-continued

<400> SEQUENCE: 60

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Arg Leu Ser Cys Ala Ala Ser Gly Leu
        35                  40                  45

Pro Tyr Thr Gly Tyr Cys Met Gly Trp Phe Arg Gln Ala Pro Gly Lys
    50                  55                  60

Glu Arg Glu Gly Val Ala Ala Ile Ser Thr Gly Ser Gly Gly Thr Asp
65                  70                  75                  80

Tyr Ala Asp Ser Val Lys Gly Arg Phe Thr Val Ser Lys Asp Asn Ala
                85                  90                  95

Gly Asn Thr Met Phe Leu Gln Met Asn Ser Leu Lys Pro Glu Asp Thr
            100                 105                 110

Ala Met Tyr Tyr Cys Ala Ala Gly Leu Arg Leu Pro Gly Arg Ala Cys
        115                 120                 125

Thr Thr Ser His Lys Tyr Asn Tyr Trp Gly Gln Gly Thr Gln Val Thr
    130                 135                 140

Val Ser Ser Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Ile Tyr Ile Trp Ala Pro Leu Ala Gly Thr Cys Gly Val Leu
        195                 200                 205

Leu Leu Ser Leu Val Ile Thr Leu Tyr Cys Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
            260                 265                 270

Tyr Gln Gln Gly Gln Asn Gln Leu Tyr Asn Glu Leu Asn Leu Gly Arg
        275                 280                 285

Arg Glu Glu Tyr Asp Val Leu Asp Lys Arg Arg Gly Arg Asp Pro Glu
    290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
            340                 345                 350

Leu Ser Thr Ala Thr Lys Asp Thr Tyr Asp Ala Leu His Met Gln Ala
        355                 360                 365

Leu Pro Pro Arg
    370
```

<210> SEQ ID NO 61
<211> LENGTH: 371
<212> TYPE: PRT

```
<213> ORGANISM: Artificial Sequence
<220> FEATURE:
<223> OTHER INFORMATION: 77LICA602-CAR (amino acid)

<400> SEQUENCE: 61

Met Ala Leu Pro Val Thr Ala Leu Leu Leu Pro Leu Ala Leu Leu Leu
1               5                   10                  15

His Ala Ala Arg Pro Gln Val His Leu Val Glu Ser Gly Gly Gly Ser
            20                  25                  30

Val Gln Ser Gly Gly Ser Leu Arg Leu Ser Cys Gly Ala Ser Gly Tyr
        35                  40                  45

Thr Ser Ser Tyr Ala Tyr Met Gly Trp Phe Arg Gln Val Leu Gly Lys
    50                  55                  60

Glu Arg Glu Gly Val Ala Ala Ile Gly Ser Asn Gly Arg Thr Asn Tyr
65                  70                  75                  80

Ala Asp Ser Val Lys Gly Arg Phe Thr Ile Ser Gln Asp Asn Ala Lys
                85                  90                  95

Asn Thr Leu Tyr Leu Gln Met Thr Ser Leu Lys Pro Glu Asp Thr Ala
            100                 105                 110

Met Tyr Tyr Cys Ala Ala Arg Arg Trp Gly Trp Gly Glu Leu Pro Leu
        115                 120                 125

Thr Pro Ser Glu Tyr Asn Asn Trp Gly Gln Gly Thr Gln Val Thr Val
    130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370
```

```
<210> SEQ ID NO 62
<211> LENGTH: 371
<212> TYPE: PRT
<213> ORGANISM: Artificial Sequence
<220> FEATURE:
<223> OTHER INFORMATION: huVHH-773 CAR (amino acid)

<400> SEQUENCE: 62

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Asn
        35                  40                  45

Ile Asn Ser Arg Asn Cys Met Gly Trp Phe Arg Gln Ala Pro Gly Lys
    50                  55                  60

Gly Arg Glu Gly Val Ala Ala Ile Gly Gln Val Thr Gly Arg Ser Tyr
65                  70                  75                  80

Tyr Val Asp Ser Val Lys Gly Arg Phe Thr Ile Ser Leu Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Ala Ala Pro Gly Cys Leu Leu Ser Ala Leu
        115                 120                 125

Arg Ser Ala Asp Tyr Arg Asn Trp Gly Gln Gly Thr Leu Val Thr Val
    130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
```

370

<210> SEQ ID NO 63
<211> LENGTH: 371
<212> TYPE: PRT
<213> ORGANISM: Artificial Sequence
<220> FEATURE:
<223> OTHER INFORMATION: huVHH-776 CAR (amino acid)

<400> SEQUENCE: 63

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Asn
        35                  40                  45

Ile Asn Ser Arg Asn Cys Met Gly Trp Phe Arg Gln Ala Pro Gly Lys
    50                  55                  60

Gly Arg Glu Gly Val Ala Ala Ile Gly Gln Val Thr Gly Arg Ser Tyr
65                  70                  75                  80

Tyr Val Asp Ser Val Lys Gly Arg Phe Thr Ile Ser Leu Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Ala Ala Pro Gly Cys Leu Leu Ser Ala Leu
        115                 120                 125

Arg Ser Ala Asp Tyr Arg Asn Trp Gly Gln Gly Thr Leu Val Thr Val
    130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
```

-continued 355 360 365

Pro Pro Arg
370

<210> SEQ ID NO 64
<211> LENGTH: 375
<212> TYPE: DNA
<213> ORGANISM: Artificial Sequence
<220> FEATURE:
<223> OTHER INFORMATION: VHH-083 (nucleic acid)

<400> SEQUENCE: 64
caggtgcagc tggtggagag cggaggtggc tctgtgcagg ctggtgggtc gctcaggctg 60
tcatgcgggg cgtccggcaa cattaactcc cgcaactgca tgggctggtt ccgtcaagcc 120
ccaggcaagg agcgcgaggg cgtagccgct atcggtcagg tcaccggccg cagctactac 180
gtggattctg ttaaaggccg cttcaccatc tcgttggaca acgcgaagaa cacgctgtac 240
ctgcagatga acacactgaa gcccgaagac accgccatgt attactgtgc tgcagccccg 300
gggtgtctgc tgtccgctct gcgctccgcg gactaccgga attggggcca gggcacccag 360
gtcaccgtgt ccagt 375

<210> SEQ ID NO 65
<211> LENGTH: 354
<212> TYPE: DNA
<213> ORGANISM: Artificial Sequence
<220> FEATURE:
<223> OTHER INFORMATION: VHH-111 (nucleic acid)

<400> SEQUENCE: 65
gaggtgcagc tggtggagag cggaggggga tccgtgcaag ccggcggctc cttgcgcctg 60
tcatgcgccg cttccggtga tactcttagc aacaaatgga tgggctggtt ccgccaggcc 120
cccggcaagg agcgcgattg ggtcgcgacg attcgtaccg accacgccgg gacctacgcg 180
gacagtgtga agggccgctt caccatctcg cgggacaact ttaagaatat gatctacctg 240
cagatgaaca acctgaagcc tgaagacacc gccatgtatt actgtgctgc tagctactcc 300
ggtgcaacca ccttcagata ctggggccag ggcacccagg tcaccgtttc ttct 354

<210> SEQ ID NO 66
<211> LENGTH: 375
<212> TYPE: DNA
<213> ORGANISM: Artificial Sequence
<220> FEATURE:
<223> OTHER INFORMATION: huVHH-773 (nucleic acid)

<400> SEQUENCE: 66
caggtgcagc tggtggagag cggaggcggg ctggtgcagc cgggcggctc cctccgcctg 60
tcatgcgccg cttccggcaa cattaattcc cgcaactgca tgggctggtt ccgccaggcc 120
cccggcaagg gcagggaggg cgtggcggcc atcggtcagg tcaccggccg cagctattac 180
gtggattctg tgaagggacg cttcaccatc tctctggaca actccaagaa cacgctgtac 240
ctgcagatga acagcctgcg cgccgaggac accgccgtgt actactgtgc cgcggcgcca 300
gggtgcctgc tgtccgccct gcgctcggcg gactacagga actggggcca gggcaccctg 360
gttaccgtgt cctcc 375

<210> SEQ ID NO 67
<211> LENGTH: 375
<212> TYPE: DNA

<213> ORGANISM: Artificial Sequence
<220> FEATURE:
<223> OTHER INFORMATION: huVHH-776 (nucleic acid)

<400> SEQUENCE: 67
caggtgcagc tggtggagag cggaggcggt gtggtgcagc cagggcgatc tcttcgcctg 60
tcatgcgccg cttccggcaa cattaattcc cgcaactgca tgggctggtt ccgccaggcc 120
cccggcaaag gcagggaggg cgtggcggcc atcggtcagg tcaccggccg cagctattac 180
gtggattctg tgaagggccg cttcaccatc tctctggaca actccaagaa cacgctgtac 240
ctgcagatga acagcctgcg cgccgaggac accgccgtgt actactgtgc tgcggctccc 300
gggtgcctgc tgtccgccct gcgctcggcg gactaccgga actggggcca gggcaccctg 360
gtgaccgtgt cctcc 375

<210> SEQ ID NO 68
<211> LENGTH: 1116
<212> TYPE: DNA
<213> ORGANISM: Artificial Sequence
<220> FEATURE:
<223> OTHER INFORMATION: VHH-083 CAR (nucleic acid)

<400> SEQUENCE: 68
atggcccttc ctgtgactgc gcttctgctg cccttggcac tcctactcca cgccgcccga 60
cctcaggtgc agctggtgga gagcggaggt ggctctgtgc aggctggtgg gtcgctcagg 120
ctgtcatgcg gggcgtccgg caacattaac tcccgcaact gcatgggctg gttccgtcaa 180
gccccaggca aggagcgcga gggcgtagcc gctatcggtc aggtcaccgg ccgcagctac 240
tacgtggatt ctgttaaagg ccgcttcacc atctcgttgg acaacgcgaa gaacacgctg 300
tacctgcaga tgaacacact gaagcccgaa gacaccgcca tgtattactg tgctgcagcc 360
ccggggtgtc tgctgtccgc tctgcgctcc gcggactacc ggaattgggg ccagggcacc 420
caggtcaccg tgtccagtac tagtaccacg acgccagcgc cgcgaccacc aacaccggcg 480
cccaccatcg cgtcgcagcc cctgtccctg cgcccagagg cgtgccggcc agcggcgggg 540
ggcgcagtgc acacgagggg gctggacttc gcctgtgata tctacatctg ggcgcccttg 600
gccgggactt gtggggtcct tctcctgtca ctggttatca ccctttactg caaacggggc 660
agaaagaaac tcctgtatat attcaaacaa ccatttatga gaccagtaca aactactcaa 720
gaggaagatg gctgtagctg ccgatttcca gaagaagaag aaggaggatg tgaactgaga 780
gtgaagttca gcaggagcgc agacgccccc gcgtaccagc agggccagaa ccagctctat 840
aacgagctca atctaggacg aagagaggag tacgatgttt tggacaagag acgtggccgg 900
gaccctgaga tggggggaaa gccgagaagg aagaaccctc aggaaggcct gtacaatgaa 960
ctgcagaaag ataagatggc ggaggcctac agtgagattg ggatgaaagg cgagcgccgg 1020
aggggcaagg ggcacgatgg cctttaccag ggtctcagta cagccaccaa ggacacctac 1080
gacgcccttc acatgcaggc cctgccccct cgctaa 1116

<210> SEQ ID NO 69
<211> LENGTH: 1095
<212> TYPE: DNA
<213> ORGANISM: Artificial Sequence
<220> FEATURE:
<223> OTHER INFORMATION: VHH-111 CAR (nucleic acid)

<400> SEQUENCE: 69
atggcgctgc cggtgactgc tctactgctg cccctggcgc tcctcttgca tgcagccagg 60

```
ccagaggtgc agctggtgga gagcggaggg ggatccgtgc aagccggcgg ctccttgcgc    120
ctgtcatgcg ccgcttccgg tgatactctt agcaacaaat ggatgggctg gttccgccag    180
gcccccggca aggagcgcga ttgggtcgcg acgattcgta ccgaccacgc cgggacctac    240
gcggacagtg tgaagggccg cttcaccatc tcgcgggaca actttaagaa tatgatctac    300
ctgcagatga acaacctgaa gcctgaagac accgccatgt attactgtgc tgctagctac    360
tccggtgcaa ccaccttcag atactggggc cagggcaccc aggtcaccgt ttcttctact    420
agtaccacga cgccagcgcc gcgaccacca acaccggcgc ccaccatcgc gtcgcagccc    480
ctgtccctgc gcccagaggc gtgccggcca gcggcggggg gcgcagtgca cacgaggggg    540
ctggacttcg cctgtgatat ctacatctgg gcgcccttgg ccgggacttg tggggtcctt    600
ctcctgtcac tggttatcac cctttactgc aaacggggca gaaagaaact cctgtatata    660
ttcaaacaac catttatgag accagtacaa actactcaag aggaagatgg ctgtagctgc    720
cgatttccag aagaagaaga aggaggatgt gaactgagag tgaagttcag caggagcgca    780
gacgcccccg cgtaccagca gggccagaac cagctctata acgagctcaa tctaggacga    840
agagaggagt acgatgtttt ggacaagaga cgtggccggg accctgagat ggggggaaag    900
ccgagaagga agaaccctca ggaaggcctg tacaatgaac tgcagaaaga taagatggcg    960
gaggcctaca gtgagattgg gatgaaaggc gagcgccgga ggggcaaggg gcacgatggc   1020
ctttaccagg gtctcagtac agccaccaag gacacctacg acgcccttca catgcaggcc   1080
ctgccccctc gctaa                                                    1095
```

<210> SEQ ID NO 70
<211> LENGTH: 1116
<212> TYPE: DNA
<213> ORGANISM: Artificial Sequence
<220> FEATURE:
<223> OTHER INFORMATION: huVHH-773 CAR (nucleic acid)

<400> SEQUENCE: 70

```
atggcgctgc ccgtcactgc tctgctcttg cccctggccc tgctgcttca cgccgccagg     60
cctcaggtgc agctggtgga gagcggaggc gggctggtgc agccgggcgg ctccctccgc    120
ctgtcatgcg ccgcttccgg caacattaat tcccgcaact gcatgggctg gttccgccag    180
gcccccggca agggcaggga gggcgtggcg gccatcggtc aggtcaccgg ccgcagctat    240
tacgtggatt ctgtgaaggg acgcttcacc atctctctgg acaactccaa gaacacgctg    300
tacctgcaga tgaacagcct gcgcgccgag gacaccgccg tgtactactg tgccgcggcg    360
ccagggtgcc tgctgtccgc cctgcgctcg gcggactaca ggaactgggg ccagggcacc    420
ctggttaccg tgtcctccac tagtaccacg acgccagcgc cgcgaccacc aacaccggcg    480
cccaccatcg cgtcgcagcc cctgtccctg cgcccagagg cgtgccggcc agcggcgggg    540
ggcgcagtgc acacgagggg gctggacttc gcctgtgata tctacatctg ggcgcccttg    600
gccgggactt gtggggtcct tctcctgtca ctggttatca ccctttactg caaacggggc    660
agaaagaaac tcctgtatat attcaaacaa ccatttatga gaccagtaca aactactcaa    720
gaggaagatg gctgtagctg ccgatttcca gaagaagaag aaggaggatg tgaactgaga    780
gtgaagttca gcaggagcgc agacgccccc gcgtaccagc agggccagaa ccagctctat    840
aacgagctca atctaggacg aagagaggag tacgatgttt tggacaagag acgtggccgg    900
gaccctgaga tggggggaaa gccgagaagg aagaaccctc aggaaggcct gtacaatgaa    960
```

-continued ctgcagaaag ataagatggc ggaggcctac agtgagattg ggatgaaagg cgagcgccgg 1020
aggggcaagg ggcacgatgg cctttaccag ggtctcagta cagccaccaa ggacacctac 1080
gacgcccttc acatgcaggc cctgccccct cgctaa 1116

<210> SEQ ID NO 71
<211> LENGTH: 1116
<212> TYPE: DNA
<213> ORGANISM: Artificial Sequence
<220> FEATURE:
<223> OTHER INFORMATION: huVHH-776 CAR (nucleic acid)

<400> SEQUENCE: 71
atggcgctcc cggtgactgc tcttctgctg cccctggcgc tgctgctcca cgccgccagg 60
cctcaggtgc agctggtgga gagcggaggc ggtgtggtgc agccagggcg atctcttcgc 120
ctgtcatgcg ccgcttccgg caacattaat tcccgcaact gcatgggctg gttccgccag 180
gcccccggca aaggcaggga gggcgtggcg gccatcggtc aggtcaccgg ccgcagctat 240
tacgtggatt ctgtgaaggg ccgcttcacc atctctctgg acaactccaa gaacacgctg 300
tacctgcaga tgaacagcct gcgcgccgag gacaccgccg tgtactactg tgctgcggct 360
cccgggtgcc tgctgtccgc cctgcgctcg gcggactacc ggaactgggg ccagggcacc 420
ctggtgaccg tgtcctccac tagtaccacg acgccagcgc cgcgaccacc aacaccggcg 480
cccaccatcg cgtcgcagcc cctgtccctg cgcccagagg cgtgccggcc agcggcgggg 540
ggcgcagtgc acacgagggg gctggacttc gcctgtgata tctacatctg ggcgcccttg 600
gccgggactt gtggggtcct tctcctgtca ctggttatca ccctttactg caaacggggc 660
agaaagaaac tcctgtatat attcaaacaa ccatttatga gaccagtaca aactactcaa 720
gaggaagatg gctgtagctg ccgatttcca gaagaagaag aaggaggatg tgaactgaga 780
gtgaagttca gcaggagcgc agacgccccc gcgtaccagc agggccagaa ccagctctat 840
aacgagctca atctaggacg aagagaggag tacgatgttt tggacaagag acgtggccgg 900
gaccctgaga tggggggaaa gccgagaagg aagaaccctc aggaaggcct gtacaatgaa 960
ctgcagaaag ataagatggc ggaggcctac agtgagattg ggatgaaagg cgagcgccgg 1020
aggggcaagg ggcacgatgg cctttaccag ggtctcagta cagccaccaa ggacacctac 1080
gacgcccttc acatgcaggc cctgccccct cgctaa 1116

<210> SEQ ID NO 72
<211> LENGTH: 21
<212> TYPE: PRT
<213> ORGANISM: Artificial Sequence
<220> FEATURE:
<223> OTHER INFORMATION: Signal peptide (CD8Alpha)

<400> SEQUENCE: 72

Met Ala Leu Pro Val Thr Ala Leu Leu Leu Pro Leu Ala Leu Leu Leu
1 5 10 15

His Ala Ala Arg Pro
20

<210> SEQ ID NO 73
<211> LENGTH: 45
<212> TYPE: PRT
<213> ORGANISM: Artificial Sequence
<220> FEATURE:
<223> OTHER INFORMATION: Hinge (CD8Alpha)

<400> SEQUENCE: 73

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 74
<211> LENGTH: 24
<212> TYPE: PRT
<213> ORGANISM: Artificial Sequence
<220> FEATURE:
<223> OTHER INFORMATION: Transmembrane domain (CD8Alpha)

<400> SEQUENCE: 74

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 75
<211> LENGTH: 42
<212> TYPE: PRT
<213> ORGANISM: Artificial Sequence
<220> FEATURE:
<223> OTHER INFORMATION: Co-stimulatory signaling domain (CD137)

<400> SEQUENCE: 75

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 76
<211> LENGTH: 112
<212> TYPE: PRT
<213> ORGANISM: Artificial Sequence
<220> FEATURE:
<223> OTHER INFORMATION: Primary intracellular signaling domain
      (CD3Zeta)

<400> SEQUENCE: 76

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 77

<211> LENGTH: 227
<212> TYPE: PRT
<213> ORGANISM: Artificial Sequence
<220> FEATURE:
<223> OTHER INFORMATION: huIgG1Fc

<400> SEQUENCE: 77

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 78
<211> LENGTH: 9
<212> TYPE: DNA
<213> ORGANISM: Artificial Sequence
<220> FEATURE:
<223> OTHER INFORMATION: Kozak sequence

<400> SEQUENCE: 78 gccgccacc 9

<210> SEQ ID NO 79
<211> LENGTH: 2
<212> TYPE: PRT
<213> ORGANISM: Artificial Sequence
<220> FEATURE:
<223> OTHER INFORMATION: Exemplary peptide linker 1
<220> FEATURE:
<221> NAME/KEY: MISC_FEATURE
<222> LOCATION: (1)..(2)
<223> OTHER INFORMATION: can be repeated n times, where n is an integer including, e.g., 1, 2, 3, 4, 5, and 6

<400> SEQUENCE: 79

-continued

```
Gly Ser
1


<210> SEQ ID NO 80
<211> LENGTH: 5
<212> TYPE: PRT
<213> ORGANISM: Artificial Sequence
<220> FEATURE:
<223> OTHER INFORMATION: Exemplary peptide linker 2
<220> FEATURE:
<221> NAME/KEY: MISC_FEATURE
<222> LOCATION: (1)..(5)
<223> OTHER INFORMATION: can be repeated n times, where n is an integer
      including, e.g., 1, 2, 3, 4, 5, and 6

<400> SEQUENCE: 80

Gly Ser Gly Gly Ser
1               5


<210> SEQ ID NO 81
<211> LENGTH: 4
<212> TYPE: PRT
<213> ORGANISM: Artificial Sequence
<220> FEATURE:
<223> OTHER INFORMATION: Exemplary peptide linker 3
<220> FEATURE:
<221> NAME/KEY: MISC_FEATURE
<222> LOCATION: (1)..(4)
<223> OTHER INFORMATION: can be repeated n times, where n is an integer
      including, e.g., 1, 2, 3, 4, 5, and 6

<400> SEQUENCE: 81

Gly Gly Gly Ser
1


<210> SEQ ID NO 82
<211> LENGTH: 34
<212> TYPE: PRT
<213> ORGANISM: Artificial Sequence
<220> FEATURE:
<223> OTHER INFORMATION: Exemplary peptide linker 4

<400> SEQUENCE: 82

Gly Gly Gly Gly Ser Gly Gly Gly Gly Ser Gly Gly Gly Gly Gly Gly
1               5                   10                  15

Ser Gly Ser Gly Gly Gly Gly Ser Gly Gly Gly Gly Ser Gly Gly Gly
            20                  25                  30

Gly Ser


<210> SEQ ID NO 83
<211> LENGTH: 5
<212> TYPE: PRT
<213> ORGANISM: Artificial Sequence
<220> FEATURE:
<223> OTHER INFORMATION: Exemplary peptide linker 5
<220> FEATURE:
<221> NAME/KEY: MISC_FEATURE
<222> LOCATION: (1)..(5)
<223> OTHER INFORMATION: can be repeated n times, where n is an integer
      including, e.g., 1, 2, 3, 4, 5, and 6

<400> SEQUENCE: 83

Gly Gly Gly Gly Ser
1               5


<210> SEQ ID NO 84
<211> LENGTH: 5
```

-continued

<212> TYPE: PRT
<213> ORGANISM: Artificial Sequence
<220> FEATURE:
<223> OTHER INFORMATION: Exemplary peptide linker 6

<400> SEQUENCE: 84

Asp Gly Gly Gly Ser
1 5

<210> SEQ ID NO 85
<211> LENGTH: 5
<212> TYPE: PRT
<213> ORGANISM: Artificial Sequence
<220> FEATURE:
<223> OTHER INFORMATION: Exemplary peptide linker 7

<400> SEQUENCE: 85

Thr Gly Glu Lys Pro
1 5

<210> SEQ ID NO 86
<211> LENGTH: 4
<212> TYPE: PRT
<213> ORGANISM: Artificial Sequence
<220> FEATURE:
<223> OTHER INFORMATION: Exemplary peptide linker 8

<400> SEQUENCE: 86

Gly Gly Arg Arg
1

<210> SEQ ID NO 87
<211> LENGTH: 24
<212> TYPE: PRT
<213> ORGANISM: Artificial Sequence
<220> FEATURE:
<223> OTHER INFORMATION: Exemplary peptide linker 9

<400> SEQUENCE: 87

Gly Gly Gly Gly Ser Gly Gly Gly Gly Ser Gly Gly Gly Gly Gly Gly
1 5 10 15

Ser Gly Ser Gly Gly Gly Gly Ser
20

<210> SEQ ID NO 88
<211> LENGTH: 14
<212> TYPE: PRT
<213> ORGANISM: Artificial Sequence
<220> FEATURE:
<223> OTHER INFORMATION: Exemplary peptide linker 10

<400> SEQUENCE: 88

Glu Gly Lys Ser Ser Gly Ser Gly Ser Glu Ser Lys Val Asp
1 5 10

<210> SEQ ID NO 89
<211> LENGTH: 16
<212> TYPE: PRT
<213> ORGANISM: Artificial Sequence
<220> FEATURE:
<223> OTHER INFORMATION: Exemplary peptide linker 11

<400> SEQUENCE: 89

Lys Glu Ser Gly Ser Val Ser Ser Glu Gln Leu Ala Gln Phe Arg Ser
1 5 10 15

-continued

<210> SEQ ID NO 90
<211> LENGTH: 8
<212> TYPE: PRT
<213> ORGANISM: Artificial Sequence
<220> FEATURE:
<223> OTHER INFORMATION: Exemplary peptide linker 12

<400> SEQUENCE: 90

Gly Gly Arg Arg Gly Gly Gly Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Exemplary peptide linker 13

<400> SEQUENCE: 91

Leu Arg Gln Arg Asp Gly Glu Arg Pro
1               5

<210> SEQ ID NO 92
<211> LENGTH: 12
<212> TYPE: PRT
<213> ORGANISM: Artificial Sequence
<220> FEATURE:
<223> OTHER INFORMATION: Exemplary peptide linker 14

<400> SEQUENCE: 92

Leu Arg Gln Lys Asp Gly Gly Gly Ser Glu Arg Pro
1               5                   10

<210> SEQ ID NO 93
<211> LENGTH: 16
<212> TYPE: PRT
<213> ORGANISM: Artificial Sequence
<220> FEATURE:
<223> OTHER INFORMATION: Exemplary peptide linker 15

<400> SEQUENCE: 93

Leu Arg Gln Lys Asp Gly Gly Gly Ser Gly Gly Gly Ser Glu Arg Pro
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Exemplary peptide linker 16

<400> SEQUENCE: 94

Gly Ser Thr Ser Gly Ser Gly Lys Pro Gly Ser Gly Glu Gly Ser Thr
1               5                   10                  15

<210> SEQ ID NO 95
<211> LENGTH: 14
<212> TYPE: PRT
<213> ORGANISM: Artificial Sequence
<220> FEATURE:
<223> OTHER INFORMATION: Exemplary peptide linker 17

<400> SEQUENCE: 95

Gly Ser Thr Ser Gly Ser Gly Lys Ser Ser Glu Gly Lys Gly
1               5                   10

<210> SEQ ID NO 96

<211> LENGTH: 18
<212> TYPE: PRT
<213> ORGANISM: Artificial Sequence
<220> FEATURE:
<223> OTHER INFORMATION: Exemplary peptide linker 18

<400> SEQUENCE: 96

Lys Glu Ser Gly Ser Val Ser Ser Glu Gln Leu Ala Gln Phe Arg Ser
1               5                   10                  15

Leu Asp

<210> SEQ ID NO 97
<211> LENGTH: 6
<212> TYPE: DNA
<213> ORGANISM: Artificial Sequence
<220> FEATURE:
<223> OTHER INFORMATION: EcoRI restriction site

<400> SEQUENCE: 97 gaattc 6

<210> SEQ ID NO 98
<211> LENGTH: 6
<212> TYPE: DNA
<213> ORGANISM: Artificial Sequence
<220> FEATURE:
<223> OTHER INFORMATION: SpeI restriction site

<400> SEQUENCE: 98 actagt 6

<210> SEQ ID NO 99
<211> LENGTH: 242
<212> TYPE: PRT
<213> ORGANISM: Artificial Sequence
<220> FEATURE:
<223> OTHER INFORMATION: FMC63 scFv

<400> SEQUENCE: 99

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

```
Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser


<210> SEQ ID NO 100
<211> LENGTH: 488
<212> TYPE: PRT
<213> ORGANISM: Artificial Sequence
<220> FEATURE:
<223> OTHER INFORMATION: CD19 scFv CAR

<400> SEQUENCE: 100

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Ser Thr Thr Thr Pro Ala Pro Arg
            260                 265                 270

Pro Pro Thr Pro Ala Pro Thr Ile Ala Ser Gln Pro Leu Ser Leu Arg
        275                 280                 285
```

```
Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485


<210> SEQ ID NO 101
<211> LENGTH: 223
<212> TYPE: PRT
<213> ORGANISM: Artificial Sequence
<220> FEATURE:
<223> OTHER INFORMATION: FMC63 VH-CH1

<400> SEQUENCE: 101

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220


<210> SEQ ID NO 102
<211> LENGTH: 214
<212> TYPE: PRT
<213> ORGANISM: Artificial Sequence
<220> FEATURE:
<223> OTHER INFORMATION: FMC63 VL-CL

<400> SEQUENCE: 102

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 103
<211> LENGTH: 17
<212> TYPE: PRT
<213> ORGANISM: Artificial Sequence
<220> FEATURE:
<223> OTHER INFORMATION: CDR2 of VHH-131 (Kabat)

<400> SEQUENCE: 103

Gly Ile Gly Gln Val Thr Gly Arg Ser Tyr Tyr Ala Asp Ser Val Lys
1               5                   10                  15

Gly
```

<210> SEQ ID NO 104
<211> LENGTH: 125
<212> TYPE: PRT
<213> ORGANISM: Artificial Sequence
<220> FEATURE:
<223> OTHER INFORMATION: VHH-131 (amino acid)

<400> SEQUENCE: 104

```
Gln Val Gln Leu Val Glu Ser Gly Gly Gly Ser Val Gln Ala Gly Gly
1               5                   10                  15

Ser Leu Arg Leu Ser Cys Gly Ala Ser Gly Asn Ile Asn Ser Arg Asn
            20                  25                  30

Cys Met Gly Trp Phe Arg Gln Ala Pro Gly Lys Glu Arg Glu Gly Val
        35                  40                  45

Ala Gly Ile Gly Gln Val Thr Gly Arg Ser Tyr Tyr Ala Asp Ser Val
    50                  55                  60

Lys Gly Arg Phe Thr Ile Ser Leu Asp Asn Ala Lys Asn Met Leu Tyr
65                  70                  75                  80

Leu Gln Met Asn Thr Leu Lys Pro Glu Asp Thr Ala Met Tyr Tyr Cys
                85                  90                  95

Ala Ala Ala Pro Gly Cys Leu Leu Ser Ala Leu Arg Ser Ala Asp Tyr
            100                 105                 110

Arg Asn Trp Gly Gln Gly Thr Gln Val Thr Val Ser Ser
        115                 120                 125
```

<210> SEQ ID NO 105
<211> LENGTH: 371
<212> TYPE: PRT
<213> ORGANISM: Artificial Sequence
<220> FEATURE:
<223> OTHER INFORMATION: VHH-131-CAR (amino acid)

<400> SEQUENCE: 105

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30

Val Gln Ala Gly Gly Ser Leu Arg Leu Ser Cys Gly Ala Ser Gly Asn
        35                  40                  45

Ile Asn Ser Arg Asn Cys Met Gly Trp Phe Arg Gln Ala Pro Gly Lys
    50                  55                  60

Glu Arg Glu Gly Val Ala Gly Ile Gly Gln Val Thr Gly Arg Ser Tyr
65                  70                  75                  80

Tyr Ala Asp Ser Val Lys Gly Arg Phe Thr Ile Ser Leu Asp Asn Ala
                85                  90                  95

Lys Asn Met Leu Tyr Leu Gln Met Asn Thr Leu Lys Pro Glu Asp Thr
            100                 105                 110

Ala Met Tyr Tyr Cys Ala Ala Ala Pro Gly Cys Leu Leu Ser Ala Leu
        115                 120                 125

Arg Ser Ala Asp Tyr Arg Asn Trp Gly Gln Gly Thr Gln Val Thr Val
    130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190
```

```
Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370
```

<210> SEQ ID NO 106
<211> LENGTH: 375
<212> TYPE: DNA
<213> ORGANISM: Artificial Sequence
<220> FEATURE:
<223> OTHER INFORMATION: VHH-131 (nucleic acid)

<400> SEQUENCE: 106

```
caggtgcagc tggtggagag cggaggaggc tccgtgcagg ccggcggctc cctgcgcctg     60

tcatgcgggg cttccggcaa cattaactcc cgcaactgca tgggctggtt ccgccaggcc    120

cccggcaagg agcgcgaggg cgtggctggc atcggtcagg tcaccggccg cagctactac    180

gcggacagcg tgaagggccg cttcaccatc tctctggaca acgccaagaa catgctgtac    240

ctgcagatga acacgctgaa gcctgaagac accgccatgt attactgtgc cgcggctccc    300

gggtgcctgc tgagcgcgct ccgtagtgcg gactacagga attggggcca gggcacccag    360

gtcaccgtgt cgtcc                                                     375
```

<210> SEQ ID NO 107
<211> LENGTH: 1116
<212> TYPE: DNA
<213> ORGANISM: Artificial Sequence
<220> FEATURE:
<223> OTHER INFORMATION: VHH-131 CAR (nucleic acid)

<400> SEQUENCE: 107

```
atggcgctgc cggtgactgc tttgctgctg cccctggccc tgctgctcca cgccgctcgc     60

cctcaggtgc agctggtgga gagcggagga ggctccgtgc aggccggcgg ctccctgcgc    120

ctgtcatgcg gggcttccgg caacattaac tcccgcaact gcatgggctg gttccgccag    180

gcccccggca aggagcgcga gggcgtggct ggcatcggtc aggtcaccgg ccgcagctac    240
```

-continued

```
tacgcggaca gcgtgaaggg ccgcttcacc atctctctgg acaacgccaa gaacatgctg    300

tacctgcaga tgaacacgct gaagcctgaa gacaccgcca tgtattactg tgccgcggct    360

cccgggtgcc tgctgagcgc gctccgtagt gcggactaca ggaattgggg ccagggcacc    420

caggtcaccg tgtcgtccac tagtaccacg acgccagcgc cgcgaccacc aacaccggcg    480

cccaccatcg cgtcgcagcc cctgtccctg cgcccagagg cgtgccggcc agcggcgggg    540

ggcgcagtgc acacgagggg gctggacttc gcctgtgata tctacatctg ggcgcccttg    600

gccgggactt gtggggtcct tctcctgtca ctggttatca ccctttactg caaacggggc    660

agaaagaaac tcctgtatat attcaaacaa ccatttatga gaccagtaca aactactcaa    720

gaggaagatg gctgtagctg ccgatttcca gaagaagaag aaggaggatg tgaactgaga    780

gtgaagttca gcaggagcgc agacgccccc gcgtaccagc agggccagaa ccagctctat    840

aacgagctca atctaggacg aagagaggag tacgatgttt tggacaagag acgtggccgg    900

gaccctgaga tgggggggaaa gccgagaagg aagaaccctc aggaaggcct gtacaatgaa    960

ctgcagaaag ataagatggc ggaggcctac agtgagattg ggatgaaagg cgagcgccgg   1020

aggggcaagg ggcacgatgg cctttaccag ggtctcagta cagccaccaa ggacacctac   1080

gacgcccttc acatgcaggc cctgcccccct cgctaa                            1116
```

<210> SEQ ID NO 108
<211> LENGTH: 5
<212> TYPE: PRT
<213> ORGANISM: Artificial Sequence
<220> FEATURE:
<223> OTHER INFORMATION: CDR1 of VHH-083 & VHH-131 (Kabat with 5aa)

<400> SEQUENCE: 108

Arg Asn Cys Met Gly
1               5

<210> SEQ ID NO 109
<211> LENGTH: 5
<212> TYPE: PRT
<213> ORGANISM: Artificial Sequence
<220> FEATURE:
<223> OTHER INFORMATION: CDR1 of VHH-111 (Kabat with 5aa)

<400> SEQUENCE: 109

Asn Lys Trp Met Gly
1               5

<210> SEQ ID NO 110
<211> LENGTH: 5
<212> TYPE: PRT
<213> ORGANISM: Artificial Sequence
<220> FEATURE:
<223> OTHER INFORMATION: CDR1 of 77LICA542 (Kabat with 5aa)

<400> SEQUENCE: 110

Ser Gly Cys Met Gly
1               5

<210> SEQ ID NO 111
<211> LENGTH: 5
<212> TYPE: PRT
<213> ORGANISM: Artificial Sequence
<220> FEATURE:
<223> OTHER INFORMATION: CDR1 of 77LICA519 (Kabat with 5aa)

<400> SEQUENCE: 111

-continued

```
Gly Tyr Cys Met Gly
1               5


<210> SEQ ID NO 112
<211> LENGTH: 5
<212> TYPE: PRT
<213> ORGANISM: Artificial Sequence
<220> FEATURE:
<223> OTHER INFORMATION: CDR1 of 77LICA602 (Kabat with 5aa)

<400> SEQUENCE: 112

Tyr Ala Tyr Met Gly
1               5


<210> SEQ ID NO 113
<211> LENGTH: 5
<212> TYPE: PRT
<213> ORGANISM: Artificial Sequence
<220> FEATURE:
<223> OTHER INFORMATION: CDR1 of LIC1157 (Kabat with 5aa)

<400> SEQUENCE: 113

Asp Ala Val Met Ser
1               5


<210> SEQ ID NO 114
<211> LENGTH: 5
<212> TYPE: PRT
<213> ORGANISM: Artificial Sequence
<220> FEATURE:
<223> OTHER INFORMATION: CDR1 of LIC1159 (Kabat with 5aa)

<400> SEQUENCE: 114

Ser Leu Ala Met Gly
1               5
```

CD19 BINDING MOLECULES AND USES THEREOF

CROSS REFERENCE

This application is a 371 national stage application of PCT Application No. PCT/CN2021/106892, filed on Jul. 16, 2021, which claims benefit of priority of International Patent Application No. PCT/CN2020/102457 filed on Jul. 16, 2020. The disclosures of the aforementioned applications are hereby incorporated by reference in their entireties.

SEQUENCE LISTING

This application incorporates by reference a Sequence Listing submitted with this application as a text format, entitled "14651-025-228_SEQ_LISTING," created on Jul. 9, 2021 having a size of 85,728 bytes.

1. FIELD

The present disclosure relates to anti-CD19 single domain antibodies, chimeric antigen receptors, engineered immune effector cells, and methods of use thereof. The present disclosure further relates to activation and expansion of cells for therapeutic uses, especially to chimeric antigen receptor-based T cell immunotherapies.

2. BACKGROUND

CD19 is expressed on normal B cells and by cells and tissues of various diseases and conditions, including most B cell malignancies. CD19 is critically involved in establishing intrinsic B cell signaling thresholds through modulating both B cell receptor-dependent and independent signaling. CD19 functions as the dominant signaling component of a multimolecular complex on the surface of mature B cells, and it plays a critical role in maintaining the balance between humoral, antigen-induced response and tolerance induction. See Wang et al., *Exp Hematol Oncol,* 1: 36 (2012).

Various CD19-binding molecules, including anti-CD19 antibodies, and chimeric antigen receptors containing anti-CD19 antibody portions, and cells expressing such chimeric receptors, are available. Chimeric antigen receptor T (CAR-T) cell therapy is an emerging and effective cancer immunotherapy. Especially in hematological malignancies, CAR-T cells have achieved exciting results. Two anti-CD19 scFv based CAR-T therapies have been approved for the treatment of CD19-positive leukemia or lymphoma. However, the application of CAR-T cells is hampered by adverse effects, such as cytokines release syndrome and on-target off-tumor toxicity (Yu et al., *Molecular Cancer* 18 (1): 125 (2019)). Improved CD19-binding molecules and engineered CD19-targeting cells are needed. For example, there is a need to develop stable and small-sized CD19 binding molecules for use in more effective or efficient CAR-T therapies.

3. SUMMARY

In one aspect, provided herein is an anti-CD19 single domain antibody (sdAb) comprising: (i) a CDR1 comprising the amino acid sequence of SEQ ID NO: 1; a CDR2 comprising the amino acid sequence of SEQ ID NO: 8; and a CDR3 comprising the amino acid sequence of SEQ ID NO: 15; (ii) a CDR1 comprising the amino acid sequence of SEQ ID NO: 22 or 108; a CDR2 comprising the amino acid sequence of SEQ ID NO: 29; and a CDR3 comprising the amino acid sequence of SEQ ID NO: 36; (iii) a CDR1 comprising the amino acid sequence of SEQ ID NO: 2; a CDR2 comprising the amino acid sequence of SEQ ID NO: 9; and a CDR3 comprising the amino acid sequence of SEQ ID NO: 16; (iv) a CDR1 comprising the amino acid sequence of SEQ ID NO: 23 or 109; a CDR2 comprising the amino acid sequence of SEQ ID NO: 30; and a CDR3 comprising the amino acid sequence of SEQ ID NO: 37; (v) a CDR1 comprising the amino acid sequence of SEQ ID NO: 3; a CDR2 comprising the amino acid sequence of SEQ ID NO: 10; and a CDR3 comprising the amino acid sequence of SEQ ID NO: 17; (vi) a CDR1 comprising the amino acid sequence of SEQ ID NO: 24 or 110; a CDR2 comprising the amino acid sequence of SEQ ID NO: 31; and a CDR3 comprising the amino acid sequence of SEQ ID NO: 38; (vii) a CDR1 comprising the amino acid sequence of SEQ ID NO: 4; a CDR2 comprising the amino acid sequence of SEQ ID NO: 11; and a CDR3 comprising the amino acid sequence of SEQ ID NO: 18; (viii) a CDR1 comprising the amino acid sequence of SEQ ID NO: 25 or 111; a CDR2 comprising the amino acid sequence of SEQ ID NO: 32; and a CDR3 comprising the amino acid sequence of SEQ ID NO: 39; (ix) a CDR1 comprising the amino acid sequence of SEQ ID NO: 5; a CDR2 comprising the amino acid sequence of SEQ ID NO: 12; and a CDR3 comprising the amino acid sequence of SEQ ID NO: 19; (x) a CDR1 comprising the amino acid sequence of SEQ ID NO: 26 or 112; a CDR2 comprising the amino acid sequence of SEQ ID NO: 33; and a CDR3 comprising the amino acid sequence of SEQ ID NO: 40; (xi) a CDR1 comprising the amino acid sequence of SEQ ID NO: 6; a CDR2 comprising the amino acid sequence of SEQ ID NO: 13; and a CDR3 comprising the amino acid sequence of SEQ ID NO: 20; (xii) a CDR1 comprising the amino acid sequence of SEQ ID NO: 27 or 113; a CDR2 comprising the amino acid sequence of SEQ ID NO: 34; and a CDR3 comprising the amino acid sequence of SEQ ID NO: 41; (xiii) a CDR1 comprising the amino acid sequence of SEQ ID NO: 7; a CDR2 comprising the amino acid sequence of SEQ ID NO: 14; and a CDR3 comprising the amino acid sequence of SEQ ID NO: 21; (xiv) a CDR1 comprising the amino acid sequence of SEQ ID NO: 28 or 114; a CDR2 comprising the amino acid sequence of SEQ ID NO: 35; and a CDR3 comprising the amino acid sequence of SEQ ID NO: 42; or (xv) a CDR1 comprising the amino acid sequence of SEQ ID NO: 1; a CDR2 comprising the amino acid sequence of SEQ ID NO: 8; and a CDR3 comprising the amino acid sequence of SEQ ID NO: 50; or (xvi) a CDR1 comprising the amino acid sequence of SEQ ID NO: 22 or 108; a CDR2 comprising the amino acid sequence of SEQ ID NO: 103; and a CDR3 comprising the amino acid sequence of SEQ ID NO: 36.

In another aspect, provided herein is an anti-CD19 single domain antibody (sdAb) comprising: (i) a CDR1, a CDR2, and a CDR3 having the amino acid sequences of the CDR1, CDR2, and CDR3, respectively, as set forth in SEQ ID NO: 43; (ii) a CDR1, a CDR2, and a CDR3 having the amino acid sequences of the CDR1, CDR2, and CDR3, respectively, as set forth in SEQ ID NO: 44; (iii) a CDR1, a CDR2, and a CDR3 having the amino acid sequences of the CDR1, CDR2, and CDR3, respectively, as set forth in SEQ ID NO: 45; (iv) a CDR1, a CDR2, and a CDR3 having the amino acid sequences of the CDR1, CDR2, and CDR3, respectively, as set forth in SEQ ID NO: 46; (v) a CDR1, a CDR2, and a CDR3 having the amino acid sequences of the CDR1, CDR2, and CDR3, respectively, as set forth in SEQ ID NO:

47; (vi) a CDR1, a CDR2, and a CDR3 having the amino acid sequences of the CDR1, CDR2, and CDR3, respectively, as set forth in SEQ ID NO: 48; (vii) a CDR1, a CDR2, and a CDR3 having the amino acid sequences of the CDR1, CDR2, and CDR3, respectively, as set forth in SEQ ID NO: 49; (viii) a CDR1, a CDR2, and a CDR3 having the amino acid sequences of the CDR1, CDR2, and CDR3, respectively, as set forth in SEQ ID NO: 51; (ix) a CDR1, a CDR2, and a CDR3 having the amino acid sequences of the CDR1, CDR2, and CDR3, respectively, as set forth in SEQ ID NO: 52; (x) a CDR1, a CDR2, and a CDR3 having the amino acid sequences of the CDR1, CDR2, and CDR3, respectively, as set forth in SEQ ID NO: 53; (xi) a CDR1, a CDR2, and a CDR3 having the amino acid sequences of the CDR1, CDR2, and CDR3, respectively, as set forth in SEQ ID NO: 54; (xii) a CDR1, a CDR2, and a CDR3 having the amino acid sequences of the CDR1, CDR2, and CDR3, respectively, as set forth in SEQ ID NO: 55; (xiii) a CDR1, a CDR2, and a CDR3 having the amino acid sequences of the CDR1, CDR2, and CDR3, respectively, as set forth in SEQ ID NO: 56; or (xiv) a CDR1, a CDR2, and a CDR3 having the amino acid sequences of the CDR1, CDR2, and CDR3, respectively, as set forth in SEQ ID NO: 104. In some embodiments, the CDR1, CDR2 or CDR3 are determined according to the Kabat numbering scheme, the IMGT numbering scheme, the AbM numbering scheme, the Chothia numbering scheme, the Contact numbering scheme, or a combination thereof.

In some embodiments, the anti-CD19 sdAb provided herein further comprises one or more FR regions as set forth in SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, and/or SEQ ID NO: 104.

In some embodiments, the anti-CD19 sdAb provided herein comprises the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56 or SEQ ID NO: 104. In certain embodiments, the anti-CD19 sdAb provided herein comprises or consists of an amino acid sequence having at least 75%, 80%, 85%, 90%, 95%, 96%, 97%, 98%, 99%, or more sequence identity with the sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56 or SEQ ID NO: 104.

In some embodiments, the anti-CD19 sdAb provided herein is a llama or camelid sdAb. In other embodiments, the anti-CD19 sdAb provided herein is a humanized sdAb. In certain embodiments, the anti-CD19 sdAb is genetically fused or chemically conjugated to an agent.

In another aspect, provided herein is a chimeric antigen receptor (CAR), comprising: (a) an extracellular antigen binding domain comprising the anti-CD19 sdAb provided herein; (b) a transmembrane domain; and (c) an intracellular signaling domain. In some embodiments, the extracellular antigen binding domain further comprises one or more additional antigen binding domain(s). In some embodiments, the extracellular antigen binding domain further comprises one additional antigen binding domain. In some embodiments, the extracellular antigen binding domain further comprises two additional antigen binding domains. In some embodiments, the one or more additional antigen binding domain(s) bind to one or more antigen(s) selected from a group consisting of CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the transmembrane domain is derived from a molecule selected from a group consisting of CD8a, CD4, CD28, CD137, CD80, CD86, CD152, and PD1. In some specific embodiments, the transmembrane domain is derived from CD8a.

In some embodiments, the intracellular signaling domain comprises a primary intracellular signaling domain of an immune effector cell. In some embodiments, the primary intracellular signaling domain is derived from CD3ζ.

In some embodiments, the intracellular signaling domain further comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some specific embodiments, the co-stimulatory signaling domain is derived from CD137.

In some embodiments, the CAR provided herein further comprises a hinge domain located between the C-terminus of the extracellular antigen binding domain and the N-terminus of the transmembrane domain. In some specific embodiments, the hinge domain is derived from CD8α.

In some embodiments, the CAR provided herein further comprises a signal peptide located at the N-terminus of the polypeptide. In some specific embodiments, the signal peptide is derived from CD8α.

In another aspect, provided herein is a chimeric antigen receptor (CAR), comprising an amino acid sequence selected from the group consisting of SEQ ID NO: 57, SEQ ID NO: 58, SEQ ID NO: 59, SEQ ID NO: 60, SEQ ID NO: 61, SEQ ID NO: 62 SEQ ID NO: 63 and SEQ ID NO: 105. In another aspect, provided herein is an isolated nucleic acid comprising a nucleic acid sequence encoding the anti-CD19 sdAb provided herein.

In another aspect, provided herein is a vector comprising an isolated nucleic acid comprising a nucleic acid sequence encoding the anti-CD19 sdAb provided herein. In yet another aspect, provided herein is an isolated nucleic acid comprising a nucleic acid sequence encoding the CAR provided herein. In yet another aspect, provided herein is a vector comprising an isolated nucleic acid comprising a nucleic acid sequence encoding the CAR provided herein.

In yet another aspect, provided herein is an engineered immune effector cell, comprising the CAR, the isolated nucleic acid, or the vector provided herein. In some embodiments, the immune effector cell is a T cell or a B cell.

In yet another aspect, provided herein is a pharmaceutical composition, comprising the anti-CD19 sdAb, the engineered immune effector cell, or the vector provided herein, and a pharmaceutically acceptable excipient.

In yet another aspect, provided herein is a method of treating a disease or disorder in a subject, comprising administering to the subject an effective amount of the anti-CD19 sdAb, the engineered immune effector cell, or the pharmaceutical composition provided herein. In some embodiments, the disease or disorder is CD19 associated disease or disorder. In some embodiments, the disease or disorder is a B cell associated disease or disorder. In some embodiments, the disease or disorder is cancer. In some embodiments, the disease or disorder is a B cell malignancy. In some embodiments, the B cell malignancy is a B cell leukemia or B cell lymphoma. In some embodiments, the disease or disorder is selected from a group consisting of marginal zone lymphoma (e.g., splenic marginal zone lymphoma), diffuse large B cell lymphoma (DLBCL), mantle cell lymphoma (MCL), primary central nervous system (CNS) lymphoma, primary mediastinal B cell lymphoma (PMBL), small lymphocytic lymphoma (SLL), B cell prolymphocytic leukemia (B-PLL), follicular lymphoma (FL), burkitt lymphoma, primary intraocular lymphoma, chronic lymphocytic leukemia (CLL), acute lymphoblastic leukemia (ALL), hairy cell leukemia (HCL), precursor B lymphoblastic leukemia, non-hodgkin lymphoma (NHL), high-grade B-cell lymphoma (HGBL), and multiple myelomia (MM). In other embodiments, the disease or disorder is an autoimmune and/or inflammatory disease. In some embodiments, the autoimmune and/or inflammatory disease is associated with inappropriate or enhanced B cell numbers and/or activation.

4. BRIEF DESCRIPTION OF THE FIGURES

5. DETAILED DESCRIPTION

Figure 1A:
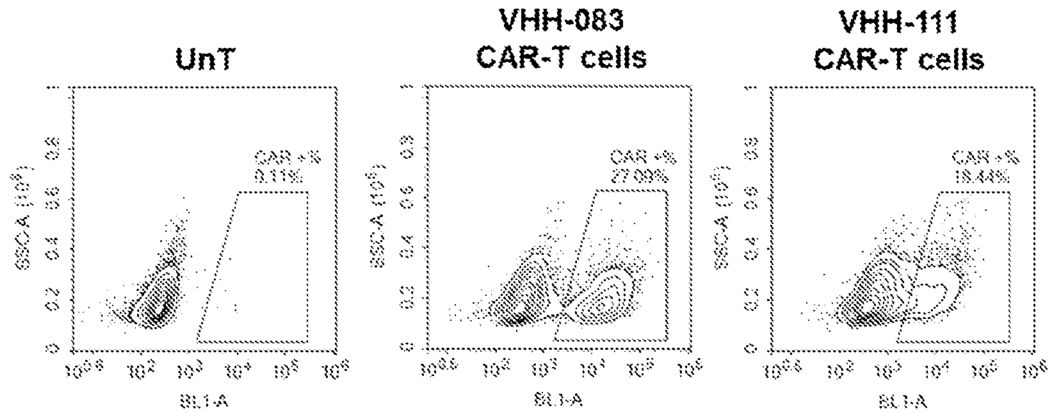
FIGS. 1A-1C show the transduction efficiency of VHH-based CAR-T cells (FIGS. 1A and 1B) and scFv-based CAR-T cells (FIG. 1C). UnT refers to T cells un-transduced with CAR.

The present disclosure is based in part on the novel single domain antibodies (e.g., VHH domains) that bind to CD19, chimeric antigen receptors or engineered cells comprising same, and improved properties thereof.

5.1. Definitions

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: *Methods and Protocols* (Albitar ed. 2010); and *Antibody Engineering* Vols 1 and 2 (Kontermann and Ditbel eds., 2d ed. 2010). Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "antibody," "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof (e.g., domain antibodies), as described below. An antibody can be human, humanized, chimeric and/or affinity matured, as well as an antibody from other species, for example, mouse, rabbit, llama, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See. e.g., *Antibody Engineering* (Borrebaeck ed., 2d ed. 1995); and Kuby, *Immunology* (3d ed. 1997). Antibodies also include, but are not limited to, synthetic antibodies, recombinantly produced antibodies, single domain antibodies including from Camelidae species (e.g., llama or alpaca) or their humanized variants, intrabodies, anti-idiotypic (anti-Id) antibodies, and functional fragments (e.g., antigen-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments) include single-chain Fvs (scFv) (e.g., including monospecific, bispecific, etc.), Fab fragments, F(ab') fragments, $F(ab)_2$ fragments, $F(ab')_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies. Antibodies may be neither agonistic nor antagonistic.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

"Single domain antibody" or "sdAb" as used herein refers to a single monomeric variable antibody domain and which is capable of antigen binding (e.g., single domain antibodies that bind to CD19). Single domain antibodies include VHH domains as described herein. Examples of single domain antibodies include, but are not limited to, antibodies naturally devoid of light chains such as those from Camelidae species (e.g., llama), single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, and bovine. For example, a single domain antibody can be derived from antibodies raised in Camelidae species, for example in camel, llama, dromedary, alpaca and guanaco, as described herein. Other species besides Camelidae may produce heavy chain antibodies naturally devoid of light chain; VHHs derived from such other species are within the scope of the disclosure. In some embodiments, the single domain antibody (e.g., VHH) provided herein has a structure of FR1-CDR1-FR2-CDR2-FR3-CDR3-FR4. Single domain antibodies may be genetically fused or chemically conjugated to another molecule (e.g., an agent) as described herein. Single domain antibodies may be part of a bigger binding molecule (e.g., a multispecific antibody or a chimeric antigen receptor).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the binding molecules described herein terms such as "bind to," "that specifically bind to," and analogous terms are also used interchangeably herein and refer to binding molecules of antigen binding domains that specifically bind to an antigen, such as a polypeptide. A binding molecule or antigen binding domain that binds to or specifically binds to an antigen can be identified, for example, by immunoassays, Octet®, Biacore®, or other techniques known to those of skill in the art. In some embodiments, a binding molecule or antigen binding domain binds to or specifically binds to an antigen when it binds to an antigen with higher affinity than to any cross-reactive antigen as determined using experimental techniques, such as radioimmunoassay (RIA) and enzyme linked immunosorbent assay (ELISA). Typically, a specific or selective reaction will be at least twice background signal or noise and may be more than 10 times background. See, e.g., *Fundamental Immunology* 332-36 (Paul ed., 2d ed. 1989) for a discussion regarding binding specificity. In certain embodiments, the extent of binding of a binding molecule or antigen binding domain to a "non-target" protein is less than about 10% of the binding of the binding molecule or antigen binding domain to its particular target antigen, for example, as determined by fluorescence activated cell sorting (FACS) analysis or RIA. A binding molecule or antigen binding domain that binds to an antigen includes one that is capable of binding the antigen with sufficient affinity such that the binding molecule is useful, for example, as a therapeutic and/or diagnostic agent in targeting the antigen. In certain embodiments, a binding molecule or antigen binding domain that binds to an antigen has a dissociation constant ($K_D$) of less than or equal to 1 μM, 800 nM, 600 nM, 550 nM, 500 nM, 300 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, a binding molecule or antigen binding domain binds to an epitope of an antigen that is conserved among the antigen from different species.

In certain embodiments, the binding molecules or antigen binding domains can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55). Chimeric sequences may include humanized sequences.

In certain embodiments, the binding molecules or antigen binding domains can comprise portions of "humanized" forms of nonhuman (e.g., camelid, murine, non-human primate) antibodies that include sequences from human immunoglobulins (e.g., recipient antibody) in which the native CDR residues are replaced by residues from the corresponding CDR of a nonhuman species (e.g., donor antibody) such as camelid, mouse, rat, rabbit, or nonhuman primate having the desired specificity, affinity, and capacity. In some instances, one or more FR region residues of the human immunoglobulin sequences are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature 321: 522-25 (1986); Riechmann et al., Nature 332:323-29 (1988); Presta, Curr. Op. Struct. Biol. 2:593-96 (1992); Carter et al., Proc. Natl. Acad. Sci. USA 89:4285-89 (1992); U.S. Pat. Nos. 6,800,738; 6,719,971; 6,639,055; 6,407,213; and 6,054,297.

In certain embodiments, the binding molecules or antigen binding domains can comprise portions of a "fully human antibody" or "human antibody," wherein the terms are used interchangeably herein and refer to an antibody that comprises a human variable region and, for example, a human constant region. The binding molecules may comprise a single domain antibody sequence. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies having variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, J. Mol. Biol. 227:381 (1991); Marks et al., J. Mol. Biol. 222:581 (1991)) and yeast display libraries (Chao et al., Nature Protocols 1: 755-68 (2006)). Also available for the preparation of human monoclonal antibodies are methods described in Cole et al., *Monoclonal Antibodies and Cancer Therapy* 77 (1985); Boemer et al., J. Immunol. 147(1):86-95 (1991); and van Dijk and van de Winkel, Curr. Opin. Pharmacol. 5: 368-74 (2001). Human antibodies can be prepared by administering the antigen to a transgenic animal that has been modified to produce such antibodies in response to antigenic challenge, but whose endogenous loci have been disabled, e.g., mice (see. e.g., Jakobovits, Curr. Opin. Biotechnol. 6(5):561-66 (1995); Brüggemann and Taussing, Curr. Opin. Biotechnol. 8(4):455-58 (1997); and U.S. Pat. Nos. 6,075,181 and 6,150,584 regarding XENOMOUSE™ technology). See also, for example, Li et al., Proc. Natl. Acad. Sci. USA 103:3557-62 (2006) regarding human antibodies generated via a human B-cell hybridoma technology.

In certain embodiments, the binding molecules or antigen binding domains can comprise portions of a "recombinant human antibody," wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al., *Nucl. Acids Res.* 20:6287-6295 (1992)) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the binding molecules or antigen binding domains can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts or well-known post-translational modifications such as amino acid isomerization or deamidation, methionine oxidation or asparagine or glutamine deamidation, each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., Nature 256:495 (1975), or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., Nature 352:624-28 (1991) and Marks et al., J. Mol. Biol. 222:581-97 (1991), for example. Other methods for the preparation of clonal cell lines and of monoclonal antibodies expressed thereby are well known in the art. See, e.g., *Short Protocols in Molecular Biology* (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for p and F isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994); and *Immunobiology* (Janeway et al. eds., $5^{th}$ ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see. e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region," "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences.

CDR regions are well known to those skilled in the art and have been defined by well-known numbering systems. For example, the Kabat Complementarity Determining Regions (CDRs) are based on sequence variability and are the most commonly used (see. e.g., Kabat et al., supra). Chothia refers instead to the location of the structural loops (see, e.g., Chothia and Lesk, J. Mol. Biol. 196:901-17 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and Dübel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., Dev. Comp. Immunol. 27(1):55-77 (2003)). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, J. Mol. Biol. 309: 657-70 (2001). Correspondence between the numbering system, including, for example, the Kabat numbering and the IMGT unique numbering system, is well known to one skilled in the art (see. e.g., Kabat, supra; Chothia and Lesk, supra; Martin, supra; Lefranc et al., supra). The residues from each of these hypervariable regions or CDRs are exemplified in Table 1 below.

TABLE 1

Exemplary CDRs According to Various Numbering Systems

| Loop | Kabat | AbM | Chothia | Contact | IMGT |
|---|---|---|---|---|---|
| CDR L1 | L24--L34 | L24--L34 | L26--L32 or L24--L34 | L30--L36 | L27--L38 |
| CDR L2 | L50--L56 | L50--L56 | L50--L52 or L50--L56 | L46--L55 | L56--L65 |
| CDR L3 | L89--L97 | L89--L97 | L91--L96 or L89--L97 | L89--L96 | L105-L117 |
| CDR H1 | H31--H35B (Kabat Numbering) | H26--H35B | H26--H32 . . . 34 | H30--H35B | H27--H38 |
| CDR H1 | H31--H35 (Chothia Numbering) | H26--H35 | H26--H32 | H30--H35 | |
| CDR H2 | H50--H65 | H50--H58 | H53--H55 or H52--H56 | H47--H58 | H56--H65 |
| CDR H3 | H95--H102 | H95--H102 | H96--H101 or H95--H102 | H93--H101 | H105-H117 |

The boundaries of a given CDR may vary depending on the scheme used for identification. Thus, unless otherwise specified, the terms "CDR" and "complementary determining region" of a given antibody or region thereof, such as a variable region, as well as individual CDRs (e.g., CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the IMGT, Kabat, Chothia, or Contact method. In some instances, one or more positions according to the Kabat numbering may not be occupied in the actual sequence, or the actual sequence may contain more amino acid residues than the number allowed for by the Kabat numbering. See, e.g., Deschacht et al., 2010. J Immunol 184: 5696-704 for an exemplary numbering for VHH domains according to Kabat. In other cases, the particular amino acid sequence of a CDR is given. It should be noted CDR regions may also be defined by a combination of various numbering systems, e.g., a combination of Kabat and Chothia numbering systems, or a combination of Kabat and IMGT numbering systems. Therefore, the term such as "a CDR as set forth in a specific VH or VHH" includes any CDR1 as defined by the exemplary CDR numbering systems described above, but is not limited thereby. Once a variable region (e.g., a VHH, VH or VL) is given, those skilled in the art would understand that CDRs within the region can be defined by different numbering systems or combinations thereof.

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies (e.g., single domain antibodies), diabodies, linear antibodies, and bispecific antibodies. FR residues are those variable domain residues other than the hypervariable region residues or CDR residues.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

As used herein, an "epitope" is a term in the art and refers to a localized region of an antigen to which a binding molecule (e.g., an antibody comprising a single domain antibody sequence) can specifically bind. An epitope can be a linear epitope or a conformational, non-linear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, a binding molecule binds to a group of amino acids regardless of whether they are folded in a natural three dimensional protein structure. In other embodiments, a binding molecule requires amino acid residues making up the epitope to exhibit a particular conformation (e.g., bend, twist, turn or fold) in order to recognize and bind the epitope.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

An "agonist" or activating antibody is one that enhances or initiates signaling by the antigen to which it binds. In some embodiments, agonist antibodies cause or activate signaling without the presence of the natural ligand.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

"Chimeric antigen receptor" or "CAR" as used herein refers to genetically engineered receptors, which can be used to graft one or more antigen specificity onto immune effector cells, such as T cells. Some CARs are also known as "artificial T-cell receptors," "chimeric T cell receptors," or "chimeric immune receptors." In some embodiments, the CAR comprises an extracellular antigen binding domain specific for one or more antigens (such as tumor antigens), a transmembrane domain, and an intracellular signaling domain of a T cell and/or other receptors. "CAR-T cell" refers to a T cell that expresses a CAR.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces a binding molecule of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding a single domain antibody or an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule. Specifically, an "isolated" nucleic acid molecule encoding a CAR or an sdAb described herein is a nucleic acid molecule that is identified and separated from at least one contaminant nucleic acid molecule with which it is ordinarily associated in the environment in which it was produced.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, the term "operatively linked," and similar phrases (e.g., genetically fused), when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

The term "vector" refers to a substance that is used to carry or include a nucleic acid sequence, including for example, a nucleic acid sequence encoding a binding molecule (e.g., an antibody) as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

"Excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The term "excipient" can also refer to a diluent, adjuvant (e.g., Freunds' adjuvant (complete or incomplete) or vehicle.

In some embodiments, excipients are pharmaceutically acceptable excipients. Examples of pharmaceutically acceptable excipients include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. Other examples of pharmaceutically acceptable excipients are described in Remington and Gennaro, *Remington's Pharmaceutical Sciences* (18th ed. 1990).

In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009. In some embodiments, pharmaceutically acceptable excipients are nontoxic to the cell or mammal being exposed thereto at the dosages and concentrations employed. In some embodiments, a pharmaceutically acceptable excipient is an aqueous pH buffered solution.

In some embodiments, excipients are sterile liquids, such as water and oils, including those of petroleum, animal, vegetable, or synthetic origin, such as peanut oil, soybean oil, mineral oil, sesame oil, and the like. Water is an exemplary excipient when a composition (e.g., a pharmaceutical composition) is administered intravenously. Saline solutions and aqueous dextrose and glycerol solutions can also be employed as liquid excipients, particularly for injectable solutions. An excipient can also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard excipients such as pharmaceutical grades of mannitol, lactose, starch, magnesium stearate, sodium saccharine, cellulose, magnesium carbonate, etc.

Compositions, including pharmaceutical compounds, may contain a binding molecule (e.g., an antibody), for example, in isolated or purified form, together with a suitable amount of excipients.

The term "effective amount" or "therapeutically effective amount" as used herein refers to the amount of a single domain antibody or a therapeutic molecule comprising an agent and the single domain antibody or pharmaceutical composition provided herein which is sufficient to result in the desired outcome.

The terms "subject" and "patient" may be used interchangeably. As used herein, in certain embodiments, a subject is a mammal, such as a non-primate or a primate (e.g., human). In specific embodiments, the subject is a human. In one embodiment, the subject is a mammal, e.g., a human, diagnosed with a disease or disorder. In another embodiment, the subject is a mammal, e.g., a human, at risk of developing a disease or disorder.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies. Treating may be determined by assessing whether there has been a decrease, alleviation and/or mitigation of one or more symptoms associated with the underlying disorder such that an improvement is observed with the patient, despite that the patient may still be afflicted with the underlying disorder. The term "treating" includes both managing and ameliorating the disease. The terms "manage," "managing," and "management" refer to the beneficial effects that a subject derives from a therapy which does not necessarily result in a cure of the disease.

The terms "prevent," "preventing," and "prevention" refer to reducing the likelihood of the onset (or recurrence) of a disease, disorder, condition, or associated symptom(s) (e.g., diabetes or a cancer).

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

"B cell associated disease or disorder" as used herein refers to a disease or disorder mediated by B cells or conferred by abnormal B cell functions (such as dysregulation of B-cell function). "B cell associated disease or disorder" as used herein includes but not limited to a B cell malignancy such as a B cell leukemia or B cell lymphoma. It also includes marginal zone lymphoma (e.g., splenic marginal zone lymphoma), diffuse large B cell lymphoma (DLBCL), mantle cell lymphoma (MCL), primary central nervous system (CNS) lymphoma, primary mediastinal B cell lymphoma (PMBL), small lymphocytic lymphoma (SLL), B cell prolymphocytic leukemia (B-PLL), follicular lymphoma (FL), burkitt lymphoma, primary intraocular lymphoma, chronic lymphocytic leukemia (CLL), acute lymphoblastic leukemia (ALL), hairy cell leukemia (HCL), precursor B lymphoblastic leukemia, non-hodgkin lymphoma (NHL), high-grade B-cell lymphoma (HGBL), and multiple myelomia (MM). "B cell associated disease or disorder" also includes certain autoimmune and/or inflammatory disease, such as those associated with inappropriate or enhanced B cell numbers and/or activation.

"CD19 associated disease or disorder" as used herein refers to a disease or disorder that comprises a cell or tissue in which CD19 is expressed. In some embodiments, CD19 associated disease or disorder comprises a cell on which CD19 is abnormally expressed, e.g., with higher expression of CD19 as compared with a normal or healthy cell.

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "between" as used in a phrase as such "between A and B" or "between A-B" refers to a range including both A and B.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2. Single Domain Antibodies

5.2.1. Single Domain Antibodies that Bind to CD19

In one aspect, provided herein are single domain antibodies (e.g., VHH domains) capable of binding to CD19.

In some embodiments, the single domain antibodies (e.g., VHH domains) provided herein bind to human CD19. The human CD19 antigen is a 95 kd transmembrane glycoprotein belonging to the immunoglobulin (Ig) superfamily. Carter and Barrington, *Curr Dir Autoimmun,* 7:4-32 (2004). CD19 is encoded by the 7.41 kilobite cd19 gene located on the short arm of chromosome 16, 16p11.2. Zhou et al., *Immunogenetics*. 35(2):102-11 (1992). CD19 is specifically expressed in normal and neoplastic B cells, as well as follicular dendritic cells.

In some embodiments, the anti-CD19 single domain antibody provided herein modulates one or more CD19 activities. In some embodiments, the anti-CD19 single domain antibody provided herein is an antagonist antibody.

In some embodiments, the anti-CD19 single domain antibody provided herein binds to CD19 (e.g., human CD19) with a dissociation constant ($K_D$) of ≤1 μM, ≤100 μM, ≤10 μM, ≤1 nM, ≤0.1 nM, ≤0.01 nM, or ≤0.001 nM (e.g. $10^{-8}$M or less, e.g. from $10^{-4}$M to $10^{-13}$M, e.g., from $10^{-9}$ M to $10^{-13}$ M). A variety of methods of measuring binding affinity are known in the art, any of which can be used for purposes of the present disclosure, including by RIA, for example, performed with the Fab version of an antibody of interest and its antigen (Chen et al., 1999, J. Mol Biol 293:865-81); by biolayer interferometry (BLI) or surface plasmon resonance (SPR) assays by Octet®, using, for example, an Octet®Red96 system, or by Biacore®, using, for example, a Biacore®TM-2000 or a Biacore®TM-3000. An "on-rate" or "rate of association" or "association rate" or "kon" may also be determined with the same biolayer interferometry (BLI) or surface plasmon resonance (SPR) techniques described above using, for example, the Octet®Red96, the Biacore®TM-2000, or the Biacore®TM-3000 system.

In some embodiments, the anti-CD19 single domain antibodies provided herein are VHH domains. Exemplary VHH domains provided herein are generated as described below in Section 6, and these VHH domains are referred to as VHH-083, VHH-111, VHH-131, 77LICA542, 77LICA519, 77LICA602, LIC1157, LIC1159, huVHH-773, huVHH-776, A592H1, A592H2, A592H3, and A592H4, as also shown in Table 2 below.

Thus, in some embodiments, the single domain antibody provided herein comprises one or more CDR sequences of any one of VHH-083, VHH-111, VHH-131, 77LICA542, 77LICA519, 77LICA602, LIC1157, LIC1159, huVHH-773, huVHH-776, A592H1, A592H2, A592H3, and A592H4. In some embodiments, provided herein is a single domain antibody that binds to CD19 comprising the following structure: FR1-CDR1-FR2-CDR2-FR3-CDR3-FR4, wherein the CDR sequences are selected from those in VHH-083, VHH-111, VHH-131, 77LICA542, 77LICA519, 77LICA602, LIC1157, LIC1159, huVHH-773, huVHH-776, A592H1, A592H2, A592H3, and/or A592H4.

TABLE 2

| Exemplary Single Domain Antibodies | | | | |
|---|---|---|---|---|
| | VHH | CDR1 | CDR2 | CDR3 |
| VHH-083 | SEQ ID NO: 43 | SEQ ID NO: 1<br>SEQ ID NO: 22 or 108 | SEQ ID NO: 8<br>SEQ ID NO: 29 | SEQ ID NO: 15<br>SEQ ID NO: 36 |
| VHH-111 | SEQ ID NO: 44 | SEQ ID NO: 2<br>SEQ ID NO: 23 or 109 | SEQ ID NO: 9<br>SEQ ID NO: 30 | SEQ ID NO: 16<br>SEQ ID NO: 37 |
| 77LICA542 | SEQ ID NO: 45 | SEQ ID NO: 3<br>SEQ ID NO: 24 or 110 | SEQ ID NO: 10<br>SEQ ID NO: 31 | SEQ ID NO: 17<br>SEQ ID NO: 38 |
| 77LICA519 | SEQ ID NO: 46 | SEQ ID NO: 4<br>SEQ ID NO: 25 or 111 | SEQ ID NO: 11<br>SEQ ID NO: 32 | SEQ ID NO: 18<br>SEQ ID NO: 39 |
| 77LICA602 | SEQ ID NO: 47 | SEQ ID NO: 5<br>SEQ ID NO: 26 or 112 | SEQ ID NO: 12<br>SEQ ID NO: 33 | SEQ ID NO: 19<br>SEQ ID NO: 40 |
| LIC1157 | SEQ ID NO: 48 | SEQ ID NO: 6<br>SEQ ID NO: 27 or 113 | SEQ ID NO: 13<br>SEQ ID NO: 34 | SEQ ID NO: 20<br>SEQ ID NO: 41 |
| LIC1159 | SEQ ID NO: 49 | SEQ ID NO: 7<br>SEQ ID NO: 28 or 114 | SEQ ID NO: 14<br>SEQ ID NO: 35 | SEQ ID NO: 21<br>SEQ ID NO: 42 |
| huVHH-773 | SEQ ID NO: 51 | SEQ ID NO: 1<br>SEQ ID NO: 22 or 108 | SEQ ID NO: 8<br>SEQ ID NO: 29 | SEQ ID NO: 15<br>SEQ ID NO: 36 |
| huVHH-776 | SEQ ID NO: 52 | SEQ ID NO: 1<br>SEQ ID NO: 22 or 108 | SEQ ID NO: 8<br>SEQ ID NO: 29 | SEQ ID NO: 15<br>SEQ ID NO: 36 |
| A592H1 | SEQ ID NO: 53 | SEQ ID NO: 1<br>SEQ ID NO: 22 or 108 | SEQ ID NO: 8<br>SEQ ID NO: 29 | SEQ ID NO: 15<br>SEQ ID NO: 36 |
| A592H2 | SEQ ID NO: 54 | SEQ ID NO: 1<br>SEQ ID NO: 22 or 108 | SEQ ID NO: 8<br>SEQ ID NO: 29 | SEQ ID NO: 50<br>SEQ ID NO: 36 |
| A592H3 | SEQ ID NO: 55 | SEQ ID NO: 1<br>SEQ ID NO: 22 or 108 | SEQ ID NO: 8<br>SEQ ID NO: 29 | SEQ ID NO: 15<br>SEQ ID NO: 36 |
| A592H4 | SEQ ID NO: 56 | SEQ ID NO: 1<br>SEQ ID NO: 22 or 108 | SEQ ID NO: 8<br>SEQ ID NO: 29 | SEQ ID NO: 15<br>SEQ ID NO: 36 |
| VHH131 | SEQ ID NO: 104 | SEQ ID NO: 1<br>SEQ ID NO: 22 or 108 | SEQ ID NO: 8<br>SEQ ID NO: 103 | SEQ ID NO: 15<br>SEQ ID NO: 36 |

In some embodiments, there is provided an anti-CD19 single domain antibody comprising one, two, or all three CDRS of the amino acid sequence of SEQ ID NO: 43. In some embodiments, there is provided an anti-CD19 single domain antibody comprising one, two, or all three CDRS of the amino acid sequence of SEQ ID NO: 44. In some embodiments, there is provided an anti-CD19 single domain antibody comprising one, two, or all three CDRS of the amino acid sequence of SEQ ID NO: 45. In some embodiments, there is provided an anti-CD19 single domain antibody comprising one, two, or all three CDRS of the amino acid sequence of SEQ ID NO: 46. In some embodiments, there is provided an anti-CD19 single domain antibody comprising one, two, or all three CDRS of the amino acid sequence of SEQ ID NO: 47. In some embodiments, there is provided an anti-CD19 single domain antibody comprising one, two, or all three CDRS of the amino acid sequence of SEQ ID NO: 48. In some embodiments, there is provided an anti-CD19 single domain antibody comprising one, two, or all three CDRS of the amino acid sequence of SEQ ID NO: 49. In some embodiments, there is provided an anti-CD19 single domain antibody comprising one, two, or all three CDRs of the amino acid sequence of SEQ ID NO: 51. In some embodiments, there is provided an anti-CD19 single domain antibody comprising one, two, or all three CDRs of the amino acid sequence of SEQ ID NO: 52. In some embodiments, there is provided an anti-CD19 single domain antibody comprising one, two, or all three CDRs of the amino acid sequence of SEQ ID NO: 53. In some embodiments, there is provided an anti-CD19 single domain antibody comprising one, two, or all three CDRs of the amino acid sequence of SEQ ID NO: 54. In some embodiments, there is provided an anti-CD19 single domain antibody comprising one, two, or all three CDRs of the amino acid sequence of SEQ ID NO: 55. In some embodiments, there is provided an anti-CD19 single domain antibody comprising one, two, or all three CDRs of the amino acid sequence of SEQ ID NO: 56. In some embodiments, there is provided an anti-CD19 single domain antibody comprising one, two, or all three CDRs of the amino acid sequence of SEQ ID NO: 104. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 43. In some embodiments, the single domain antibody has a CDR2 having an amino acid sequence of the CDR2 as set forth in SEQ ID NO: 43. In other embodiments, the single domain antibody has a CDR3 having an amino acid sequence of the CDR3 as set forth in SEQ ID NO: 43 (e.g., SEQ ID NOs: 15 or 36). In some embodiments, the single domain antibody has a CDR1 and a CDR2 having amino acid sequences of the CDR1 and the CDR2 as set forth in SEQ ID NO: 43. In some embodiments, the single domain antibody has a CDR1 and a CDR3 having amino acid sequences of the CDR1 and the CDR3 as set forth in SEQ ID NO: 43. In some embodiments, the single domain antibody has a CDR2 and a CDR3 having amino acid sequences of the CDR2 and the CDR3 as set forth in SEQ ID NO: 43. In some embodiments, the single domain antibody has a CDR1, a CDR2, and a CDR3 having amino acid sequences of the CDR1, the CDR2, and the CDR3 as set forth in SEQ ID NO: 43. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 44. In some embodiments, the single domain antibody has a CDR2 having an amino acid sequence of the CDR2 as set forth in SEQ ID NO: 44. In other embodiments, the single domain antibody has a CDR3 having an amino acid sequence of the CDR3 as set forth in SEQ ID NO: 44 (e.g., SEQ ID NOs: 16 or 37). In some embodiments, the single domain antibody has a CDR1 and a CDR2 having amino acid sequences of the CDR1 and the CDR2 as set forth in SEQ ID NO: 44. In some embodiments, the single domain antibody has a CDR1 and a CDR3 having amino acid sequences of the CDR1 and the CDR3 as set forth in SEQ ID NO: 44. In some embodiments, the single domain antibody has a CDR2 and a CDR3 having amino acid sequences of the CDR2 and the CDR3 as set forth in SEQ ID NO: 44. In some embodiments, the single domain antibody has a CDR1, a CDR2, and a CDR3 having amino acid sequences of the CDR1, the CDR2, and the CDR3 as set forth in SEQ ID NO: 44. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 45. In some embodiments, the single domain antibody has a CDR2 having an amino acid sequence of the CDR2 as set forth in SEQ ID NO: 45. In other embodiments, the single domain antibody has a CDR3 having an amino acid sequence of the CDR3 as set forth in SEQ ID NO: 45 (e.g., SEQ ID NOs: 17 or 38). In some embodiments, the single domain antibody has a CDR1 and a CDR2 having amino acid sequences of the CDR1 and the CDR2 as set forth in SEQ ID NO: 45. In some embodiments, the single domain antibody has a CDR1 and a CDR3 having amino acid sequences of the CDR1 and the CDR3 as set forth in SEQ ID NO: 45. In some embodiments, the single domain antibody has a CDR2 and a CDR3 having amino acid sequences of the CDR2 and the CDR3 as set forth in SEQ ID NO: 45. In some embodiments, the single domain antibody has a CDR1, a CDR2, and a CDR3 having amino acid sequences of the CDR1, the CDR2, and the CDR3 as set forth in SEQ ID NO: 45. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 46. In some embodiments, the single domain antibody has a CDR2 having an amino acid sequence of the CDR2 as set forth in SEQ ID NO: 46. In other embodiments, the single domain antibody has a CDR3 having an amino acid sequence of the CDR3 as set forth in SEQ ID NO: 46 (e.g., SEQ ID NOs: 18 or 39). In some embodiments, the single domain antibody has a CDR1 and a CDR2 having amino acid sequences of the CDR1 and the CDR2 as set forth in SEQ ID NO: 46. In some embodiments, the single domain antibody has a CDR1 and a CDR3 having amino acid sequences of the CDR1 and the CDR3 as set forth in SEQ ID NO: 46. In some embodiments, the single domain antibody has a CDR2 and a CDR3 having amino acid sequences of the CDR2 and the CDR3 as set forth in SEQ ID NO: 46. In some embodiments, the single domain antibody has a CDR1, a CDR2, and a CDR3 having amino acid sequences of the CDR1, the CDR2, and the CDR3 as set forth in SEQ ID NO: 46. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 47. In some embodiments, the single domain antibody has a CDR2 having an amino acid sequence of the CDR2 as set forth in SEQ ID NO: 47. In other embodiments, the single domain antibody has a CDR3 having an amino acid sequence of the CDR3 as set forth in SEQ ID NO: 47 (e.g., SEQ ID NOs: 19 or 40). In some embodiments, the single domain antibody has a CDR1 and a CDR2 having amino acid sequences of the CDR1 and the CDR2 as set forth in SEQ ID NO: 47. In some embodiments, the single domain antibody has a CDR1 and a CDR3 having amino acid sequences of the CDR1 and the CDR3 as set forth in SEQ ID NO: 47. In some embodiments, the single domain antibody has a CDR2 and a CDR3 having amino acid sequences of the CDR2 and the CDR3 as set forth in SEQ ID NO: 47. In some embodiments, the single domain antibody has a CDR1, a CDR2, and a CDR3 having amino acid sequences of the CDR1, the CDR2, and the CDR3 as set forth in SEQ ID NO: 47. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 48. In some embodiments, the single domain antibody has a CDR2 having an amino acid sequence of the CDR2 as set forth in SEQ ID NO: 48. In other embodiments, the single domain antibody has a CDR3 having an amino acid sequence of the CDR3 as set forth in SEQ ID NO: 48 (e.g., SEQ ID NOs: 20 or 41). In some embodiments, the single domain antibody has a CDR1 and a CDR2 having amino acid sequences of the CDR1 and the CDR2 as set forth in SEQ ID NO: 48. In some embodiments, the single domain antibody has a CDR1 and a CDR3 having amino acid sequences of the CDR1 and the CDR3 as set forth in SEQ ID NO: 48. In some embodiments, the single domain antibody has a CDR2 and a CDR3 having amino acid sequences of the CDR2 and the CDR3 as set forth in SEQ ID NO: 48. In some embodiments, the single domain antibody has a CDR1, a CDR2, and a CDR3 having amino acid sequences of the CDR1, the CDR2, and the CDR3 as set forth in SEQ ID NO: 48. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 49. In some embodiments, the single domain antibody has a CDR2 having an amino acid sequence of the CDR2 as set forth in SEQ ID NO: 49. In other embodiments, the single domain antibody has a CDR3 having an amino acid sequence of the CDR3 as set forth in SEQ ID NO: 49 (e.g., SEQ ID NOs: 21 or 42). In some embodiments, the single domain antibody has a CDR1 and a CDR2 having amino acid sequences of the CDR1 and the CDR2 as set forth in SEQ ID NO: 49. In some embodiments, the single domain antibody has a CDR1 and a CDR3 having amino acid sequences of the CDR1 and the CDR3 as set forth in SEQ ID NO: 49. In some embodiments, the single domain antibody has a CDR2 and a CDR3 having amino acid sequences of the CDR2 and the CDR3 as set forth in SEQ ID NO: 49. In some embodiments, the single domain antibody has a CDR1, a CDR2, and a CDR3 having amino acid sequences of the CDR1, the CDR2, and the CDR3 as set forth in SEQ ID NO: 49. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 51. In some embodiments, the single domain antibody has a CDR2 having an amino acid sequence of the CDR2 as set forth in SEQ ID NO: 51. In other embodiments, the single domain antibody has a CDR3 having an amino acid sequence of the CDR3 as set forth in SEQ ID NO: 51 (e.g., SEQ ID NOs: 15 or 36). In some embodiments, the single domain antibody has a CDR1 and a CDR2 having amino acid sequences of the CDR1 and the CDR2 as set forth in SEQ ID NO: 51. In some embodiments, the single domain antibody has a CDR1 and a CDR3 having amino acid sequences of the CDR1 and the CDR3 as set forth in SEQ ID NO: 51. In some embodiments, the single domain antibody has a CDR2 and a CDR3 having amino acid sequences of the CDR2 and the CDR3 as set forth in SEQ ID NO: 51. In some embodiments, the single domain antibody has a CDR1, a CDR2, and a CDR3 having amino acid sequences of the CDR1, the CDR2, and the CDR3 as set forth in SEQ ID NO: 51. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 52. In some embodiments, the single domain antibody has a CDR2 having an amino acid sequence of the CDR2 as set forth in SEQ ID NO: 52. In other embodiments, the single domain antibody has a CDR3 having an amino acid sequence of the CDR3 as set forth in SEQ ID NO: 52 (e.g., SEQ ID NOs: 15 or 36). In some embodiments, the single domain antibody has a CDR1 and a CDR2 having amino acid sequences of the CDR1 and the CDR2 as set forth in SEQ ID NO: 52. In some embodiments, the single domain antibody has a CDR1 and a CDR3 having amino acid sequences of the CDR1 and the CDR3 as set forth in SEQ ID NO: 52. In some embodiments, the single domain antibody has a CDR2 and a CDR3 having amino acid sequences of the CDR2 and the CDR3 as set forth in SEQ ID NO: 52. In some embodiments, the single domain antibody has a CDR1, a CDR2, and a CDR3 having amino acid sequences of the CDR1, the CDR2, and the CDR3 as set forth in SEQ ID NO: 52. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 53. In some embodiments, the single domain antibody has a CDR2 having an amino acid sequence of the CDR2 as set forth in SEQ ID NO: 53. In other embodiments, the single domain antibody has a CDR3 having an amino acid sequence of the CDR3 as set forth in SEQ ID NO: 53 (e.g., SEQ ID NOs: 15 or 36). In some embodiments, the single domain antibody has a CDR1 and a CDR2 having amino acid sequences of the CDR1 and the CDR2 as set forth in SEQ ID NO: 53. In some embodiments, the single domain antibody has a CDR1 and a CDR3 having amino acid sequences of the CDR1 and the CDR3 as set forth in SEQ ID NO: 53. In some embodiments, the single domain antibody has a CDR2 and a CDR3 having amino acid sequences of the CDR2 and the CDR3 as set forth in SEQ ID NO: 53. In some embodiments, the single domain antibody has a CDR1, a CDR2, and a CDR3 having amino acid sequences of the CDR1, the CDR2, and the CDR3 as set forth in SEQ ID NO: 53. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 54. In some embodiments, the single domain antibody has a CDR2 having an amino acid sequence of the CDR2 as set forth in SEQ ID NO: 54. In other embodiments, the single domain antibody has a CDR3 having an amino acid sequence of the CDR3 as set forth in SEQ ID NO: 54 (e.g., SEQ ID NOs: 50 or 36). In some embodiments, the single domain antibody has a CDR1 and a CDR2 having amino acid sequences of the CDR1 and the CDR2 as set forth in SEQ ID NO: 54. In some embodiments, the single domain antibody has a CDR1 and a CDR3 having amino acid sequences of the CDR1 and the CDR3 as set forth in SEQ ID NO: 54. In some embodiments, the single domain antibody has a CDR2 and a CDR3 having amino acid sequences of the CDR2 and the CDR3 as set forth in SEQ ID NO: 54. In some embodiments, the single domain antibody has a CDR1, a CDR2, and a CDR3 having amino acid sequences of the CDR1, the CDR2, and the CDR3 as set forth in SEQ ID NO: 54. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 55. In some embodiments, the single domain antibody has a CDR2 having an amino acid sequence of the CDR2 as set forth in SEQ ID NO: 55. In other embodiments, the single domain antibody has a CDR3 having an amino acid sequence of the CDR3 as set forth in SEQ ID NO: 55 (e.g., SEQ ID NOs: 15 or 36). In some embodiments, the single domain antibody has a CDR1 and a CDR2 having amino acid sequences of the CDR1 and the CDR2 as set forth in SEQ ID NO: 55. In some embodiments, the single domain antibody has a CDR1 and a CDR3 having amino acid sequences of the CDR1 and the CDR3 as set forth in SEQ ID NO: 55. In some embodiments, the single domain antibody has a CDR2 and a CDR3 having amino acid sequences of the CDR2 and the CDR3 as set forth in SEQ ID NO: 55. In some embodiments, the single domain antibody has a CDR1, a CDR2, and a CDR3 having amino acid sequences of the CDR1, the CDR2, and the CDR3 as set forth in SEQ ID NO: 55. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 56. In some embodiments, the single domain antibody has a CDR2 having an amino acid sequence of the CDR2 as set forth in SEQ ID NO: 56. In other embodiments, the single domain antibody has a CDR3 having an amino acid sequence of the CDR3 as set forth in SEQ ID NO: 56 (e.g., SEQ ID NOs: 15 or 36). In some embodiments, the single domain antibody has a CDR1 and a CDR2 having amino acid sequences of the CDR1 and the CDR2 as set forth in SEQ ID NO: 56. In some embodiments, the single domain antibody has a CDR1 and a CDR3 having amino acid sequences of the CDR1 and the CDR3 as set forth in SEQ ID NO: 56. In some embodiments, the single domain antibody has a CDR2 and a CDR3 having amino acid sequences of the CDR2 and the CDR3 as set forth in SEQ ID NO: 56. In some embodiments, the single domain antibody has a CDR1, a CDR2, and a CDR3 having amino acid sequences of the CDR1, the CDR2, and the CDR3 as set forth in SEQ ID NO: 56. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 104. In some embodiments, the single domain antibody has a CDR2 having an amino acid sequence of the CDR2 as set forth in SEQ ID NO: 104. In other embodiments, the single domain antibody has a CDR3 having an amino acid sequence of the CDR3 as set forth in SEQ ID NO: 104 (e.g., SEQ ID NOs: 15 or 36). In some embodiments, the single domain antibody has a CDR1 and a CDR2 having amino acid sequences of the CDR1 and the CDR2 as set forth in SEQ ID NO: 104. In some embodiments, the single domain antibody has a CDR1 and a CDR3 having amino acid sequences of the CDR1 and the CDR3 as set forth in SEQ ID NO: 104. In some embodiments, the single domain antibody has a CDR2 and a CDR3 having amino acid sequences of the CDR2 and the CDR3 as set forth in SEQ ID NO: 104. In some embodiments, the single domain antibody has a CDR1, a CDR2, and a CDR3 having amino acid sequences of the CDR1, the CDR2, and the CDR3 as set forth in SEQ ID NO: 104. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, provided herein is a single domain antibody that binds to CD19 comprising the following structure: FR1-CDR1-FR2-CDR2-FR3-CDR3-FR4, wherein (i) the CDR1 comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 22 or 108, SEQ ID NO: 23 or 109, SEQ ID NO: 24 or 110, SEQ ID NO: 25 or 111, SEQ ID NO: 26 or 112, SEQ ID NO: 27 or 113 or SEQ ID NO: 28 or 114; (ii) the CDR2 comprises an amino acid sequence of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 29, SEQ ID NO: 30, SEQ ID NO: 31, SEQ ID NO: 32, SEQ ID NO: 33, SEQ ID NO: 34, SEQ ID NO: 35, or SEQ ID NO: 103 and/or (iii) the CDR3 comprises an amino acid sequence of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 50. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, provided herein is a single domain antibody that binds to CD19 comprising the following structure: FR1-CDR1-FR2-CDR2-FR3-CDR3-FR4, wherein (i) the CDR1 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 22 or 108, SEQ ID NO: 23 or 109, SEQ ID NO: 24 or 110, SEQ ID NO: 25 or 111, SEQ ID NO: 26 or 112, SEQ ID NO: 27 or 113 or SEQ ID NO: 28 or 114; (ii) the CDR2 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 29, SEQ ID NO: 30, SEQ ID NO: 31, SEQ ID NO: 32, SEQ ID NO: 33, SEQ ID NO: 34, SEQ ID NO: 35 or SEQ ID NO: 103; and/or (iii) the CDR3 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 50. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the CDR1 comprises the amino acid sequence of SEQ ID NO: 1; the CDR2 comprises the amino acid sequence of SEQ ID NO: 8; and the CDR3 comprises the amino acid sequence of SEQ ID NO: 15. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the CDR1 comprises the amino acid sequence of SEQ ID NO: 22 or 108; the CDR2 comprises the amino acid sequence of SEQ ID NO: 29; and the CDR3 comprises the amino acid sequence of SEQ ID NO: 36. In some embodiments, the CDR1 comprises the amino acid sequence of SEQ ID NO: 22; the CDR2 comprises the amino acid sequence of SEQ ID NO: 29; and the CDR3 comprises the amino acid sequence of SEQ ID NO: 36. In some embodiments, the CDR1 comprises the amino acid sequence of SEQ ID NO: 108; the CDR2 comprises the amino acid sequence of SEQ ID NO: 29; and the CDR3 comprises the amino acid sequence of SEQ ID NO: 36. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the CDR1 comprises the amino acid sequence of SEQ ID NO: 2; the CDR2 comprises the amino acid sequence of SEQ ID NO: 9; and the CDR3 comprises the amino acid sequence of SEQ ID NO: 16. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the CDR1 comprises the amino acid sequence of SEQ ID NO: 23 or 109; the CDR2 comprises the amino acid sequence of SEQ ID NO: 30; and the CDR3 comprises the amino acid sequence of SEQ ID NO: 37. In some embodiments, the CDR1 comprises the amino acid sequence of SEQ ID NO: 23; the CDR2 comprises the amino acid sequence of SEQ ID NO: 30; and the CDR3 comprises the amino acid sequence of SEQ ID NO: 37. In some embodiments, the CDR1 comprises the amino acid sequence of SEQ ID NO: 109; the CDR2 comprises the amino acid sequence of SEQ ID NO: 30; and the CDR3 comprises the amino acid sequence of SEQ ID NO: 37. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, in the anti-CD19 sdAb provided herein, the CDR1 comprises the amino acid sequence of SEQ ID NO: 3; the CDR2 comprises the amino acid sequence of SEQ ID NO: 10; and the CDR3 comprises the amino acid sequence of SEQ ID NO: 17. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, in the anti-CD19 sdAb provided herein, the CDR1 comprises the amino acid sequence of SEQ ID NO: 24 or 110; the CDR2 comprises the amino acid sequence of SEQ ID NO: 31; and the CDR3 comprises the amino acid sequence of SEQ ID NO: 38. In some embodiments, in the anti-CD19 sdAb provided herein, the CDR1 comprises the amino acid sequence of SEQ ID NO: 24; the CDR2 comprises the amino acid sequence of SEQ ID NO: 31; and the CDR3 comprises the amino acid sequence of SEQ ID NO: 38. In some embodiments, in the anti-CD19 sdAb provided herein, the CDR1 comprises the amino acid sequence of SEQ ID NO: 110; the CDR2 comprises the amino acid sequence of SEQ ID NO: 31; and the CDR3 comprises the amino acid sequence of SEQ ID NO: 38. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, in the anti-CD19 sdAb provided herein, the CDR1 comprises the amino acid sequence of SEQ ID NO: 4; the CDR2 comprises the amino acid sequence of SEQ ID NO: 11; and the CDR3 comprises the amino acid sequence of SEQ ID NO: 18. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, in the anti-CD19 sdAb provided herein, the CDR1 comprises the amino acid sequence of SEQ ID NO: 25 or 111; the CDR2 comprises the amino acid sequence of SEQ ID NO: 32; and the CDR3 comprises the amino acid sequence of SEQ ID NO: 39. In some embodiments, in the anti-CD19 sdAb provided herein, the CDR1 comprises the amino acid sequence of SEQ ID NO: 25; the CDR2 comprises the amino acid sequence of SEQ ID NO: 32; and the CDR3 comprises the amino acid sequence of SEQ ID NO: 39. In some embodiments, in the anti-CD19 sdAb provided herein, the CDR1 comprises the amino acid sequence of SEQ ID NO: 111; the CDR2 comprises the amino acid sequence of SEQ ID NO: 32; and the CDR3 comprises the amino acid sequence of SEQ ID NO: 39. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 5; the CDR2 comprises the amino acid sequence of SEQ ID NO: 12; and the CDR3 comprises the amino acid sequence of SEQ ID NO: 19. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 26 or 112; the CDR2 comprises the amino acid sequence of SEQ ID NO: 33; and the CDR3 comprises the amino acid sequence of SEQ ID NO: 40. In other embodiments, in the anti-CD19 sdAb provided herein, the CDR1 comprises the amino acid sequence of SEQ ID NO: 26; the CDR2 comprises the amino acid sequence of SEQ ID NO: 33; and the CDR3 comprises the amino acid sequence of SEQ ID NO: 40. In other embodiments, in the anti-CD19 sdAb provided herein, the CDR1 comprises the amino acid sequence of SEQ ID NO: 112; the CDR2 comprises the amino acid sequence of SEQ ID NO: 33; and the CDR3 comprises the amino acid sequence of SEQ ID NO: 40. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 6; the CDR2 comprises the amino acid sequence of SEQ ID NO: 13; and the CDR3 comprises the amino acid sequence of SEQ ID NO: 20. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 27 or 113; the CDR2 comprises the amino acid sequence of SEQ ID NO: 34; and the CDR3 comprises the amino acid sequence of SEQ ID NO: 41. In other embodiments, in the anti-CD19 sdAb provided herein, the CDR1 comprises the amino acid sequence of SEQ ID NO: 27; the CDR2 comprises the amino acid sequence of SEQ ID NO: 34; and the CDR3 comprises the amino acid sequence of SEQ ID NO: 41. In other embodiments, in the anti-CD19 sdAb provided herein, the CDR1 comprises the amino acid sequence of SEQ ID NO: 113; the CDR2 comprises the amino acid sequence of SEQ ID NO: 34; and the CDR3 comprises the amino acid sequence of SEQ ID NO: 41. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 7; the CDR2 comprises the amino acid sequence of SEQ ID NO: 14; and the CDR3 comprises the amino acid sequence of SEQ ID NO: 21. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 28 or 114; the CDR2 comprises the amino acid sequence of SEQ ID NO: 35; and the CDR3 comprises the amino acid sequence of SEQ ID NO: 42. In other embodiments, in the anti-CD19 sdAb provided herein, the CDR1 comprises the amino acid sequence of SEQ ID NO: 28; the CDR2 comprises the amino acid sequence of SEQ ID NO: 35; and the CDR3 comprises the amino acid sequence of SEQ ID NO: 42. In other embodiments, in the anti-CD19 sdAb provided herein, the CDR1 comprises the amino acid sequence of SEQ ID NO: 114; the CDR2 comprises the amino acid sequence of SEQ ID NO: 35; and the CDR3 comprises the amino acid sequence of SEQ ID NO: 42. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 1; the CDR2 comprises the amino acid sequence of SEQ ID NO: 8; and the CDR3 comprises the amino acid sequence of SEQ ID NO: 50. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In other embodiments, in the anti-CD19 sdAb provided herein, the CDR1 comprises the amino acid sequence of SEQ ID NO: 22 or 108; the CDR2 comprises the amino acid sequence of SEQ ID NO: 103, and the CDR3 comprises the amino acid sequence of SEQ ID NO: 36. In other embodiments, in the anti-CD19 sdAb provided herein, the CDR1 comprises the amino acid sequence of SEQ ID NO: 22; the CDR2 comprises the amino acid sequence of SEQ ID NO: 103, and the CDR3 comprises the amino acid sequence of SEQ ID NO: 36. In other embodiments, in the anti-CD19 sdAb provided herein, the CDR1 comprises the amino acid sequence of SEQ ID NO: 108; the CDR2 comprises the amino acid sequence of SEQ ID NO: 103, and the CDR3 comprises the amino acid sequence of SEQ ID NO: 36. In some embodiments, the anti-CD19 single domain antibody is camelid. In some embodiments, the anti-CD19 single domain antibody is humanized. In some embodiments, the anti-CD19 single domain antibody comprises an acceptor human framework, e.g., a human immunoglobulin framework or a human consensus framework.

In some embodiments, the single domain antibody further comprises one or more framework regions of VHH-083, VHH-111, VHH-131, 77LICA542, 77LICA519, 77LICA602, LIC1157, LIC1159, huVHH-773, huVHH-776, A592H1, A592H2, A592H3, and/or A592H4. In some embodiments, the single domain antibody comprises one or more framework(s) derived from a VHH domain comprising the sequence of SEQ ID NO: 43. In some embodiments, the single domain antibody comprises one or more framework(s) derived from a VHH domain comprising the sequence of SEQ ID NO: 44. In some embodiments, the single domain antibody comprises one or more framework(s) derived from a VHH domain comprising the sequence of SEQ ID NO: 45. In some embodiments, the single domain antibody comprises one or more framework(s) derived from a VHH domain comprising the sequence of SEQ ID NO: 46. In some embodiments, the single domain antibody comprises one or more framework(s) derived from a VHH domain comprising the sequence of SEQ ID NO: 47. In some embodiments, the single domain antibody comprises one or more framework(s) derived from a VHH domain comprising the sequence of SEQ ID NO: 48. In some embodiments, the single domain antibody comprises one or more framework(s) derived from a VHH domain comprising the sequence of SEQ ID NO: 49. In some embodiments, the single domain antibody comprises one or more framework(s) derived from a VHH domain comprising the sequence of SEQ ID NO: 51. In some embodiments, the single domain antibody comprises one or more framework(s) derived from a VHH domain comprising the sequence of SEQ ID NO: 52. In some embodiments, the single domain antibody comprises one or more framework(s) derived from a VHH domain comprising the sequence of SEQ ID NO: 53. In some embodiments, the single domain antibody comprises one or more framework(s) derived from a VHH domain comprising the sequence of SEQ ID NO: 54. In some embodiments, the single domain antibody comprises one or more framework(s) derived from a VHH domain comprising the sequence of SEQ ID NO: 55. In some embodiments, the single domain antibody comprises one or more framework(s) derived from a VHH domain comprising the sequence of SEQ ID NO: 56. In some embodiments, the single domain antibody comprises one or more framework(s) derived from a VHH domain comprising the sequence of SEQ ID NO: 104.

In some embodiments, the single domain antibody provided herein is a humanized single domain antibody. In some embodiments, humanized single domain antibodies can be generated using the method exemplified in the Section 6 below or the methods described in the section below.

Framework regions described herein are determined based upon the boundaries of the CDR numbering system. In other words, if the CDRs are determined by, e.g., Kabat, IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, or the Chothia numbering system, FR2 is defined as the amino acid residues between CDR1 and CDR2 amino acid residues as defined by, e.g., the Kabat numbering system, the IMGT numbering system, or the Chothia numbering system, FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In some embodiments, there is provided an isolated anti-CD19 single domain antibody comprising a VHH domain having the amino acid sequence of SEQ ID NO: 43. In some embodiments, there is provided a polypeptide comprising the amino acid sequence of SEQ ID NO: 43. In some embodiments, there is provided an isolated anti-CD19 single domain antibody comprising a VHH domain having the amino acid sequence of SEQ ID NO: 44. In some embodiments, there is provided a polypeptide comprising the amino acid sequence of SEQ ID NO: 44. In some embodiments, there is provided an isolated anti-CD19 single domain antibody comprising a VHH domain having the amino acid sequence of SEQ ID NO: 45. In some embodiments, there is provided a polypeptide comprising the amino acid sequence of SEQ ID NO: 45. In some embodiments, there is provided an isolated anti-CD19 single domain antibody comprising a VHH domain having the amino acid sequence of SEQ ID NO: 46. In some embodiments, there is provided a polypeptide comprising the amino acid sequence of SEQ ID NO: 46. In some embodiments, there is provided an isolated anti-CD19 single domain antibody comprising a VHH domain having the amino acid sequence of SEQ ID NO: 47. In some embodiments, there is provided a polypeptide comprising the amino acid sequence of SEQ ID NO: 47. In some embodiments, there is provided an isolated anti-CD19 single domain antibody comprising a VHH domain having the amino acid sequence of SEQ ID NO: 48. In some embodiments, there is provided a polypeptide comprising the amino acid sequence of SEQ ID NO: 48. In some embodiments, there is provided an isolated anti-CD19 single domain antibody comprising a VHH domain having the amino acid sequence of SEQ ID NO: 49. In some embodiments, there is provided a polypeptide comprising the amino acid sequence of SEQ ID NO: 49. In some embodiments, there is provided an isolated anti-CD19 single domain antibody comprising a VHH domain having the amino acid sequence of SEQ ID NO: 51. In some embodiments, there is provided a polypeptide comprising the amino acid sequence of SEQ ID NO: 51. In some embodiments, there is provided an isolated anti-CD19 single domain antibody comprising a VHH domain having the amino acid sequence of SEQ ID NO: 52. In some embodiments, there is provided a polypeptide comprising the amino acid sequence of SEQ ID NO: 52. In some embodiments, there is provided an isolated anti-CD19 single domain antibody comprising a VHH domain having the amino acid sequence of SEQ ID NO: 53. In some embodiments, there is provided a polypeptide comprising the amino acid sequence of SEQ ID NO: 53. In some embodiments, there is provided an isolated anti-CD19 single domain antibody comprising a VHH domain having the amino acid sequence of SEQ ID NO: 54. In some embodiments, there is provided a polypeptide comprising the amino acid sequence of SEQ ID NO: 54. In some embodiments, there is provided an isolated anti-CD19 single domain antibody comprising a VHH domain having the amino acid sequence of SEQ ID NO: 55. In some embodiments, there is provided a polypeptide comprising the amino acid sequence of SEQ ID NO: 55. In some embodiments, there is provided an isolated anti-CD19 single domain antibody comprising a VHH domain having the amino acid sequence of SEQ ID NO: 56. In some embodiments, there is provided a polypeptide comprising the amino acid sequence of SEQ ID NO: 56. In some embodiments, there is provided an isolated anti-CD19 single domain antibody comprising a VHH domain having the amino acid sequence of SEQ ID NO: 104. In some embodiments, there is provided a polypeptide comprising the amino acid sequence of SEQ ID NO: 104.

In certain embodiments, an antibody described herein or an antigen-binding fragment thereof comprises amino acid sequences with certain percent identity relative to any one of antibodies VHH-083, VHH-111, VHH-131, 77LICA542, 77LICA519, 77LICA602, LIC1157, LIC1159, huVHH-773, huVHH-776, A592H1, A592H2, A592H3, and A592H4.

The determination of percent identity between two sequences (e.g., amino acid sequences or nucleic acid sequences) can be accomplished using a mathematical algorithm. A non-limiting example of a mathematical algorithm utilized for the comparison of two sequences is the algorithm of Karlin and Altschul, Proc. Natl. Acad. Sci. U.S.A. 87:2264 2268 (1990), modified as in Karlin and Altschul, Proc. Natl. Acad. Sci. U.S.A. 90:5873 5877 (1993). Such an algorithm is incorporated into the NBLAST and XBLAST programs of Altschul et al., J. Mol. Biol. 215:403 (1990). BLAST nucleotide searches can be performed with the NBLAST nucleotide program parameters set, e.g., for score=100, word length=12 to obtain nucleotide sequences homologous to a nucleic acid molecules described herein. BLAST protein searches can be performed with the XBLAST program parameters set, e.g., to score 50, word length=3 to obtain amino acid sequences homologous to a protein molecule described herein. To obtain gapped alignments for comparison purposes, Gapped BLAST can be utilized as described in Altschul et al., Nucleic Acids Res. 25:3389 3402 (1997). Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another non-limiting example of a mathematical algorithm utilized for the comparison of sequences is the algorithm of Myers and Miller, CABIOS 4:11-17 (1998). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some embodiments, there is provided an anti-CD19 single domain antibody comprising a VHH domain having at least about any one of 75%, 80%, 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 43-49, 51-56, and 104. In some embodiments, a VHH sequence having at least about any one of 75%, 80%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD19 single domain antibody comprising that sequence retains the ability to bind to CD19. In some embodiments, a total of 1 to 10 amino acids have been substituted, inserted and/or deleted in an amino acid sequence selected from SEQ ID NOs: 43-49, 51-56, and 104. In some embodiments, substitutions, insertions, or deletions occur in regions outside the CDRs (i.e., in the FRs). Optionally, the anti-CD19 single domain antibody comprises an amino acid sequence selected from SEQ ID NOs: 43-49, 51-56, and 104 including post-translational modifications of that sequence.

In certain embodiments, the single domain antibody described herein comprises a VHH domain having at least 75%, at least 80%, at least 85%, at least 90%, at least 91%, at least 92%, at least 93%, at least 94%, at least 95%, at least %%, at least 97%, at least 98%, or at least 99% sequence identity to the amino acid sequence of SEQ ID NO: 43, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least %%, at least 97%, at least 98%, or at least 99% sequence identity to the amino acid sequence of SEQ ID NO: 44, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least %%, at least 97%, at least 98%, or at least 99% sequence identity to the amino acid sequence of SEQ ID NO: 45, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least %%, at least 97%, at least 98%, or at least 99% sequence identity to the amino acid sequence of SEQ ID NO: 46, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least %%, at least 97%, at least 98%, or at least 99% sequence identity to the amino acid sequence of SEQ ID NO: 47, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 48, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least %%, at least 97%, at least 98%, or at least 99% sequence identity to the amino acid sequence of SEQ ID NO: 49, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least %%, at least 97%, at least 98%, or at least 99% sequence identity to the amino acid sequence of SEQ ID NO: 51, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 52, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 53, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 54, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 55, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 56, wherein the single domain antibody binds to CD19. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 104, wherein the single domain antibody binds to CD19.

In some embodiments, functional epitopes can be mapped, e.g., by combinatorial alanine scanning, to identify amino acids in the CD19 protein that are necessary for interaction with anti-CD19 single domain antibodies provided herein. In some embodiments, conformational and crystal structure of anti-CD19 single domain antibody bound to CD19 may be employed to identify the epitopes. In some embodiments, the present disclosure provides an antibody that specifically binds to the same epitope as any of the anti-CD19 single domain antibodies provided herein. For example, in some embodiments, an antibody is provided that binds to the same epitope as an anti-CD19 single domain antibody comprising the amino acid sequence of SEQ ID NO: 43. In some embodiments, an antibody is provided that binds to the same epitope as an anti-CD19 single domain antibody comprising the amino acid sequence of SEQ ID NO: 44. In some embodiments, an antibody is provided that binds to the same epitope as an anti-CD19 single domain antibody comprising the amino acid sequence of SEQ ID NO: 45. In some embodiments, an antibody is provided that binds to the same epitope as an anti-CD19 single domain antibody comprising the amino acid sequence of SEQ ID NO: 46. In some embodiments, an antibody is provided that binds to the same epitope as an anti-CD19 single domain antibody comprising the amino acid sequence of SEQ ID NO: 47. In some embodiments, an antibody is provided that binds to the same epitope as an anti-CD19 single domain antibody comprising the amino acid sequence of SEQ ID NO: 48. In some embodiments, an antibody is provided that binds to the same epitope as an anti-CD19 single domain antibody comprising the amino acid sequence of SEQ ID NO: 49. In some embodiments, an antibody is provided that binds to the same epitope as an anti-CD19 single domain antibody comprising the amino acid sequence of SEQ ID NO: 51. In some embodiments, an antibody is provided that binds to the same epitope as an anti-CD19 single domain antibody comprising the amino acid sequence of SEQ ID NO: 52. In some embodiments, an antibody is provided that binds to the same epitope as an anti-CD19 single domain antibody comprising the amino acid sequence of SEQ ID NO: 53. In some embodiments, an antibody is provided that binds to the same epitope as an anti-CD19 single domain antibody comprising the amino acid sequence of SEQ ID NO: 54. In some embodiments, an antibody is provided that binds to the same epitope as an anti-CD19 single domain antibody comprising the amino acid sequence of SEQ ID NO: 55. In some embodiments, an antibody is provided that binds to the same epitope as an anti-CD19 single domain antibody comprising the amino acid sequence of SEQ ID NO: 56. In some embodiments, an antibody is provided that binds to the same epitope as an anti-CD19 single domain antibody comprising the amino acid sequence of SEQ ID NO: 104

In some embodiments, provided herein is an anti-CD19 antibody, or antigen binding fragment thereof, that specifically binds to CD19 competitively with any one of the anti-CD19 single domain antibodies described herein. In some embodiments, competitive binding may be determined using an ELISA assay. For example, in some embodiments, an antibody is provided that specifically binds to CD19 competitively with an anti-CD19 single domain antibody comprising the amino acid sequence of SEQ ID NO: 43. In some embodiments, an antibody is provided that specifically binds to CD19 competitively with an anti-CD19 single domain antibody comprising the amino acid sequence of SEQ ID NO: 44. In some embodiments, an antibody is provided that specifically binds to CD19 competitively with an anti-CD19 single domain antibody comprising the amino acid sequence of SEQ ID NO: 45. In some embodiments, an antibody is provided that specifically binds to CD19 competitively with an anti-CD19 single domain antibody comprising the amino acid sequence of SEQ ID NO: 46. In some embodiments, an antibody is provided that specifically binds to CD19 competitively with an anti-CD19 single domain antibody comprising the amino acid sequence of SEQ ID NO: 47. In some embodiments, an antibody is provided that specifically binds to CD19 competitively with an anti-CD19 single domain antibody comprising the amino acid sequence of SEQ ID NO: 48. In some embodiments, an antibody is provided that specifically binds to CD19 competitively with an anti-CD19 single domain antibody comprising the amino acid sequence of SEQ ID NO: 49. In some embodiments, an antibody is provided that specifically binds to CD19 competitively with an anti-CD19 single domain antibody comprising the amino acid sequence of SEQ ID NO: 51. In some embodiments, an antibody is provided that specifically binds to CD19 competitively with an anti-CD19 single domain antibody comprising the amino acid sequence of SEQ ID NO: 52. In some embodiments, an antibody is provided that specifically binds to CD19 competitively with an anti-CD19 single domain antibody comprising the amino acid sequence of SEQ ID NO: 53. In some embodiments, an antibody is provided that specifically binds to CD19 competitively with an anti-CD19 single domain antibody comprising the amino acid sequence of SEQ ID NO: 54. In some embodiments, an antibody is provided that specifically binds to CD19 competitively with an anti-CD19 single domain antibody comprising the amino acid sequence of SEQ ID NO: 55. In some embodiments, an antibody is provided that specifically binds to CD19 competitively with an anti-CD19 single domain antibody comprising the amino acid sequence of SEQ ID NO: 56. In some embodiments, an antibody is provided that specifically binds to CD19 competitively with an anti-CD19 single domain antibody comprising the amino acid sequence of SEQ ID NO: 104.

In some embodiments, provided herein is a CD19 binding protein comprising any one of the anti-CD19 single domain antibodies described above. In some embodiments, the CD19 binding protein is a monoclonal antibody, including a camelid, chimeric, humanized or human antibody. In some embodiments, the anti-CD19 antibody is an antibody fragment, e.g., a VHH fragment. In some embodiments, the anti-CD19 antibody is a full-length heavy-chain only antibody comprising an Fc region of any antibody class or isotype, such as IgG1 or IgG4. In some embodiments, the Fc region has reduced or minimized effector function. In some embodiments, the CD19 binding protein is a fusion protein comprising the anti-CD19 single domain antibody provided herein. In other embodiments, the CD19 binding protein is a multispecific antibody comprising the anti-CD19 single domain antibody provided herein. Other exemplary CD19 binding molecules are described in more detail in the following sections.

In some embodiments, the anti-CD19 antibody (such as anti-CD19 single domain antibody) or antigen binding protein according to any of the above embodiments may incorporate any of the features, singly or in combination, as described in Sections 5.2.2 to 5.2.7 below.

5.2.2. Humanized Single Domain Antibodies

The single domain antibodies described herein include humanized single domain antibodies. General strategies to humanize single domain antibodies from Camelidae species have been described (see, e.g., Vincke et al., J. Biol. Chem., 284(5):3273-3284 (2009)) and may be useful for producing humanized VHH domains as disclosed herein. The design of humanized single domain antibodies from Camelidae species may include the hallmark residues in the VHH, such as residues 11, 37, 44, 45 and 47 (residue numbering according to Kabat) (Muyldermans, Reviews Mol Biotech 74:277-302 (2001).

Humanized antibodies, such as the humanized single domain antibodies disclosed herein can also be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, Molecular Immunology 28(4/5): 489-498 (1991); Studnicka et al., Protein Engineering 7(6): 805-814 (1994); and Roguska et al., PNAS 91:969-973 (1994)), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

In some embodiments, single domain antibodies provided herein can be humanized single domain antibodies that bind to CD19, including human CD19. For example, humanized single chain antibodies of the present disclosure may comprise one or more CDRs set forth in SEQ ID NOs: 43-49, 51-56, and 104. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., Nature 321:522-25 (1986); Riechmann et al., Nature 332:323-27 (1988); and Verhoeyen et al., Science 239:1534-36 (1988)), by substituting hypervariable region sequences for the corresponding sequences of a human antibody. In a specific embodiment, humanization of the single domain antibody provided herein is performed as described in Section 6 below.

In some cases, the humanized antibodies are constructed by CDR grafting, in which the amino acid sequences of the CDRs of the parent non-human antibody are grafted onto a human antibody framework. For example, Padlan et al. determined that only about one third of the residues in the CDRs actually contact the antigen, and termed these the "specificity determining residues," or SDRs (Padlan et al., FASEB J. 9:133-39 (1995)). In the technique of SDR grafting, only the SDR residues are grafted onto the human antibody framework (see. e.g., Kashmiri et al., Methods 36:25-34 (2005)).

The choice of human variable domains to be used in making the humanized antibodies can be important to reduce antigenicity. For example, according to the so-called "best-fit" method, the sequence of the variable domain of a non-human antibody is screened against the entire library of known human variable-domain sequences. The human sequence that is closest to that of the non-human antibody may be selected as the human framework for the humanized antibody (Sims et al., J. Immunol. 151:2296-308 (1993); and Chothia et al., J. Mol. Biol. 196:901-17 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA 89:4285-89 (1992); and Presta et al., J. Immunol. 151:2623-32 (1993)). In some cases, the framework is derived from the consensus sequences of the most abundant human subclasses, $V_L6$ subgroup I ($V_L6I$) and $V_H$ subgroup III ($V_HIII$). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., J. Immunol. 169:1119-25 (2002)).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, Protein Eng. 13:819-24 (2002)), Modeller (Sali and Blundell, J. Mol. Biol. 234:779-815 (1993)), and Swiss PDB Viewer (Guex and Peitsch, Electrophoresis 18:2714-23 (1997)). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., Mol. Immunol. 44:1986-98 (2007)).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see. e.g., Hoogenboom, Nat. Biotechnol. 23:1105-16 (2005); Dufner et al., Trends Biotechnol. 24:523-29 (2006); Feldhaus et al., Nat. Biotechnol. 21:163-70 (2003); and Schlapschy et al., Protein Eng. Des. Sel. 17:847-60 (2004)).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, J. Mol. Biol. 224:487-99 (1992)), or from the more limited set of target residues identified by Baca et al. J. Biol. Chem. 272:10678-84 (1997).

In FR shuffling, whole FRs are combined with the non-human CDRs instead of creating combinatorial libraries of selected residue variants (see, e.g., Dall'Acqua et al., Methods 36:43-60 (2005)). A one-step FR shuffling process may be used. Such a process has been shown to be efficient, as the resulting antibodies exhibited improved biochemical and physicochemical properties including enhanced expression, increased affinity, and thermal stability (see, e.g., Damschroder et al., Mol. Immunol. 44:3049-60 (2007)).

The "humaneering" method is based on experimental identification of essential minimum specificity determinants (MSDs) and is based on sequential replacement of non-human fragments into libraries of human FRs and assessment of binding. This methodology typically results in epitope retention and identification of antibodies from multiple subclasses with distinct human V-segment CDRs.

The "human engineering" method involves altering a non-human antibody or antibody fragment by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering 7:805-14 (1994); U.S. Pat. Nos. 5,766,886; 5,770,196; 5,821,123; and 5,869,619; and PCT Publication WO 93/11794.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody.

A deimmunized antibody is an antibody in which T-cell epitopes have been removed. Methods for making deimmunized antibodies have been described. See, e.g., Jones et al., Methods Mol Biol. 525:405-23 (2009), xiv, and De Groot et al., Cell. Immunol. 244:148-153(2006)). Deimmunized antibodies comprise T-cell epitope-depleted variable regions and human constant regions. Briefly, variable regions of an antibody are cloned and T-cell epitopes are subsequently identified by testing overlapping peptides derived from the variable regions of the antibody in a T cell proliferation assay. T cell epitopes are identified via in silico methods to identify peptide binding to human MHC class II. Mutations are introduced in the variable regions to abrogate binding to human MHC class II. Mutated variable regions are then utilized to generate the deimmunized antibody.

5.2.3. Single Domain Antibody Variants

In some embodiments, amino acid sequence modification(s) of the single domain antibodies that bind to CD19 described herein are contemplated. For example, it may be desirable to optimize the binding affinity and/or other biological properties of the antibody, including but not limited to specificity, thermostability, expression level, effector functions, glycosylation, reduced immunogenicity, or solubility. Thus, in addition to the single domain antibodies that bind to CD19 described herein, it is contemplated that variants of the single domain antibodies that bind to CD19 described herein can be prepared. For example, single domain antibody variants can be prepared by introducing appropriate nucleotide changes into the encoding DNA, and/or by synthesis of the desired antibody or polypeptide. Those skilled in the art who appreciate that amino acid changes may alter post-translational processes of the single domain antibody.

Chemical Modifications

In some embodiments, the single domain antibodies provided herein are chemically modified, for example, by the covalent attachment of any type of molecule to the single domain antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, or conjugation to one or more immunoglobulin domains (e.g., Fc or a portion of an Fc). Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

When the single domain antibody provided herein is fused to an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See. e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the binding molecules provided herein may be made in order to create variants with certain improved properties.

In other embodiments, when the single domain antibody provided herein is fused to an Fc region, antibody variants provided herein may have a carbohydrate structure that lacks fucose attached (directly or indirectly) to said Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about 3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

The binding molecules comprising a single domain antibody provided herein are further provided with bisected oligosaccharides, e.g., in which a biantennary oligosaccharide attached to the Fc region is bisected by GlcNAc. Such variants may have reduced fucosylation and/or improved ADCC function. Examples of such variants are described, e.g., in WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such variants may have improved CDC function. Such variants are described, e.g., in WO 1997/30087; WO 1998/58964; and WO 1999/22764.

In molecules that comprise the present single domain antibody and an Fc region, one or more amino acid modifications may be introduced into the Fc region, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates variants that possesses some but not all effector functions, which make it a desirable candidate for applications in which the half life of the binding molecule in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the binding molecule lacks FcγR binding (hence likely lacking ADCC activity), but retains FcRn binding ability. Non-limiting examples of in vitro assays to assess ADCC activity of a molecule of interest is described in U.S. Pat. No. 5,500,362 (see. e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96 non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., Blood 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Binding molecules with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, a variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Binding molecules with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those molecules comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

In some embodiments, it may be desirable to create cysteine engineered antibodies, in which one or more residues of an antibody are substituted with cysteine residues. In some embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein.

Substitutions, Deletions, or Insertions

Variations may be a substitution, deletion, or insertion of one or more codons encoding the single domain antibody or polypeptide that results in a change in the amino acid sequence as compared with the original antibody or polypeptide. Sites of interest for substitutional mutagenesis include the CDRs and FRs.

Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the parental antibodies.

Amino acid sequence insertions include amino- and/or carboxyl-terminal fusions ranging in length from one residue to polypeptides containing multiple residues, as well as intrasequence insertions of single or multiple amino acid residues. Examples of terminal insertions include an antibody with an N-terminal methionyl residue.

Single domain antibodies generated by conservative amino acid substitutions are included in the present disclosure. In a conservative amino acid substitution, an amino acid residue is replaced with an amino acid residue having a side chain with a similar charge. As described above, families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined. Conservative (e.g., within an amino acid group with similar properties and/or side chains) substitutions may be made, so as to maintain or not significantly change the properties. Exemplary substitutions are shown in Table 3 below.

TABLE 3

Amino Acid Substitutions

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to similarities in the properties of their side chains (see, e.g., Lehninger, *Biochemistry* 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. For example, any cysteine residue not involved in maintaining the proper conformation of the single domain antibody also may be substituted, for example, with another amino acid, such as alanine or serine, to improve the oxidative stability of the molecule and to prevent aberrant crosslinking. Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant antibody or fragment thereof being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. More detailed description regarding affinity maturation is provided in the section below.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant VHH sequences provided herein, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells, *Science,* 244:1081-1085 (1989). In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

The variations can be made using methods known in the art such as oligonucleotide-mediated (site-directed) mutagenesis, alanine scanning, and PCR mutagenesis. Site-directed mutagenesis (see. e.g., Carter, Biochem J. 237:1-7 (1986); and Zoller et al., Nucl. Acids Res. 10:6487-500 (1982)), cassette mutagenesis (see, e.g., Wells et al., Gene 34:315-23 (1985)), or other known techniques can be performed on the cloned DNA to produce the single domain antibody variant DNA.

5.2.4. In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed on the surface of an organism (e.g., phage, bacteria, yeast, or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review, see, for example, Hoogenboom, Methods. Mol. Biol. 178:1-37 (2002); and Bradbury and Marks, J. Immunol. Methods 290:29-49 (2004).

In a yeast display system (see. e.g., Boder et al., Nat. Biotech. 15:553-57 (1997); and Chao et al., Nat. Protocols 1:755-68 (2006)), the antibody may be fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the single chain antibody (e.g., scFv). Expression has been shown to correlate with the stability of the displayed protein, and thus antibodies can be selected for improved stability as well as affinity (see, e.g., Shusta et al., J. Mol. Biol. 292:949-56 (1999)). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., Gene 342:211-18 (2004)).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand.

The ribosome-bound mRNA is then reverse transcribed back into cDNA, which can then undergo mutagenesis and be used in the next round of selection (see. e.g., Fukuda et al., Nucleic Acids Res. 34:e127 (2006)). In mRNA display, a covalent bond between antibody and mRNA is established using puromycin as an adaptor molecule (Wilson et al., Proc. Natl. Acad. Sci. USA 98:3750-55 (2001)).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

In some embodiments, mammalian display systems may be used.

Diversity may also be introduced into the CDRs of the antibody libraries in a targeted manner or via random introduction. The former approach includes sequentially targeting all the CDRs of an antibody via a high or low level of mutagenesis or targeting isolated hot spots of somatic hypermutations (see, e.g., Ho et al., J. Biol. Chem. 280:607-17 (2005)) or residues suspected of affecting affinity on experimental basis or structural reasons. Diversity may also be introduced by replacement of regions that are naturally diverse via DNA shuffling or similar techniques (see, e.g., Lu et al., J. Biol. Chem. 278:43496-507 (2003); U.S. Pat. Nos. 5,565,332 and 6,989,250). Alternative techniques target hypervariable loops extending into framework-region residues (see, e.g., Bond et al., J. Mol. Biol. 348:699-709 (2005)) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, single domain antibodies can be immobilized onto solid supports, columns, pins, or cellulose/poly (vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, Nature Biotechnology 23:1105-16 (2005); Quiroz and Sinclair, Revista Ingeneria Biomedia 4:39-51 (2010); and references therein.

5.2.5. Modifications of Single Domain Antibodies

Covalent modifications of single domain antibodies are included within the scope of the present disclosure. Covalent modifications include reacting targeted amino acid residues of a single domain antibody with an organic derivatizing agent that is capable of reacting with selected side chains or the N- or C-terminal residues of the single domain antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see. e.g., Creighton, *Proteins: Structure and Molecular Properties* 79-86 (1983)), acetylation of the N-terminal amine, and amidation of any C-terminal carboxyl group.

Other types of covalent modification of the single domain antibody included within the scope of this present disclosure include altering the native glycosylation pattern of the antibody or polypeptide as described above (see, e.g., Beck et al., Curr. Pharm. Biotechnol. 9:482-501 (2008); and Walsh, Drug Discov. Today 15:773-80 (2010)), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192; or 4,179,337. The single domain antibody that binds to CD19 of the disclosure may also be genetically fused or conjugated to one or more immunoglobulin constant regions or portions thereof (e.g., Fc) to extend half-life and/or to impart known Fc-mediated effector functions.

The single chain antibody that binds to CD19 of the present disclosure may also be modified to form chimeric molecules comprising the single chain antibody that binds to CD19 fused to another, heterologous polypeptide or amino acid sequence, for example, an epitope tag (see, e.g., Terpe, Appl. Microbiol. Biotechnol. 60:523-33 (2003)) or the Fc region of an IgG molecule (see. e.g., Aruffo, *Antibody Fusion Proteins* 221-42 (Chamow and Ashkenazi eds., 1999)). The single chain antibody that binds to CD19 may also be used to generate CD19 binding chimeric antigen receptor (CAR), as described in more detail below.

Also provided herein are fusion proteins comprising the single chain antibody that binds to CD19 of the disclosure and a heterologous polypeptide. In some embodiments, the heterologous polypeptide to which the antibody is genetically fused or chemically conjugated is useful for targeting the antibody to cells having cell surface-expressed CD19.

Also provided herein are panels of antibodies that bind to a CD19 antigen. In specific embodiments, the panels of antibodies have different association rates, different dissociation rates, different affinities for a CD19 antigen, and/or different specificities for a CD19 antigen. In some embodiments, the panels comprise or consist of about 10 to about 1000 antibodies or more. Panels of antibodies can be used, for example, in 96-well or 384-well plates, for assays such as ELISAs.

5.2.6. Preparation of Single Domain Antibodies

Methods of preparing single domain antibodies have been described. See, e.g., Els Pardon et al, *Nature Protocol,* 9(3): 674 (2014). Single domain antibodies (such as VHHs) may be obtained using methods known in the art such as by immunizing a Camelid species (such as camel or llama) and obtaining hybridomas therefrom, or by cloning a library of single domain antibodies using molecular biology techniques known in the art and subsequent selection by ELISA with individual clones of unselected libraries or by using phage display.

Single domain antibodies provided herein may be produced by culturing cells transformed or transfected with a vector containing a single domain antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells or B cells. Alternatively, polynucleotides can be synthesized using nucleotide synthesizer or PCR techniques.

Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., *Antibody Engineering: Producing antibodies in Escherichia coli: From PCR to fermentation* 203-52 (McCafferty et al. eds., 1996); Kwong and Rader, *E. coli Expression and Purification of Fab Antibody Fragments*, in *Current Protocols in Protein Science* (2009); Tachibana and Takekoshi, *Production of Antibody Fab Fragments in Escherichia coli*, in *Antibody Expression and Production* (Al-Rubeai ed., 2011); and *Therapeutic Monoclonal Antibodies: From Bench to Clinic* (An ed., 2009).

It is, of course, contemplated that alternative methods, which are well known in the art, may be employed to prepare anti-CD19 single domain antibodies. For instance, the appropriate amino acid sequence, or portions thereof, may be produced by direct peptide synthesis using solid-phase techniques (see. e.g., Stewart et al., *Solid-Phase Peptide Synthesis* (1969); and Merrifield, J. Am. Chem. Soc. 85:2149-54 (1963)). In vitro protein synthesis may be performed using manual techniques or by automation. Various portions of the anti-CD19 antibody may be chemically synthesized separately and combined using chemical or enzymatic methods to produce the desired anti-CD19 antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Specifically, the single domain antibodies, or other CD19 binders provided herein, can be generated by immunizing llamas, performing single B-cell sorting, undertaking V-gene extraction, cloning the CD19 binders, such as VHH-Fc fusions, and then performing small scale expression and purification. Additional screening of the single domain antibodies and other molecules that bind to CD19 can be performed, including one or more of selecting for ELISA-positive, BLI-positive, and $K_D$ less than 100 nM. These selection criteria can be combined as described in Section 6 below. Additionally, individual VHH binders (and other molecules that bind to CD19) can be assayed for their ability to bind to cells expressing CD19. Such assay can be performed using FACS analysis with cells expressing CD19, and measuring the mean fluorescence intensity (MFI) of fluorescently-labeled VHH molecules. Various aspects mentioned above are described in more details below.

Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

For example, the animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*. 256:495 (1975), or may be made by recombinant DNA methods (U.S. Pat. No. 4,816,567).

In the hybridoma method, an appropriate host animal is immunized to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Goding, *Monoclonal Antibodies: Principles and Practice*, Academic Press (1986), pp. 59-103. Immortalized cell lines are usually transformed mammalian cells. The hybridoma cells thus prepared are seeded and grown in a suitable culture medium that preferably contains one or more substances that inhibit the growth or survival of the unfused, parental myeloma cells. Preferred immortalized myeloma cells are those that fuse efficiently, support stable high-level production of antibody by the selected antibody-producing cells, and are sensitive to a medium such as HAT medium.

Culture medium in which hybridoma cells are growing is assayed for production of monoclonal antibodies directed against the antigen. The culture medium in which the hybridoma cells are cultured can be assayed for the presence of monoclonal antibodies directed against the desired antigen. Such techniques and assays are known in the in art. For example, binding affinity may be determined by the Scatchard analysis of Munson et al., *Anal. Biochem.,* 107.220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.,* 5:256-262 (1993) and Pliickthun, *Immunol. Revs.* 130:151-188 (1992).

In a further embodiment, antibodies can be isolated from antibody phage libraries generated using the techniques described in McCafferty et al., *Nature.* 348:552-554 (1990). Clackson et al., *Nature.* 352:624-628 (1991) and Marks et al., *J. Mol. Biol.,* 222:581-597 (1991). Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence (U.S. Pat. No. 4,816,567: Morrison, et al., *Proc. Natl Acad. Sci. USA,* 81:6851 (1984)), or by covalently joining to the coding sequence all or part of the coding sequence for a non-immunoglobulin polypeptide. Such non-immunoglobulin polypeptides can be substituted to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Recombinant Production in Prokaryotic Cells

Polynucleic acid sequences encoding the antibodies of the present disclosure can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to, an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the present antibody by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target peptide (Siebenlist et al. *Cell* 20: 269 (1980)) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence can be substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

In some embodiments, the production of the antibodies according to the present disclosure can occur in the cytoplasm of the host cell, and therefore does not require the presence of secretion signal sequences within each cistron. Certain host strains (e.g., the *E. coli* $trxB^-$ strains) provide cytoplasm conditions that are favorable for disulfide bond formation, thereby permitting proper folding and assembly of expressed protein subunits.

Prokaryotic host cells suitable for expressing the antibodies of the present disclosure include Archaebacteria and Eubacteria, such as Gram-negative or Gram-positive organisms. Examples of useful bacteria include *Escherichia* (e.g., *E. coli*), *Bacilli* (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In some embodiments, gram-negative cells are used. In one embodiment, *E. coli* cells are used as hosts. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A(nmpc-fepE) degP41 $kan^R$(U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures and pHs.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* 263:133-147 (2002)). A variety of other inducers may be used, according to the vector construct employed, as is known in the art.

The expressed antibodies of the present disclosure are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. To improve the production yield and quality of the antibodies of the present disclosure, various fermentation conditions can be modified. For example, the chaperone proteins have been demonstrated to facilitate the proper folding and solubility of heterologous proteins produced in bacterial host cells. Chen et al. *J Bio Chem* 274:19601-19605 (1999); U.S. Pat. Nos. 6,083,715; 6,027,888; Bothmann and Pluckthun, J. Biol. Chem. 275: 17100-17105 (2000); Ramm and Pluckthun, J. Biol. Chem. 275:17106-17113 (2000); Arie et al., *Mol. Microbiol.* 39:199-210 (2001).

To minimize proteolysis of expressed heterologous proteins (especially those that are proteolytically sensitive), certain host strains deficient for proteolytic enzymes can be used for the present invention, as described in, for example, U.S. Pat. Nos. 5,264,365; 5,508,192; Hara et al., *Microbial Drug Resistance.* 2:63-72 (1996). *E. coli* strains deficient for proteolytic enzymes and transformed with plasmids overexpressing one or more chaperone proteins may be used as host cells in the expression system encoding the antibodies of the present application.

The antibodies produced herein can be further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75. Protein A immobilized on a solid phase for example can be used in some embodiments for immunoaffinity purification of binding molecules of the present disclosure. The solid phase to which Protein A is immobilized is preferably a column comprising a glass or silica surface, more preferably a controlled pore glass column or a silicic acid column. In some embodiments, the column has been coated with a reagent, such as glycerol, in an attempt to prevent nonspecific adherence of contaminants. The solid phase is then washed to remove contaminants non-specifically bound to the solid phase. Finally the antibodies of interest is recovered from the solid phase by elution.

Recombinant Production in Eukaryotic Cells

For eukaryotic expression, the vector components generally include, but are not limited to, one or more of the following, a signal sequence, an origin of replication, one or more marker genes, and enhancer element, a promoter, and a transcription termination sequence.

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region can be ligated in reading frame to DNA encoding the antibodies of the present application.

Generally, the origin of replication component is not needed for mammalian expression vectors (the SV40 origin may typically be used only because it contains the early promoter).

Expression and cloning vectors may contain a selection gene, also termed a selectable marker. Selection genes may encode proteins that confer resistance to antibiotics or other toxins, e.g., ampicillin, neomycin, methotrexate, or tetracycline; complement auxotrophic deficiencies; or supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application. For example, cells transformed with the DHFR selection gene are first identified by culturing all of the transformants in a culture medium that contains methotrexate (Mtx), a competitive antagonist of DHFR An exemplary appropriate host cell when wild-type DHFR is employed is the Chinese hamster ovary (CHO) cell line deficient in DHFR activity. Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic.

Expression and cloning vectors usually contain a promoter that is recognized by the host organism and is operably linked to the nucleic acid encoding the desired polypeptide sequences. Eukaryotic genes have an AT-rich region located approximately 25 to 30 based upstream from the site where transcription is initiated. Another sequence found 70 to 80 bases upstream from the start of the transcription of many genes may be included. The 3' end of most eukaryotic may be the signal for addition of the poly A tail to the 3' end of the coding sequence. All of these sequences may be inserted into eukaryotic expression vectors.

Polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding the antibodies of the present disclosure by higher eukaryotes is often increased by inserting an enhancer sequence into the vector. Many enhancer sequences are now known from mammalian genes (globin, elastase, albumin, α-fetoprotein, and insulin). Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

Expression vectors used in eukaryotic host cells (yeast, fungi, insect, plant, animal, human, or nucleated cells from other multicellular organisms) also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region.

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells can be transformed with the above-described expression or cloning vectors for antibodies production and cultured in conventional nutrient media modified as appropriate for inducing promoters, selecting transformants, or amplifying the genes encoding the desired sequences.

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The matrix to which the affinity ligand is attached is most often agarose, but other matrices are available. Mechanically stable matrices such as controlled pore glass or poly (styrene-divinyl) benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Following any preliminary purification step(s), the mixture comprising the antibody of interest and contaminants may be subjected to low pH hydrophobic interaction chromatography.

5.2.7. Binding Molecules Comprising the Single Domain Antibodies

In another aspect, provided herein is a binding molecule comprising a single domain antibody (e.g., a VHH domain against CD19) provided herein. In addition to chimeric antigen receptors (CARs) provided herein as described in Section 5.3 below, in some embodiments, a single domain antibody against CD19 provided herein is part of other binding molecules. Exemplary binding molecules of the present disclosure are described herein.

Fusion Protein

In various embodiments, the single domain antibody provided herein can be genetically fused or chemically conjugated to another agent, for example, protein-based entities. The single domain antibody may be chemically-conjugated to the agent, or otherwise non-covalently conjugated to the agent. The agent can be a peptide or antibody (or a fragment thereof).

Thus, in some embodiments, provided herein are single domain antibodies (e.g., VHH domains) that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, about 100, about 150, about 200, about 250, about 300, about 350, about 400, about 450 or about 500 amino acids, or over 500 amino acids) to generate fusion proteins, as well as uses thereof. In particular, provided herein are fusion proteins comprising an antigen-binding fragment of the single domain antibody provided herein (e.g., CDR1, CDR2, and/or CDR3) and a heterologous protein, polypeptide, or peptide.

Moreover, antibodies provided herein can be fused to marker or "tag" sequences, such as a peptide, to facilitate purification. In specific embodiments, the marker or tag amino acid sequence is a hexa-histidine peptide, hemagglutinin ("HA") tag, and "FLAG" tag.

Methods for fusing or conjugating moieties (including polypeptides) to antibodies are known (see, e.g., Amon et al., Monoclonal Antibodies for Immunotargeting of Drugs in Cancer Therapy, in Monoclonal Antibodies and Cancer Therapy 243-56 (Reisfeld et al. eds., 1985); Hellstrom et al., Antibodies for Drug Delivery, in Controlled Drug Delivery 623-53 (Robinson et al. eds., 2d ed. 1987); Thorpe, Antibody Carriers of Cytotoxic Agents in Cancer Therapy: A Review, in Monoclonal Antibodies: Biological and Clinical Applications 475-506 (Pinchera et al. eds., 1985); Analysis, Results, and Future Prospective of the Therapeutic Use of Radiolabeled Antibody in Cancer Therapy, in Monoclonal Antibodies for Cancer Detection and Therapy 303-16 (Baldwin et al. eds., 1985); Thorpe et al., Immunol. Rev. 62:119-58 (1982); U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-39 (1991); Traunecker et al., Nature, 331:84-86 (1988); Zheng et al., J. Immunol. 154:5590-600 (1995); and Vil et al., Proc. Natl. Acad. Sci. USA 89:11337-41 (1992)).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the single domain antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., Curr. Opinion Biotechnol. 8:724-33 (1997); Harayama, Trends Biotechnol. 16(2):76-82 (1998); Hansson et al., J. Mol. Biol. 287:265-76 (1999); and Lorenzo and Blasco, Biotechniques 24(2):308-13 (1998)). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

In some embodiments, a single domain antibody provided herein (e.g., VHH domain) is conjugated to a second antibody to form an antibody heteroconjugate.

In various embodiments, the single domain antibody is genetically fused to the agent. Genetic fusion may be accomplished by placing a linker (e.g., a polypeptide) between the single domain antibody and the agent. The linker may be a flexible linker.

In various embodiments, the single domain antibody is genetically conjugated to a therapeutic molecule, with a hinge region linking the single domain antibody to the therapeutic molecule.

Also provided herein are methods for making the various fusion proteins provided herein. The various methods described in Section 5.2.6 above may also be utilized to make the fusion proteins provided herein.

In a specific embodiment, the fusion protein provided herein is recombinantly expressed. Recombinant expression of a fusion protein provided herein may require construction of an expression vector containing a polynucleotide that encodes the protein or a fragment thereof. Once a polynucleotide encoding a protein provided herein or a fragment thereof has been obtained, the vector for the production of the molecule may be produced by recombinant DNA technology using techniques well-known in the art. Thus, methods for preparing a protein by expressing a polynucleotide containing an encoding nucleotide sequence are described herein. Methods which are well known to those skilled in the art can be used to construct expression vectors containing coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a fusion protein provided herein, or a fragment thereof, or a CDR, operably linked to a promoter.

The expression vector can be transferred to a host cell by conventional techniques and the transfected cells are then cultured by conventional techniques to produce a fusion protein provided herein. Thus, also provided herein are host cells containing a polynucleotide encoding a fusion protein provided herein or fragments thereof operably linked to a heterologous promoter.

A variety of host-expression vector systems may be utilized to express the fusion protein provided herein. Such host-expression systems represent vehicles by which the coding sequences of interest may be produced and subsequently purified, but also represent cells which may, when transformed or transfected with the appropriate nucleotide coding sequences, express a fusion protein provided herein in situ. These include but are not limited to microorganisms such as bacteria (e.g., *E. coli* and *B. subtilis*) transformed with recombinant bacteriophage DNA, plasmid DNA or cosmid DNA expression vectors containing coding sequences; yeast (e.g., *Saccharomyces Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant fusion protein. For example, mammalian cells such as Chinese hamster ovary cells (CHO), in conjunction with a vector such as the major intermediate early gene promoter element from human cytomegalovirus is an effective expression system for antibodies or variants thereof. In a specific embodiment, the expression of nucleotide sequences encoding the fusion proteins provided herein is regulated by a constitutive promoter, inducible promoter or tissue specific promoter.

In bacterial systems, a number of expression vectors may be advantageously selected depending upon the use intended for the fusion protein being expressed. For example, when a large quantity of such a fusion protein is to be produced, for the generation of pharmaceutical compositions of a fusion protein, vectors which direct the expression of high levels of fusion protein products that are readily purified may be desirable. Such vectors include, but are not limited to, the *E. coli* expression vector pUR278 (Ruther et al., EMBO 12:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region El or E3) will result in a recombinant virus that is viable and capable of expressing the fusion protein in infected hosts (e.g., see Logan & Shenk, Proc. Natl. Acad. Sci. USA 8 1:355-359 (1984)). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT20 and T47D, NS0 (a murine myeloma cell line that does not endogenously produce any immunoglobulin chains), CRL7030 and HsS78Bst cells.

For long-term, high-yield production of recombinant proteins, stable expression can be utilized. For example, cell lines which stably express the fusion proteins may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the fusion protein. Such engineered cell lines may be particularly useful in screening and evaluation of compositions that interact directly or indirectly with the binding molecule.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8-17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIB TECH 11(5):155-2 15 (1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., J. Mol. Biol. 150:1 (1981), which are incorporated by reference herein in their entireties.

The expression level of a fusion protein can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing a fusion protein is amplifiable, increase in the level of inhibitor present in culture of host cell will increase the number of copies of the marker gene. Since the amplified region is associated with the fusion protein gene, production of the fusion protein will also increase (Crouse et al., *Mol. Cell. Biol.* 3:257 (1983)).

The host cell may be co-transfected with multiple expression vectors provided herein. The vectors may contain identical selectable markers which enable equal expression of respective encoding polypeptides. Alternatively, a single vector may be used which encodes, and is capable of expressing multiple polypeptides. The coding sequences may comprise cDNA or genomic DNA.

Once a fusion protein provided herein has been produced by recombinant expression, it may be purified by any method known in the art for purification of a polypeptide (e.g., an immunoglobulin molecule), for example, by chromatography (e.g., ion exchange, affinity, particularly by affinity for the specific antigen after Protein A, sizing column chromatography, and Kappa select affinity chromatography), centrifugation, differential solubility, or by any other standard technique for the purification of proteins. Further, the fusion protein molecules provided herein can be fused to heterologous polypeptide sequences described herein or otherwise known in the art to facilitate purification.

Immunoconjugates

In some embodiments, the present disclosure also provides immunoconjugates comprising any of the antibodies (such as anti-CD19 single domain antibodies) described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate comprises an antibody as described herein conjugated to a radioactive atom to form a radioconjugate. A variety of radioactive isotopes are available for the production of radioconjugates. Examples include $At^{211}$, $I^{311}$, $I^{125}$, $Y^{90}$, $Re^{186}$, $Re^{188}$, $Sm^{13}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers, thioether linkers, or hydrophilic linkers designed to evade multidrug transporter-mediated resistance.

The immunoconjugates or ADCs herein contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

In other embodiments, antibodies provided herein are conjugated or recombinantly fused, e.g., to a diagnostic molecule. Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, 225Acγ-emitting, Auger-emitting, O-emitting, an alpha-emitting or positron-emitting radioactive isotope.

5.3. Chimeric Antigen Receptors

In another aspect, provided herein is a chimeric antigen receptor (CAR) comprising an extracellular antigen binding domain comprising a single domain antibody (e.g., VHH) provided herein that binds to CD19. Exemplary CARs comprising the present VHH domains (i.e., VHH-based CARs) are illustrated and compared with conventional CARs comprising scFvs (i.e., scFv-based CARs) as described in Section 6 below.

In some embodiments, the chimeric antigen receptor (CAR) provided herein comprises a polypeptide comprising: (a) an extracellular antigen binding domain comprising a single domain antibody (sdAb) specifically binding to CD19 as provided herein, and optionally one or more additional binding domain(s); (b) a transmembrane domain; and (c) an intracellular signaling domain. Each components and additional regions are described in more detail below.

5.3.1. Extracellular Antigen Binding Domain

The extracellular antigen binding domain of the CARs described herein comprises one or more (such as any one of 1, 2, 3, 4, 5, 6 or more) single domain antibodies. The single domain antibodies can be fused to each other directly via peptide bonds, or via peptide linkers.

Single Domain Antibodies

The CARs of the present disclosure comprise an extracellular antigen binding domain comprising one or more single domain antibodies. The sdAbs may be of the same or different origins, and of the same or different sizes. Exemplary sdAbs include, but are not limited to, heavy chain variable domains from heavy-chain only antibodies (e.g., VHH or $V_{NAR}$), binding molecules naturally devoid of light chains, single domains (such as $V_H$ or $V_L$) derived from conventional 4-chain antibodies, humanized heavy-chain only antibodies, human single domain antibodies produced by transgenic mice or rats expressing human heavy chain segments, and engineered domains and single domain scaffolds other than those derived from antibodies. Any sdAbs known in the art or developed by the present disclosure, including the single domain antibodies described above in the present disclosure, may be used to construct the CARs described herein. The sdAbs may be derived from any species including, but not limited to mouse, rat, human, camel, llama, lamprey, fish, shark, goat, rabbit, and bovine. Single domain antibodies contemplated herein also include naturally occurring single domain antibody molecules from species other than Camelidae and sharks.

In some embodiments, the sdAb is derived from a naturally occurring single domain antigen binding molecule known as heavy chain antibody devoid of light chains (also referred herein as "heavy chain only antibodies"). Such single domain molecules are disclosed in WO 94/04678 and Hamers-Casterman, C. et al., *Nature* 363:446-448 (1993), for example. For clarity reasons, the variable domain derived from a heavy chain molecule naturally devoid of light chain is known herein as a VHH to distinguish it from the conventional $V_H$ of four chain immunoglobulins. Such a VHH molecule can be derived from antibodies raised in Camelidae species, for example, camel, llama, vicuna, dromedary, alpaca and guanaco. Other species besides Camelidae may produce heavy chain molecules naturally devoid of light chain, and such VHHs are within the scope of the present disclosure. In addition, humanized versions of VHHs as well as other modifications and variants are also contemplated and within the scope of the present disclosure.

VHH molecules from Camelids are about 10 times smaller than IgG molecules. They are single polypeptides and can be very stable, resisting extreme pH and temperature conditions. Moreover, they can be resistant to the action of proteases which is not the case for conventional 4-chain antibodies. Furthermore, in vitro expression of VHHs produces high yield, properly folded functional VHHs. In addition, antibodies generated in Camelids can recognize epitopes other than those recognized by antibodies generated in vitro through the use of antibody libraries or via immunization of mammals other than Camelids (see, for example, WO9749805). As such, multispecific or multivalent CARs comprising one or more VHH domains may interact more efficiently with targets than multispecific or multivalent CARs comprising antigen binding fragments derived from conventional 4-chain antibodies. Since VHHs are known to bind into "unusual" epitopes such as cavities or grooves, the affinity of CARs comprising such VHHs may be more suitable for therapeutic treatment than conventional multispecific polypeptides.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov, *Protein Sci.* 14:2901-2909 (2005).

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) VH domain from a conventional 4-chain antibody by one or more of the amino acid residues that occur at the corresponding position(s) in a VHH domain of a heavy chain antibody. This can be performed in a manner known in the field, which will be clear to the skilled person. Such "camelizing" substitutions are preferably inserted at amino acid positions that form and/or are present at the $V_H$-$V_L$ interface, and/or at the so-called Camelidae hallmark residues, as defined herein (see for example WO 94/04678, Davies and Riechmann FEBS Letters 339: 285-290 (1994); Davies and Riechmann, Protein Engineering 9 (6): 531-537 (1996); Riechmann, J. Mol. Biol. 259: 957-969 (1996); and Riechmann and Muyldermans, J. Immunol. Meth. 231: 25-38 (1999)).

In some embodiments, the sdAb is a human single domain antibody produced by transgenic mice or rats expressing human heavy chain segments. See, e.g., US20090307787, U.S. Pat. No. 8,754,287, US20150289489, US20100122358, and WO2004049794. In some embodiments, the sdAb is affinity matured.

In some embodiments, naturally occurring VHH domains against a particular antigen or target, can be obtained from (naïve or immune) libraries of Camelid VHH sequences. Such methods may or may not involve screening such a library using said antigen or target, or at least one part, fragment, antigenic determinant or epitope thereof using one or more screening techniques known in the field. Such libraries and techniques are for example described in WO 99/37681, WO 01/90190, WO 03/025020 and WO 03/035694. Alternatively, improved synthetic or semi-synthetic libraries derived from (naïve or immune) VHH libraries may be used, such as VHH libraries obtained from (naïve or immune) VHH libraries by techniques such as random mutagenesis and/or CDR shuffling, as for example described in WO 00/43507.

In some embodiments, the single domain antibodies are generated from conventional four-chain antibodies. See, for example, EP 0 368 684; Ward et al., Nature, 341 (6242): 544-6 (1989); Holt et al., Trends Biotechnol., 21(11):484-490 (2003); WO 06/030220; and WO 06/003388.

In some embodiments, the extracellular antigen binding domain provided herein comprises at least one binding domain, and the at least one binding domain comprises a single domain antibody that binds to CD19 as provided herein, e.g., the anti-CD19 single domain antibodies described in Section 5.2 above.

In some embodiments, provided herein is a CAR comprising a polypeptide comprising: (a) an extracellular antigen binding domain comprising an anti-CD19 sdAb; (b) a transmembrane domain; and (c) an intracellular signaling domain, wherein the anti-CD19 sdAb is an anti-CD19 sdAb as described in Section 5.2 above, including, e.g., the VHH domains in Table 2 and those having one, two or all three CDRs in any of those VHH domains in Table 2. In some embodiments, the anti-CD19 sdAb is camelid, chimeric, human, or humanized.

In some embodiments, provided herein is a CAR comprising a polypeptide comprising: (a) an extracellular antigen binding domain comprising an anti-CD19 sdAb; (b) a transmembrane domain; and (c) an intracellular signaling domain, wherein the anti-CD19 sdAb comprises the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56 or SEQ ID NO: 104. In other embodiments, provided herein is a CAR comprising a polypeptide comprising: (a) an extracellular antigen binding domain comprising an anti-CD19 sdAb; (b) a transmembrane domain; and (c) an intracellular signaling domain, wherein the anti-CD19 sdAb comprises an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56 or SEQ ID NO: 104.

In other embodiments, the extracellular antigen binding domain comprises two or more antigen binding domains. Among these two or more antigen binding domains, at least one is a VHH that binds to CD19 as provided herein, and one or more additional binding domain(s) that bind(s) to one or more additional antigen(s), e.g., 1, 2, 3, 4 or more additional single domain antibody binding regions (sdAbs) targeting one or more additional antigen(s).

Thus, in some embodiments, provided herein is a multi-specific (such as bispecific and trispecific) CAR comprising a polypeptide comprising: (a) an extracellular antigen binding domain comprising a first single domain antibody (sdAb) specifically binding to CD19; (b) a transmembrane domain; and (c) an intracellular signaling domain. In some embodiments, the CAR further comprises a second single domain antibody (sdAb) specifically binding to a second antigen (such as a second tumor antigen). In some embodiments, the CAR further comprises a second single domain antibody (sdAb) specifically binding to a second antigen (such as a second tumor antigen); and a third single domain antibody (sdAb) specifically binding to a third antigen (such as a third tumor antigen).

In some embodiments, the additional antigen(s) targeted by the CARs of the present disclosure are cell surface molecules. The single domain antibodies may be chosen to recognize an antigen that acts as a cell surface marker on target cells associated with a special disease state. In some embodiments, the antigen is a tumor antigen. In some embodiments, the tumor antigen is associated with a B cell malignancy. Tumors express a number of proteins that can serve as a target antigen for an immune response, particularly T cell mediated immune responses. The antigens targeted by the CAR may be antigens on a single diseased cell or antigens that are expressed on different cells that each contribute to the disease. The antigens targeted by the CAR may be directly or indirectly involved in the diseases.

Tumor antigens are proteins that are produced by tumor cells that can elicit an immune response, particularly T-cell mediated immune responses. The selection of the additional targeted antigen of the present disclosure will depend on the particular type of cancer to be treated. Exemplary tumor antigens include, but not limited to, a glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-la, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and gp100 in melanoma and prostatic acid phosphatase (PAP) and prostate-specific antigen (PSA) in prostate cancer. Other target molecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. In addition to CD19, B-cell differentiation antigens such as CD20 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include: differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7.

Other large, protein-based antigens include TSP-180, MAGE-4, MAGE-5, MAGE-6, RAGE, NY-ESO, pl85erbB2, pl80erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\PI, CO-029, FGF-5, G250, Ga733\EpCAM, HTgp-175, M344, MA-50, MG7-Ag, MOV18, NB/70K, NY-CO-1, RCAS 1, SDCCAG16, TA-90\Mac-2 binding protein\cyclophilin C-associated protein, TAAL6, TAG72, TLP, and TPS.

In some more specific embodiments, the one or more additional antigen(s) is selected from a group consisting of CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In a specific embodiment, the CAR provided herein comprises a VHH that binds to CD19 and a VHH that binds to CD20. In another specific embodiment, the CAR provided herein comprises a VHH that binds to CD19 and a VHH that binds to CD22.

In some embodiments, the sdAb provided herein is camelid, chimeric, human, or humanized.

In addition to the one or more antigen binding domain(s) provided herein, the CAR provided herein may further comprise one or more of the following: a linker (e.g., a peptide linker), a transmembrane domain, a hinge region, a signal peptide, an intracellular signaling domain, a co-stimulatory signaling domain, each of which is described in more detail below.

For example, in some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the co-stimulatory signaling domain is derived from CD137. In some embodiments, the CD19 CAR further comprises a hinge domain (such as a CD8a hinge domain) located between the C-terminus of the extracellular antigen binding domain and the N-terminus of the transmembrane domain. In some embodiments, the CD19 CAR further comprises a signal peptide (such as a CD8a signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the CD19 CAR is monospecific. In some embodiments, the CD19 CAR is monovalent.

Peptide Linkers

The various single domain antibodies in the multispecific or multivalent CARs described herein may be fused to each other via peptide linkers. In some embodiments, the single domain antibodies are directly fused to each other without any peptide linkers. The peptide linkers connecting different single domain antibodies (e.g., VHH) may be the same or different. Different domains of the CARs may also be fused to each other via peptide linkers.

Each peptide linker in a CAR may have the same or different length and/or sequence depending on the structural and/or functional features of the single domain antibodies and/or the various domains. Each peptide linker may be selected and optimized independently. The length, the degree of flexibility and/or other properties of the peptide linker(s) used in the CARs may have some influence on properties, including but not limited to the affinity, specificity or avidity for one or more particular antigens or epitopes. For example, longer peptide linkers may be selected to ensure that two adjacent domains do not sterically interfere with one another. In some embodiments, a short peptide linker may be disposed between the transmembrane domain and the intracellular signaling domain of a CAR. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include but not limited to glycine polymers $(G)_n$, glycine-serine polymers (including, for example, $(GS)_n$, $(GSGGS)_n$, $(GGGS)_n$, and $(GGGGS)_n$, where n is an integer of at least one), glycine-alanine polymers, alanine-serine polymers, and other flexible linkers known in the art. Exemplary peptide linkers are listed in the table below.

TABLE 4

Exemplary Peptide Linkers

| Sequences | SEQ ID NO |
|---|---|
| $(GS)_n$, n is an integer including, e.g., 1, 2, 3, 4, 5, and 6. | SEQ ID NO: 79 |
| $(GSGGS)_n$, n is an integer including, e.g., 1, 2, 3, 4, 5, and 6. | SEQ ID NO: 80 |
| $(GGGS)_n$, n is an integer including, e.g., 1, 2, 3, 4, 5, and 6. | SEQ ID NO: 81 |
| GGGGSGGGGSGGGGGGSGSGGGGSGGGGSGGGGS | SEQ ID NO: 82 |
| $(GGGGS)_n$, n is an integer including, e.g., 1, 2, 3, 4, 5, and 6. | SEQ ID NO: 83 |
| DGGGS | SEQ ID NO: 84 |
| TGEKP | SEQ ID NO: 85 |
| GGRR | SEQ ID NO: 86 |
| GGGGSGGGGSGGGGGGSGSGGGGS | SEQ ID NO: 87 |
| EGKSSGSGSESKVD | SEQ ID NO: 88 |
| KESGSVSSEQLAQFRS | SEQ ID NO: 89 |
| GGRRGGGS | SEQ ID NO: 90 |
| LRQRDGERP | SEQ ID NO: 91 |
| LRQKDGGGSERP | SEQ ID NO: 92 |
| LRQKDGGGSGGGSERP | SEQ ID NO: 93 |
| GSTSGSGKPGSGEGST | SEQ ID NO: 94 |
| GSTSGSGKSSEGKG | SEQ ID NO: 95 |
| KESGSVSSEQLAQFRSLD | SEQ ID NO: 96 |

Other linkers known in the art, for example, as described in WO2016014789, WO2015158671, WO2016102965, US20150299317, WO2018067992, U.S. Pat. No. 7,741,465, Colcher et al., *J. Nat. Cancer Inst.* 82:1191-1197 (1990), and Bird et al., *Science* 242:423-426 (1988) may also be included in the CARS provided herein, the disclosure of each of which is incorporated herein by reference.

5.3.2. Transmembrane Domain

The CARS of the present disclosure comprise a transmembrane domain that can be directly or indirectly fused to the extracellular antigen binding domain. The transmembrane domain may be derived either from a natural or from a synthetic source. As used herein, a "transmembrane domain" refers to any protein structure that is thermodynamically stable in a cell membrane, preferably an eukaryotic cell membrane. Transmembrane domains compatible for use in the CARS described herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. In some embodiments, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the CAR comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDl la, CD18), ICOS (CD278), 4-1BB (CD137), GITR, CD40, BAFFR, HVEM (LIGHTR), SLAMF7, NKp80 (KLRF1), CD160, CD19, IL-2R beta, IL-2R gamma, IL-7R a, ITGA1, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGB1, CD29, ITGB2, CD18, LFA-1, ITGB7, TNFR2, DNAM1 (CD226), SLAMF4 (CD244, 2B4), CD84, CD96 (Tactile), CEACAMI, CRT AM, Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8α, CD4, CD28, CD137, CD80, CD86, CD152 and PD1.

In some specific embodiments, the transmembrane domain is derived from CD8α. In some embodiments, the transmembrane domain is a transmembrane domain of CD8α comprising the amino acid sequence of SEQ ID NO: 74.

Transmembrane domains for use in the CARs described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 and PCT Publication No. WO 2000/032776, the relevant disclosures of which are incorporated by reference herein.

The transmembrane domain provided herein may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the CAR provided herein comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

5.3.3. Intracellular Signaling Domain

The CARs of the present disclosure comprise an intracellular signaling domain. The intracellular signaling domain is responsible for activation of at least one of the normal effector functions of the immune effector cell expressing the CARs. The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling domain of an immune effector cell. In some embodiments, the CAR comprises an intracellular signaling domain consisting essentially of a primary intracellular signaling domain of an immune effector cell. "Primary intracellular signaling domain" refers to cytoplasmic signaling sequence that acts in a stimulatory manner to induce immune effector functions. In some embodiments, the primary intracellular signaling domain contains a signaling motif known as immunoreceptor tyrosine-based activation motif, or ITAM. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma (FCER1G), FcR beta (Fc Epsilon Rib), CD3 gamma, CD3 delta, CD3 epsilon, CD5, CD22, CD79a, CD79b, and CD66d.

In some embodiments, the primary intracellular signaling domain is derived from CD3ζ. In some embodiments, the intracellular signaling domain consists of the cytoplasmic signaling domain of CD3ζ. In some embodiments, the primary intracellular signaling domain is a cytoplasmic signaling domain of wild-type CD3ζ. In some embodiments, the primary intracellular signaling domain of CD3ζ comprises the amino acid sequence of SEQ ID NO: 76. In some embodiments, the primary intracellular signaling domain of wild-type CD3ζ. In some embodiments, the primary intracellular signaling domain is a functional mutant of the cytoplasmic signaling domain of CD3ζ containing one or more mutations, such as Q65K.

5.3.4. Co-Stimulatory Signaling Domain

Many immune effector cells require co-stimulation, in addition to stimulation of an antigen-specific signal, to promote cell proliferation, differentiation and survival, as well as to activate effector functions of the cell. In some embodiments, the CAR comprises at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils. "Co-stimulatory signaling domain" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single co-stimulatory signaling domain. In some embodiments, the intracellular signaling domain comprises two or more (such as about any of 2, 3, 4, or more) co-stimulatory signaling domains. In some embodiments, the intracellular signaling domain comprises two or more of the same co-stimulatory signaling domains. In some embodiments, the intracellular signaling domain comprises two or more co-stimulatory signaling domains from different co-stimulatory proteins, such as any two or more co-stimulatory proteins described herein. In some embodiments, the intracellular signaling domain comprises a primary intracellular signaling domain (such as cytoplasmic signaling domain of CD3ζ) and one or more co-stimulatory signaling domains. In some embodiments, the one or more co-stimulatory signaling domains and the primary intracellular signaling domain (such as cytoplasmic signaling domain of CD3ζ) are fused to each other via optional peptide linkers. The primary intracellular signaling domain, and the one or more co-stimulatory signaling domains may be arranged in any suitable order. In some embodiments, the one or more co-stimulatory signaling domains are located between the transmembrane domain and the primary intracellular signaling domain (such as cytoplasmic signaling domain of CD3ζ). Multiple co-stimulatory signaling domains may provide additive or synergistic stimulatory effects.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the CARs described herein. The type(s) of co-stimulatory signaling domain is selected based on factors such as the type of the immune effector cells in which the effector molecules would be expressed (e.g., T cells, NK cells, macrophages, neutrophils, or eosinophils) and the desired immune effector function (e.g., ADCC effect). Examples of co-stimulatory signaling domains for use in the CARs can be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24NISTA/B7-H5, ICOS/CD278, PD-1, PD-L2/B7-DC, and PDCD6); members of the TNF superfamily (e.g., 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand/TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/

CD26, EphB6, TIM-1/KIM-1/HAVCR, TIM-4, TSLP, TSLP R, lymphocyte function associated antigen-1 (LFA-1), and NKG2C.

In some embodiments, the one or more co-stimulatory signaling domains are selected from the group consisting of CD27, CD28, CD137, OX40, CD30, CD40, CD3, lymphocyte function-associated antigen-1 (LFA-1), CD2, CD7, LIGHT, NKG2C, B7-H3 and ligands that specially bind to CD83.

In some embodiments, the intracellular signaling domain in the CAR of the present disclosure comprises a co-stimulatory signaling domain derived from CD137 (i.e., 4-1BB). In some embodiments, the intracellular signaling domain comprises a cytoplasmic signaling domain of CD3ζ and a co-stimulatory signaling domain of CD137. In some embodiments, the intracellular signaling domain comprises a co-stimulatory signaling domain of CD137 comprising the amino acid sequence of SEQ ID NO: 75. Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants. Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation.

5.3.5. Hinge Region

The CARs of the present disclosure may comprise a hinge domain that is located between the extracellular antigen binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular antigen binding domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of SEQ ID NO: 73.

Hinge domains of antibodies, such as an IgG, IgA, IgM, IgE, or IgD antibodies, are also compatible for use in the pH-dependent chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a (G×S)n linker, wherein x and n, independently can be an integer between 3 and 12, including 3, 4, 5, 6, 7, 8, 9, 10, 11, 12, or more.

5.3.6. Signal Peptide

The CARs of the present disclosure may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences, which are compatible for use in the CARs described herein will be evident to one of skill in the art. In some embodiments, the signal peptide is derived from a molecule selected from the group consisting of CD8α, GM-CSF receptor a, and IgG1 heavy chain. In some embodiments, the signal peptide is derived from CD8α. In some embodiments, the signal peptide of CD8α comprises the amino acid sequence of SEQ ID NO: 72.

5.3.7. Exemplary CARs

Exemplary CARs are generated as shown in Section 6 below, such as VHH-083 CAR, VHH-111 CAR, VHH-131 CAR, 77LICA542 CAR, 77LICA519 CAR, 77LICA602 CAR, huVHH-773 CAR, and huVHH-776 CAR.

In some embodiments, provided herein is a CAR comprising or consisting of the amino acid sequence of SEQ ID NO: 57. In some embodiments, provided herein is a CAR comprising or consisting of the amino acid sequence of SEQ ID NO: 58. In some embodiments, provided herein is a CAR comprising or consisting of the amino acid sequence of SEQ ID NO: 59. In some embodiments, provided herein is a CAR comprising or consisting of the amino acid sequence of SEQ ID NO: 60. In some embodiments, provided herein is a CAR comprising or consisting of the amino acid sequence of SEQ ID NO: 61. In some embodiments, provided herein is a CAR comprising or consisting of the amino acid sequence of SEQ ID NO: 62. In some embodiments, provided herein is a CAR comprising or consisting of the amino acid sequence of SEQ ID NO: 63. In some embodiments, provided herein is a CAR comprising or consisting of the amino acid sequence of SEQ ID NO: 105.

In certain embodiments, the CAR provided herein comprises amino acid sequences with certain percent identity relative to any one of the CARs exemplified in the Section 6 below.

In some embodiments, provided herein is a CD19 CAR comprising a polypeptide having at least 75%, 80%, 85%, 86%, 87%, 88%, 89%, 90%, 91%, 92%, 93%, 94%, 95%, %%, 97%, 98%, 99%, or 100% sequence identity to the amino acid sequence of SEQ ID NO: 57. In some embodiments, provided herein is a CD19 CAR comprising a polypeptide having at least 75%, 80%, 85%, 86%, 87%, 88%, 89%, 90%, 91%, 92%, 93%, 94%, 95%, %%, 97%, 98%, 99%, or 100% sequence identity to the amino acid sequence of SEQ ID NO: 58. In some embodiments, provided herein is a CD19 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 59. In some embodiments, provided herein is a CD19 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 60. In some embodiments, provided herein is a CD19 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 61. In some embodiments, provided herein is a CD19 CAR comprising a polypeptide having at least 75%, 80%, 85%, 86%, 87%, 88%, 89%, 90%, 91%, 92%, 93%, 94%, 95%, %%, 97%, 98%, 99%, or 100% sequence identity to the amino acid sequence of SEQ ID NO: 62. In some embodiments, provided herein is a CD19 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 63. In some embodiments, provided herein is a CD19 CAR comprising a polypeptide having at least 75%, 80%, 85%, 86%, 87%, 88%, 89%, 90%, 91%, 92%, 93%, 94%, 95%, %%, 97%, 98%, 99%, or 100% sequence identity to the amino acid sequence of SEQ ID NO: 105.

In some embodiments, provided herein is an isolated nucleic acid encoding any of the CD19 CARs provided herein. More detailed description regarding nucleic acid sequences and vectors are provided below.

5.4. Engineered Immune Effector Cells

In yet another aspect, provided herein are host cells (such as immune effector cells) comprising any one of the CARs described herein.

Thus, in some embodiments, provided herein is an engineered immune effector cell (such as T cell) comprising a CAR which comprises a polypeptide comprising: (a) an extracellular antigen binding domain comprising an anti-CD19 sdAb; (b) a transmembrane domain; and (c) an intracellular signaling domain, wherein the anti-CD19 sdAb is an anti-CD19 sdAb as described in Section 5.2 above, including, e.g., the VHH domains in Table 2 and those having one, two or all three CDRs in any of those VHH domains in Table 2. In some embodiments, the anti-CD19 sdAb is camelid, chimeric, human, or humanized. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, provided herein is an engineered immune effector cell (such as T cell) comprising a CAR which comprises a polypeptide comprising: (a) an extracellular antigen binding domain comprising an anti-CD19 sdAb; (b) a transmembrane domain; and (c) an intracellular signaling domain, wherein the anti-CD19 sdAb comprises the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56 or SEQ ID NO: 104. In some embodiments, provided herein is an engineered immune effector cell (such as T cell) comprising a CAR which comprises a polypeptide comprising: (a) an extracellular antigen binding domain comprising an anti-CD19 sdAb; (b) a transmembrane domain; and (c) an intracellular signaling domain, wherein the anti-CD19 sdAb comprises an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56 or SEQ ID NO: 104. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, provided herein is an engineered immune effector cell (such as T cell) comprising a CAR which comprises an amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, and SEQ ID NO: 105. In some embodiments, provided herein is an engineered immune effector cell (such as T cell) comprising a CAR which comprises a polypeptide having at least 75%, 80%, 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, and SEQ ID NO: 105.

In other embodiments, there is provided an engineered immune effector cell (such as T cell) comprising a multispecific (such as bispecific or trispecific) chimeric antigen receptor (CAR) comprising a polypeptide comprising: (a) an extracellular antigen binding domain comprising a first single domain antibody (sdAb) specifically binding to CD19 and one or more additional antigen binding domain(s); (b) a transmembrane domain; and (c) an intracellular signaling domain. In some embodiments, the additional antigen binding domain binds to an antigen selected from the group consisting of CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the additional sdAb is camelid, chimeric, human, or humanized. In some embodiments, the first single domain antibody and the additional single domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

Also provided are engineered immune effector cells comprising (or expressing) two or more different CARs. Any two or more of the CARs described herein may be expressed in combination. The CARs may target different antigens, thereby providing synergistic or additive effects. The two or more CARs may be encoded on the same vector or different vectors.

The engineered immune effector cell may further express one or more therapeutic proteins and/or immunomodulators, such as immune checkpoint inhibitors. See, e.g., International Patent Application NOs. PCT/CN2016/073489 and PCT/CN2016/087855, which are incorporated herein by reference in their entirety.

5.4.1. Vectors

The present disclosure provides vectors for cloning and expressing any one of the CARs described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual, Cold Spring Harbor Laboratory, New York), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying chimeric antigen receptors can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector comprises any one of the nucleic acids encoding a CAR described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present disclosure. Promoters may be roughly categorized as constitutive promoters or regulated promoters, such as inducible promoters.

In some embodiments, the nucleic acid encoding the CAR is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV) promoters, human elongation factors-1 alpha (hEF1α), ubiquitin C promoter (UbiC), phosphoglycerokinase promoter (PGK), simian virus 40 early promoter (SV40), and chicken β-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive chimeric antigen receptor expression in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the CAR is operably linked to a hEF1α promoter.

In some embodiments, the nucleic acid encoding the CAR is operably linked to an inducible promoter. Inducible promoters belong to the category of regulated promoters. The inducible promoter can be induced by one or more conditions, such as a physical condition, microenvironment of the engineered immune effector cell, or the physiological state of the engineered immune effector cell, an inducer (i.e., an inducing agent), or a combination thereof.

In some embodiments, the inducing condition does not induce the expression of endogenous genes in the engineered mammalian cell, and/or in the subject that receives the pharmaceutical composition. In some embodiments, the inducing condition is selected from the group consisting of: inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the CAR from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises more than one nucleic acid encoding CARs. In some embodiments, the vector comprises a nucleic acid comprising a first nucleic acid sequence encoding a first CAR and a second nucleic acid sequence encoding a second CAR, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A.

5.4.2. Immune Effector Cells

"Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune effector cells are T cells. In some embodiments, the T cells are CD4+/CD8−, CD4−/CD8+, CD4+/CD8+, CD4−/CD8−, or combinations thereof. In some embodiments, the T cells produce IL-2, TFN, and/or TNF upon expressing the CAR and binding to the target cells, such as CD19+ tumor cells. In some embodiments, the CD8+ T cells lyse antigen-specific target cells upon expressing the CAR and binding to the target cells.

In some embodiments, the immune effector cells are NK cells. In other embodiments, the immune effector cells can be established cell lines, for example, NK-92 cells.

In some embodiments, the immune effector cells are differentiated from a stem cell, such as a hematopoietic stem cell, a pluripotent stem cell, an iPS, or an embryonic stem cell.

The engineered immune effector cells are prepared by introducing the CARs into the immune effector cells, such as T cells. In some embodiments, the CAR is introduced to the immune effector cells by transfecting any one of the isolated nucleic acids or any one of the vectors described above. In some embodiments, the CAR is introduced to the immune effector cells by inserting proteins into the cell membrane while passing cells through a microfluidic system, such as CELL SQUEEZE® (see, e.g., U.S. Patent Application Publication No. 20140287509).

Methods of introducing vectors or isolated nucleic acids into a mammalian cell are known in the art. The vectors described can be transferred into an immune effector cell by physical, chemical, or biological methods.

Physical methods for introducing the vector into an immune effector cell include calcium phosphate precipitation, lipofection, particle bombardment, microinjection, electroporation, and the like. Methods for producing cells comprising vectors and/or exogenous nucleic acids are well-known in the art. See, e.g., Sambrook et al. (2001) Molecular Cloning: A Laboratory Manual, Cold Spring Harbor Laboratory, New York. In some embodiments, the vector is introduced into the cell by electroporation.

Biological methods for introducing the vector into an immune effector cell include the use of DNA and RNA vectors. Viral vectors have become the most widely used method for inserting genes into mammalian, e.g., human cells.

Chemical means for introducing the vector into an immune effector cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any of the CARs described herein may be prepared by a conventional method (e.g., in vitro transcription) and then introduced into the immune effector cells via known methods such as mRNA electroporation. See, e.g., Rabinovich et al., Human Gene Therapy 17:1027-1035 (2006).

In some embodiments, the transduced or transfected immune effector cell is propagated ex vivo after introduction of the vector or isolated nucleic acid. In some embodiments, the transduced or transfected immune effector cell is cultured to propagate for at least about any of 1 day, 2 days, 3 days, 4 days, 5 days, 6 days, 7 days, 10 days, 12 days, or 14 days. In some embodiments, the transduced or transfected immune effector cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially. Other methods to confirm the presence of the nucleic acid encoding the CARs in the engineered immune effector cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

5.4.3. Sources of T Cells

In some embodiments, prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Initial activation steps in the absence of calcium may lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, in some embodiments, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations may result in increased cell yield, cell activation, and cell expansion. Further, use of high cell concentrations may allow more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. In some embodiments, using high concentration of cells allows more efficient selection of CD8+ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/ml. In some embodiments, the concentration used can be from about $1\times10^5$/ml to $1\times10^6$/ml, and any integer value in between.

In some embodiments, the cells may be incubated on a rotator for varying lengths of time at varying speeds at either 2-10° C., or at room temperature.

T cells for stimulation can also be frozen after a washing step. Without being bound by theory, the freeze and subsequent thaw step may provide a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% dextran 40 and 5% dextrose, 20% human serum albumin and 7.5% DMSO, or 31.25% plasmalyte-A, 31.25% dextrose 5%, 0.45% NaCl, 10% dextran 40 and 5% dextrose, 20% human serum albumin, and 7.5% DMSO or other suitable cell freezing media containing for example, Hespan and PlasmaLyte A. The cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815 (1991); Henderson et al., Immun 73:316-321 (1991); Bierer et al., Curr. Opin. Immun. 5:763-773 (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

5.4.4. Activation and Expansion of T Cells

In some embodiments, prior to or after genetic modification of the T cells with the CARs described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD3 antibody include UCHT1, OKT3, HIT3a (BioLegend, San Diego, US) can be used as can other methods commonly known in the art (Graves J, et al., J. Immunol. 146:2102 (1991); Li B, et al., Immunology 116:487 (2005); Rivollier A, et al., Blood 104:4029 (2004)). Examples of an anti-CD28 antibody include 9.3, B-T3, XR-CD28 (Diaclone, Besancon, France) can be used as can other methods commonly known in the art (Berg et al., Transplant Proc. 30(8):3975-3977 (1998); Haanen et al., J. Exp. Med. 190 (9):13191328 (1999); Garland et al., J. Immunol Meth. 227(1-2):53-63 (1999)).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in certain embodiments in the present disclosure.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment, the cells (for example, $10^4$ to $4\times10^8$ T cells) and beads (for example, anti-CD3/CD28 MACSiBead particles at a recommended titer of 1:100) are combined in a buffer, preferably PBS (without divalent cations such as, calcium and magnesium). Those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/mL is used. In another embodiment, greater than 100 million cells/mL is used. In a further embodiment, a concentration of cells of 10, 15, 20, 25, 30, 35, 40, 45, or 50 million cells/mL is used. In yet another embodiment, a concentration of cells from 75, 80, 85, 90, 95, or 100 million cells/mL is used. In further embodiments, concentrations of 125 or 150 million cells/mL can be used. Using high concentrations may result in increased cell yield, cell activation, and cell expansion. Further, use of high cell concentrations may allow more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment, the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

5.5. Polynucleotides

In certain embodiments, the disclosure provides polynucleotides that encode the single domain antibodies that bind to CD19 and fusion proteins comprising the single domain antibodies that bind to CD19 described herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide. In exemplary embodiments, the nucleic acid molecule provided herein comprises a sequence that encodes the single domain antibody having the sequence of SEQ ID NO: 43. Exemplary nucleic acid has SEQ ID NO: 64. In exemplary embodiments, the nucleic acid molecule provided herein comprises a sequence that encodes the single domain antibody having the sequence of SEQ ID NO: 44. Exemplary nucleic acid has SEQ ID NO: 65. In exemplary embodiments, the nucleic acid molecule provided herein comprises a sequence that encodes the single domain antibody having the sequence of SEQ ID NO: 45. In exemplary embodiments, the nucleic acid molecule provided herein comprises a sequence that encodes the single domain antibody having the sequence of SEQ ID NO: 46. In exemplary embodiments, the nucleic acid molecule provided herein comprises a sequence that encodes the single domain antibody having the sequence of SEQ ID NO: 47. In exemplary embodiments, the nucleic acid molecule provided herein comprises a sequence that encodes the single domain antibody having the sequence of SEQ ID NO: 48. In exemplary embodiments, the nucleic acid molecule provided herein comprises a sequence that encodes the single domain antibody having the sequence of SEQ ID NO: 49. In exemplary embodiments, the nucleic acid molecule provided herein comprises a sequence that encodes the single domain antibody having the sequence of SEQ ID NO: 51. Exemplary nucleic acid has SEQ ID NO: 66. In exemplary embodiments, the nucleic acid molecule provided herein comprises a sequence that encodes the single domain antibody having the sequence of SEQ ID NO: 52. Exemplary nucleic acid has SEQ ID NO: 67. In exemplary embodiments, the nucleic acid molecule provided herein comprises a sequence that encodes the single domain antibody having the sequence of SEQ ID NO: 53. In exemplary embodiments, the nucleic acid molecule provided herein comprises a sequence that encodes the single domain antibody having the sequence of SEQ ID NO: 54. In exemplary embodiments, the nucleic acid molecule provided herein comprises a sequence that encodes the single domain antibody having the sequence of SEQ ID NO: 55. In exemplary embodiments, the nucleic acid molecule provided herein comprises a sequence that encodes the single domain antibody having the sequence of SEQ ID NO: 56. In exemplary embodiments, the nucleic acid molecule provided herein comprises a sequence that encodes the single domain antibody having the sequence of SEQ ID NO: 104. Exemplary nucleic acid has SEQ ID NO: 106.

In certain embodiments, the disclosure provides polynucleotides that encode the CD19 CAR provided herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide. In exemplary embodiments, the nucleic acid molecule provided herein comprises a sequence that encodes the CAR having the sequence of SEQ ID NO: 57. Exemplary nucleic acid has SEQ ID NO: 68. In exemplary embodiments, the nucleic acid molecule provided herein comprises a sequence that encodes the CAR having the sequence of SEQ ID NO: 58. Exemplary nucleic acid has SEQ ID NO: 69. In exemplary embodiments, the nucleic acid molecule provided herein comprises a sequence that encodes the CAR having the sequence of SEQ ID NO: 59. In exemplary embodiments, the nucleic acid molecule provided herein comprises a sequence that encodes the CAR having the sequence of SEQ ID NO: 60. In exemplary embodiments, the nucleic acid molecule provided herein comprises a sequence that encodes the CAR having the sequence of SEQ ID NO: 61. In exemplary embodiments, the nucleic acid molecule provided herein comprises a sequence that encodes the CAR having the sequence of SEQ ID NO: 62. Exemplary nucleic acid has SEQ ID NO: 70. In exemplary embodiments, the nucleic acid molecule provided herein comprises a sequence that encodes the CAR having the sequence of SEQ ID NO: 63. Exemplary nucleic acid has SEQ ID NO: 71. In exemplary embodiments, the nucleic acid molecule provided herein comprises a sequence that encodes the CAR having the sequence of SEQ ID NO: 105. Exemplary nucleic acid has SEQ ID NO: 107.

The present disclosure further relates to variants of the polynucleotides described herein, wherein the variant encodes, for example, fragments, analogs, and/or derivatives of the single domain antibody or CAR that binds CD19 of the disclosure. In certain embodiments, the present disclosure provides a polynucleotide comprising a polynucleotide having a nucleotide sequence at least about 75% identical, at least about 80% identical, at least about 85% identical, at least about 90% identical, at least about 95% identical, and in some embodiments, at least about 96%, 97%, 98% or 99% identical to a polynucleotide encoding the single domain antibody or CAR that binds CD19 of the disclosure. As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

Also provided are vectors comprising the nucleic acid molecules described herein. In an embodiment, the nucleic acid molecules can be incorporated into a recombinant expression vector. The present disclosure provides recombinant expression vectors comprising any of the nucleic acids of the disclosure. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

In an embodiment, the recombinant expression vector of the disclosure can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-Cl, pMAM, and pMAMneo (Clontech). The recombinant expression vector may be a viral vector, e.g., a retroviral vector, e.g., a gamma retroviral vector.

In an embodiment, the recombinant expression vectors are prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol×resistance genes, histidinol resistance genes, tetracycline resistance genes, and ampicillin resistance genes.

The recombinant expression vector can comprise a native or normative promoter operably linked to the nucleotide sequence of the disclosure. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40 promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

In certain embodiments, a polynucleotide is isolated. In certain embodiments, a polynucleotide is substantially pure.

Also provided are host cells comprising the nucleic acid molecules described herein. The host cell may be any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5a, JM109, and KCB, SURE® Competent Cells, and SOLOPACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, Saos, PC12, SP2/0 (American Type Culture Collection (ATCC), Manassas, VA, CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATCC CRL-TIB-196). Other useful cell lines include those derived from Chinese Hamster Ovary (CHO) cells such as CHO-K1SV (Lonza Biologics, Walkersville, MD), CHO-K1 (ATCC CRL-61) or DG44.

5.6. Pharmaceutical Compositions

In one aspect, the present disclosure further provides pharmaceutical compositions comprising a single domain antibody, a binding molecule or therapeutic molecule comprising a single domain antibody, or an engineered immune effector cell of the present disclosure. In some embodiments, a pharmaceutical composition comprises a therapeutically effective amount of the single domain antibody, the binding molecule or therapeutic molecule comprising the single domain antibody, or the engineered immune effector cell of the present disclosure and a pharmaceutically acceptable excipient.

In some embodiments, provided herein is a pharmaceutical composition comprising a therapeutically effective amount of the single domain antibody provided herein and a pharmaceutically acceptable excipient.

In some embodiments, provided herein is a pharmaceutical composition comprising a therapeutically effective amount of the therapeutic molecule (such as a fusion protein, immunoconjugate, and a multispecific binding molecule) comprising the single domain antibody provided herein and a pharmaceutically acceptable excipient.

In other embodiments, provided herein is a pharmaceutical composition comprising a therapeutically effective amount of CAR comprising the single domain antibody provided herein and a pharmaceutically acceptable excipient.

In other embodiments, provided herein is a pharmaceutical composition comprising a therapeutically effective amount of engineered immune effector cells provided herein and a pharmaceutically acceptable excipient.

In other embodiments, provided herein is a pharmaceutical composition comprising a therapeutically effective amount of a nucleic acid provided herein, e.g., in a vector, and a pharmaceutically acceptable excipient, e.g., suitable for gene therapy.

In a specific embodiment, the term "excipient" can also refer to a diluent, adjuvant (e.g., Freunds' adjuvant (complete or incomplete), carrier or vehicle. Pharmaceutical excipients can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid excipients. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical excipients are described in *Remington's Pharmaceutical Sciences* (1990) Mack Publishing Co., Easton, PA. Such compositions will contain a prophylactically or therapeutically effective amount of the active ingredient provided herein, such as in purified form, together with a suitable amount of excipient so as to provide the form for proper administration to the patient. The formulation should suit the mode of administration.

In some embodiments, the choice of excipient is determined in part by the particular cell, binding molecule, and/or antibody, and/or by the method of administration. Accordingly, there are a variety of suitable formulations.

Typically, acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers may be used to control the pH in a range which optimizes the therapeutic effectiveness, especially if stability is pH dependent. Suitable buffering agents for use with the present disclosure include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives may be added to retard microbial growth. Suitable preservatives for use with the present disclosure include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Exemplary tonicity agents include polyhydric sugar alcohols, trihydric or higher sugar alcohols, such as glycerin, erythritol, arabitol, xylitol, sorbitol and mannitol.

Additional exemplary excipients include: (1) bulking agents, (2) solubility enhancers, (3) stabilizers and (4) agents preventing denaturation or adherence to the container wall. Such excipients include: polyhydric sugar alcohols (enumerated above); amino acids such as alanine, glycine, glutamine, asparagine, histidine, arginine, lysine, omithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be present to help solubilize the therapeutic agent as well as to protect the therapeutic protein against agitation-induced aggregation, which also permits the formulation to be exposed to shear surface stress without causing denaturation of the active therapeutic protein or antibody. Suitable non-ionic surfactants include, e.g., polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they are preferably sterile. The pharmaceutical composition may be rendered sterile by filtration through sterile filtration membranes. The pharmaceutical compositions herein generally can be placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

In another embodiment, a pharmaceutical composition can be provided as a controlled release or sustained release system. In one embodiment, a pump may be used to achieve controlled or sustained release (see. e.g., Sefton, Crit. Ref. Biomed. Eng. 14:201-40 (1987); Buchwald et al., Surgery 88:507-16 (1980); and Saudek et al., N. Engl. J. Med. 321:569-74 (1989)). In another embodiment, polymeric materials can be used to achieve controlled or sustained release of a prophylactic or therapeutic agent (e.g., a fusion protein as described herein) or a composition provided herein (see, e.g., *Medical Applications of Controlled Release* (Langer and Wise eds., 1974); *Controlled Drug Bioavailability. Drug Product Design and Performance* (Smolen and Ball eds., 1984); Ranger and Peppas, J. Macromol. Sci. Rev. Macromol. Chem. 23:61-126 (1983); Levy et al., Science 228:190-92 (1985); During et al., Ann. Neurol. 25:351-56 (1989); Howard et al., *J. Neurosurg.* 71:105-12 (1989); U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. In yet another embodiment, a controlled or sustained release system can be placed in proximity of a particular target tissue, for example, the nasal passages or lungs, thus requiring only a fraction of the systemic dose (see. e.g., Goodson, *Medical Applications of Controlled Release* Vol. 2, 115-38 (1984)). Controlled release systems are discussed, for example, by Langer, Science 249:1527-33 (1990). Any technique known to one of skill in the art can be used to produce sustained release formulations comprising one or more agents as described herein (see, e.g., U.S. Pat. No. 4,526,938, PCT publication Nos. WO 91/05548 and WO 96/20698, Ning et al., Radiotherapy & Oncology 39:179-89 (1996); Song et al., PDA J. of Pharma. Sci. & Tech. 50:372-97 (1995); Cleek et al., Pro. Int'l. Symp. Control. Rel. Bioact. Mater. 24:853-54 (1997); and Lam et al., Proc. Int'l. Symp. Control Rel. Bioact. Mater. 24:759-60 (1997)).

The pharmaceutical compositions described herein may also contain more than one active compound or agent as necessary for the particular indication being treated. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

Various compositions and delivery systems are known and can be used with the therapeutic agents provided herein, including, but not limited to, encapsulation in liposomes, microparticles, microcapsules, recombinant cells capable of expressing the single domain antibody or therapeutic molecule provided herein, construction of a nucleic acid as part of a retroviral or other vector, etc.

In some embodiments, the pharmaceutical composition provided herein contains the binding molecules and/or cells in amounts effective to treat or prevent the disease or disorder, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined.

5.7. Methods and Uses

In another aspect, provided herein are methods for using and uses of the CD19 binding molecules provided herein, including the anti-CD19 VHH, chimeric antigen receptors (CARs), and/or engineered cells expressing the recombinant receptors.

5.7.1. Therapeutic Methods and Uses

Such methods and uses include therapeutic methods and uses, for example, involving administration of the molecules, cells, or compositions containing the same, to a subject having a disease, condition, or disorder expressing or associated with CD19 expression, and/or in which cells or tissues express CD19. In some embodiments, the molecule, cell, and/or composition is administered in an effective amount to effect treatment of the disease or disorder. Uses include uses of the antibodies and cells in such methods and treatments, and in the preparation of a medicament in order to carry out such therapeutic methods. In some embodiments, the methods are carried out by administering the antibodies or cells, or compositions comprising the same, to the subject having or suspected of having the disease or condition. In some embodiments, the methods thereby treat the disease or disorder in the subject.

In some embodiments, the treatment provided herein cause complete or partial amelioration or reduction of a disease or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms include, but do not imply, complete curing of a disease or complete elimination of any symptom or effect(s) on all symptoms or outcomes.

As used herein, in some embodiments, the treatment provided herein delay development of a disease or disorder, e.g., defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease or disorder. For example, a late stage cancer, such as development of metastasis, may be delayed.

In other embodiments, the method or the use provided herein prevents a disease or disorder. In some embodiments, the disease or disorder is a CD19 associated disease or disorder. In some embodiments, the disease or disorder is a B cell associated disease or disorder. In some embodiments, the disease or disorder is a B cell malignancy. In some embodiments, the B cell malignancy is a B cell leukemia or B cell lymphoma. In a specific embodiment, the disease or disorder is marginal zone lymphoma (e.g., splenic marginal zone lymphoma). In a specific embodiment, the disease or disorder is diffuse large B cell lymphoma (DLBCL). In another specific embodiment, the disease or disorder is mantle cell lymphoma (MCL). In another specific embodiment, the disease or disorder is primary central nervous system (CNS) lymphoma. In another specific embodiment, the disease or disorder is primary mediastinal B cell lymphoma (PMBL). In another specific embodiment, the disease or disorder is small lymphocytic lymphoma (SLL). In another specific embodiment, the disease or disorder is B cell prolymphocytic leukemia (B-PLL). In another specific embodiment, the disease or disorder is follicular lymphoma (FL). In another specific embodiment, the disease or disorder is burkitt lymphoma. In another specific embodiment, the disease or disorder is primary intraocular lymphoma. In another specific embodiment, the disease or disorder is chronic lymphocytic leukemia (CLL). In another specific embodiment, the disease or disorder is acute lymphoblastic leukemia (ALL). In another specific embodiment, the disease or disorder is hairy cell leukemia (HCL). In another specific embodiment, the disease or disorder is precursor B lymphoblastic leukemia. In another specific embodiment, the disease or disorder is non-hodgkin lymphoma (NHL). In another specific embodiment, the disease or disorder is high-grade B-cell lymphoma (HGBL). In another specific embodiment, the disease or disorder is multiple myelomia (MM). In other embodiments, the disease or disorder is a relapsed or refractory B cell malignancy, such as relapsed or refractory ALL (R/R ALL).

In other embodiments, the disease or disorder is an autoimmune and inflammatory disease, including, e.g., those associated with inappropriate or enhanced B cell numbers and/or activation.

In some embodiments, the methods include adoptive cell therapy, whereby genetically engineered cells expressing the provided CD19-targeted CARs are administered to a subject. Such administration can promote activation of the cells (e.g., T cell activation) in a CD19-targeted manner, such that the cells of the disease or disorder are targeted for destruction.

In some embodiments, the methods include administration of the cells or a composition containing the cells to a subject, tissue, or cell, such as one having, at risk for, or suspected of having the disease or disorder. In some embodiments, the cells, populations, and compositions are administered to a subject having the particular disease or disorder to be treated, e.g., via adoptive cell therapy, such as adoptive T cell therapy. In some embodiments, the cells or compositions are administered to the subject, such as a subject having or at risk for the disease or disorder. In some embodiments, the methods thereby treat, e.g., ameliorate one or more symptom of the disease or disorder, such as by lessening tumor burden in a CD19-expressing cancer.

Methods for administration of cells for adoptive cell therapy are known, as described, e.g., in US Patent Application Publication No. 2003/0170238; U.S. Pat. No. 4,690,915; Rosenberg, *Nat Rev Clin Oncol.* 8 (10):577-85 (2011); Themeli et al., Nat Biotechnol. 31(10): 928-933 (2013); Tsukahara et al., Biochem Biophys Res Commun 438(1): 84-9 (2013); and Davila et al., PLoS ONE 8(4): e61338 (2013). These methods may be used in connection with the methods and compositions provided herein.

In some embodiments, the cell therapy (e.g., adoptive T cell therapy) is carried out by autologous transfer, in which the cells are isolated and/or otherwise prepared from the subject who is to receive the cell therapy, or from a sample derived from such a subject. Thus, in some aspects, the cells are derived from a subject in need of a treatment and the cells, following isolation and processing are administered to the same subject. In other embodiments, the cell therapy (e.g., adoptive T cell therapy) is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. The subject can be male or female and can be any suitable age, including infant, juvenile, adolescent, adult, and geriatric subjects. In some examples, the subject is a validated animal model for disease, adoptive cell therapy, and/or for assessing toxic outcomes.

The CD19-binding molecules, such as VHHs and chimeric receptors containing the VHHs and cells expressing the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

The amount of a prophylactic or therapeutic agent provided herein that will be effective in the prevention and/or treatment of a disease or condition can be determined by standard clinical techniques. Effective doses may be extrapolated from dose-response curves derived from in vitro or animal model test systems. For the prevention or treatment of disease, the appropriate dosage of the binding molecule or cell may depend on the type of disease or disorder to be treated, the type of binding molecule, the severity and course of the disease or disorder, whether the therapeutic agent is administered for preventive or therapeutic purposes, previous therapy, the patient's clinical history and response to the agent, and the discretion of the attending physician. The compositions, molecules and cells are in some embodiments suitably administered to the patient at one time or over a series of treatments.

For example, depending on the type and severity of the disease, dosages of antibodies may include about 10 ug/kg to 100 mg/kg or more. Multiple doses may be administered intermittently. An initial higher loading dose, followed by one or more lower doses may be administered. In some embodiments, wherein the pharmaceutical composition comprises any one of the single domain antibodies described herein, the pharmaceutical composition is administered at a dosage of about 10 ng/kg up to about 100 mg/kg of body weight of the individual or more per day, for example, at about 1 mg/kg/day to 10 mg/kg/day, depending upon the route of administration. Guidance as to particular dosages and methods of delivery is provided in the literature (see, e.g., U.S. Pat. Nos. 4,657,760; 5,206,344; and 5,225,212).

In the context of genetically engineered cells containing the binding molecules, in some embodiments, a subject may be administered the range of about one million to about 100 billion cells and/or that amount of cells per kilogram of body weight. In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. Dosages may vary depending on attributes particular to the disease or disorder and/or patient and/or other treatments.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once or multiple times during a dosing cycle. A dosing cycle can be, e.g., 1, 2, 3, 4, 5 or more week(s), or 1, 2, 3, 4, 5, or more month(s). The optimal dosage and treatment regime for a particular patient can be determined by one skilled in the art of medicine by monitoring the patient for signs of disease and adjusting the treatment accordingly.

In some embodiments, the cells or antibodies are administered as part of a combination treatment, such as simultaneously with or sequentially with, in any order, another therapeutic intervention, such as another antibody or engineered cell or receptor or agent, such as a cytotoxic or therapeutic agent.

In some embodiments, the cells or antibodies are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

In certain embodiments, once the cells are administered to a mammal (e.g., a human), the biological activity of the engineered cell populations and/or antibodies is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as CD107a, IFNγ, IL-2, and TNF. In some aspects the biological activity is measured by assessing clinical outcome, such as reduction in tumor burden or load.

In some specific embodiments, provided herein is a method for treating a disease or disorder in a subject comprising administering to the subject a binding molecule comprising a single domain antibody that binds to CD19 as described in Section 5.2 above, including, e.g., those with CDRs in Table 2, those comprising the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, or SEQ ID NO: 104 and those comprising an amino acid sequence having at least 75%, 80%, 85%, 90%, 91%, 92%, 93%, 94%, 95%, 96%, 97%, 98%, or 99% sequence identify to SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, or SEQ ID NO: 104. In some embodiments, the disease or disorder is a CD19 associated disease or disorder. In some embodiments, the disease or disorder is a B cell associated disease or disorder. In some embodiments, the disease or disorder is a B cell malignancy. In some embodiments, the B cell malignancy is a B cell leukemia or B cell lymphoma. In a specific embodiment, the disease or disorder is marginal zone lymphoma (e.g., splenic marginal zone lymphoma). In a specific embodiment, the disease or disorder is diffuse large B cell lymphoma (DLBCL). In another specific embodiment, the disease or disorder is mantle cell lymphoma (MCL). In another specific embodiment, the disease or disorder is primary central nervous system (CNS) lymphoma. In another specific embodiment, the disease or disorder is primary mediastinal B cell lymphoma (PMBL). In another specific embodiment, the disease or disorder is small lymphocytic lymphoma (SLL). In another specific embodiment, the disease or disorder is B cell prolymphocytic leukemia (B-PLL). In another specific embodiment, the disease or disorder is follicular lymphoma (FL). In another specific embodiment, the disease or disorder is burkitt lymphoma. In another specific embodiment, the disease or disorder is primary intraocular lymphoma. In another specific embodiment, the disease or disorder is chronic lymphocytic leukemia (CLL). In another specific embodiment, the disease or disorder is acute lymphoblastic leukemia (ALL). In another specific embodiment, the disease or disorder is hairy cell leukemia (HCL). In another specific embodiment, the disease or disorder is precursor B lymphoblastic leukemia. In another specific embodiment, the disease or disorder is non-hodgkin lymphoma (NHL). In another specific embodiment, the disease or disorder is high-grade B-cell lymphoma (HGBL). In another specific embodiment, the disease or disorder is multiple myelomia (MM). In other embodiments, the disease or disorder is a relapsed or refractory B cell malignancy, such as relapsed or refractory ALL (R/R ALL). In other embodiments, the disease or disorder is an autoimmune and inflammatory disease, including, e.g., those associated with inappropriate or enhanced B cell numbers and/or activation.

In other embodiments, provided herein is a method for treating a disease or disorder comprising administering to the subject an engineered immune effector cell (such as T cell) as provided in Section 5.4, including, e.g., the cells comprising a CAR provided in Section 5.3. In some embodiments, the engineered immune cell administered to the subject comprises a CAR comprising a polypeptide comprising: (a) an extracellular antigen binding domain comprising an anti-CD19 sdAb; (b) a transmembrane domain; and (c) an intracellular signaling domain, wherein the anti-CD19 sdAb is as described in Section 5.2 above, including e.g., those with CDRs in Table 2, those comprising the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, or SEQ ID NO: 104, and those comprising an amino acid sequence having at least 75%, 80%, 85%, 90%, 91%, 92%, 93%, 94%, 95%, 96%, 97%, 98%, or 99% sequence identify to SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, or SEQ ID NO: 104. In some embodiments, the engineered immune cell administered to the subject comprises a CAR comprising an amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, and SEQ ID NO: 105, or comprising a polypeptide having at least 75%, 80%, 85%, 86%, 87%, 88%, 89%, 90%, 91%, 92%, 93%, 94%, 95%, 96%, 97%, 98%, or 99% sequence identity to an amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, and SEQ ID NO: 105. In some embodiments, the disease or disorder is a CD19 associated disease or disorder. In some embodiments, the disease or disorder is a B cell associated disease or disorder. In some embodiments, the disease or disorder is a B cell malignancy. In some embodiments, the B cell malignancy is a B cell leukemia or B cell lymphoma. In a specific embodiment, the disease or disorder is marginal zone lymphoma (e.g., splenic marginal zone lymphoma). In a specific embodiment, the disease or disorder is diffuse large B cell lymphoma (DLBCL). In another specific embodiment, the disease or disorder is mantle cell lymphoma (MCL). In another specific embodiment, the disease or disorder is primary central nervous system (CNS) lymphoma. In another specific embodiment, the disease or disorder is primary mediastinal B cell lymphoma (PMBL). In another specific embodiment, the disease or disorder is small lymphocytic lymphoma (SLL). In another specific embodiment, the disease or disorder is B cell prolymphocytic leukemia (B-PLL). In another specific embodiment, the disease or disorder is follicular lymphoma (FL). In another specific embodiment, the disease or disorder is burkitt lymphoma. In another specific embodiment, the disease or disorder is primary intraocular lymphoma. In another specific embodiment, the disease or disorder is chronic lymphocytic leukemia (CLL). In another specific embodiment, the disease or disorder is acute lymphoblastic leukemia (ALL). In another specific embodiment, the disease or disorder is hairy cell leukemia (HCL). In another specific embodiment, the disease or disorder is precursor B lymphoblastic leukemia. In another specific embodiment, the disease or disorder is non-hodgkin lymphoma (NHL). In another specific embodiment, the disease or disorder is high-grade B-cell lymphoma (HGBL). In another specific embodiment, the disease or disorder is multiple myelomia (MM). In other embodiments, the disease or disorder is a relapsed or refractory B cell malignancy, such as relapsed or refractory ALL (R/R ALL). In other embodiments, the disease or disorder is an autoimmune and inflammatory disease, including, e.g., those associated with inappropriate or enhanced B cell numbers and/or activation.

5.7.2. Diagnostic and Detection Methods and Uses

In another aspect, provided herein are methods involving use of the binding molecules provided herein, e.g., VHHs that binds CD19 and molecules (such as conjugates and complexes) containing such VHHs, for detection, prognosis, diagnosis, staging, determining binding of a particular treatment to one or more tissues or cell types, and/or informing treatment decisions in a subject, such as by the detection of CD19 and/or the presence of an epitope thereof recognized by the antibody.

In some embodiments, an anti-CD19 antibody (such as any one of the anti-CD19 single domain antibodies described herein) for use in a method of diagnosis or detection is provided. In a further aspect, a method of detecting the presence of CD19 in a biological sample is provided. In certain embodiments, the method comprises detecting the presence of CD19 protein in a biological sample. In certain embodiments, CD19 is human CD19. In some embodiments, the methods are diagnostic and/or prognostic methods in association with a CD19-expressing disease or disorder. The methods in some embodiments include incubating and/or probing a biological sample with the antibody and/or administering the antibody to a subject. In certain embodiments, a biological sample includes a cell or tissue or portion thereof, such as tumor or cancer tissue or biopsy or section thereof. In certain embodiments, the contacting is under conditions permissive for binding of the anti-CD19 antibody to CD19 present in the sample. In some embodiments, the methods further include detecting whether a complex is formed between the anti-CD19 antibody and CD19 in the sample, such as detecting the presence or absence or level of such binding. Such a method may be an in vitro or in vivo method. In one embodiment, an anti-CD19 antibody is used to select subjects eligible for therapy with an anti-CD19 antibody or engineered antigen receptor, e.g., where CD19 is a biomarker for selection of patients.

In some embodiments, a sample, such as a cell, tissue sample, lysate, composition, or other sample derived therefrom is contacted with the anti-CD19 antibody and binding or formation of a complex between the antibody and the sample (e.g., CD19 in the sample) is determined or detected. When binding in the test sample is demonstrated or detected as compared to a reference cell of the same tissue type, it may indicate the presence of an associated disease or disorder, and/or that a therapeutic containing the antibody will specifically bind to a tissue or cell that is the same as or is of the same type as the tissue or cell or other biological material from which the sample is derived. In some embodiments, the sample is from human tissues and may be from diseased and/or normal tissue, e.g., from a subject having the disease or disorder to be treated and/or from a subject of the same species as such subject but that does not have the disease or disorder to be treated. In some cases, the normal tissue or cell is from a subject having the disease or disorder to be treated but is not itself a diseased cell or tissue, such as a normal tissue from the same or a different organ than a cancer that is present in a given subject.

Various methods known in the art for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be used so as to meet the needs of various uses of the method which are often dictated by the availability of assay equipment and compatible immunoassay procedures. Exemplary labels include radionuclides (e.g. $^{125}I$, $^{131}I$, $^{35}S$, $^{3}H$, or $^{32}P$ and/or chromium ($^{31}Cr$), cobalt ($^{57}Co$), fluorine ($^{18}F$), gadolinium ($^{153}Gd$, $^{159}Gd$), germanium ($^{68}Ge$), holmium ($^{166}Ho$), indium ($^{115}In$, $^{113}In$, $^{112}In$, $^{111}In$), iodine ($^{125}I$, $^{123}I$, $^{121}I$), lanthanium ($^{140}La$), lutetium ($^{177}Lu$), manganese ($^{54}Mn$), molybdenum ($^{99}Mo$), palladium ($^{103}Pd$), phosphorous ($^{32}P$), praseodymium ($^{142}Pr$), promethium ($^{149}Pm$), rhenium (186Re, 188Re), rhodium (105Rh), rutheroium (97Ru), samarium ($^{153}Sm$), scandium ($^{47}Sc$), selenium ($^{75}Se$), ($^{85}Sr$), sulphur ($^{35}S$), technetium ($^{99}Tc$), thallium ($^{201}Ti$) tin ($^{113}Sn$, $^{117}Sn$), tritium (3H), xenon ($^{133}Xe$), ytterbium ($^{169}Yb$, $^{175}Yb$), yttrium ($^{90}Y$),), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Various general techniques to be used in performing the various immunoassays noted above are known.

In certain embodiments, labeled antibodies (such as anti-CD19 single domain antibodies) are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. In other embodiments, antibodies are not labeled, and the presence thereof can be detected using a labeled antibody which binds to any of the antibodies.

5.8. Kits and Articles of Manufacture

Further provided are kits, unit dosages, and articles of manufacture comprising any of the single domain antibodies, the chimeric antigen receptors, or the engineered immune effector cells described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

For the sake of conciseness, certain abbreviations are used herein. One example is the single letter abbreviation to represent amino acid residues. The amino acids and their corresponding three letter and single letter abbreviations are as follows:

| Amino acid | Three letter | One letter |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |

-continued

| Amino acid | Three letter | One letter |
|---|---|---|
| tyrosine | Tyr | (Y) |
| valine | Val | (V) |

The disclosure is generally disclosed herein using affirmative language to describe the numerous embodiments. The disclosure also specifically includes embodiments in which particular subject matter is excluded, in full or in part, such as substances or materials, method steps and conditions, protocols, procedures, assays or analysis. Thus, even though the disclosure is generally not expressed herein in terms of what the disclosure does not include, aspects that are not expressly included in the disclosure are nevertheless disclosed herein.

A number of embodiments of the disclosure have been described. Nevertheless, it will be understood that various modifications may be made without departing from the spirit and scope of the disclosure. Accordingly, the following examples are intended to illustrate but not limit the scope of disclosure described in the claims.

6. EXAMPLES

The following is a description of various methods and materials used in the studies, and are put forth so as to provide those of ordinary skill in the art with a complete disclosure and description of how to make and use the present disclosure, and are not intended to limit the scope of what the inventors regard as their disclosure nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present disclosure. Efforts have been made to ensure accuracy with respect to numbers used (e.g., amounts, percentages, etc.), but some experimental errors and deviations should be accounted for.

6.1. Example 1—Preparation of Anti-CD19 VHH

To develop VHH with high binding affinity to CD19 antigen, camels were immunized with human CD19 protein. A phage-display library was then constructed to screen VHH leads. Unique clones were picked based on specific binding and were ranked according to the VHH complementarity determining region (CDR), especially CDR3 which enlarges antigen recognition repertoire and binding.

6.1.1. Cell Line Construction

K562.huCD19.Luc cell line was developed in house following the method as briefly described below. Human CD19 coding sequence (NM_001770.5) was synthesized and subcloned to pLVX-puro (Clontech, Cat. No. 632164) between EcoRI and BamHI restriction sites to obtain the plasmid pLVX-huCD19.Luc.Puro. Lentivirus was packaged by transient transfection of Lenti-X 293T host cells with a mixture of plasmids containing psPAX2, pMD.2G and pLVX-huCD19.Luc.Puro. $0.5\times10^6$ of K562 cells (ATCC #CRL-243) were transduced by infecting with 100 μL of LV-huCD19.Luc.PuroR lentivirus. The transduced K562.huCD19.Luc cells were selected and generated with puromycin selection medium (RPMI1640 supplemented with 10% FBS and 5 μg/mL puromycin) every 2-3 days. After 3 rounds of selections, the cell pools were harvested by centrifugation. The harvested cells were aliquoted and cryopreserved and ready for further use.

The expression of human CD19 in the K562.huCD19.Luc cell line was validated by flow cytometry using PE conjugated anti-human CD19 antibody (Miltenyi Biotec, Cat. No. 130-105-086). Briefly, $2\times10^5$ of K562.huCD19.Luc cells or K562 cells were incubated with PE conjugated anti-human CD19 antibody at 4° C. for 30 mins, followed by three time washes, and were re-suspended in 200 μL of DPBS with 0.5% FBS for FACS analysis on Attune NXT flow cytometry (Thermo Fisher) to detect the expression level of human CD19 antigen. The mean fluorescence intensity (MFI) of K562.huCD19.Luc was 243.06 folds higher than that of K562 cells (negative control).

6.1.2. Animal Immunization and Immune Response Testing

One adult male camel (*Camelus bactrian*) was immunized subcutaneously with human CD19 protein (ACRO, Cat. No. CD9-H52H2) for five times with two week intervals. Blood was collected on pre-immune day (Pre) and last immunization day (TB). Immune response of the camel was assessed by ELISA, in which the binding between serum samples and immobilized antigen was tested. A robust immune response was induced upon CD19 antigen injection to the animal and the serum titer reached >1:243 k. This data suggested that the antibody titer increased significantly with CD19 antigen immunization.

Three to five days after the last immunization, 100 mL of blood was collected from the jugular vein as production bleed. Peripheral blood lymphocytes (PBLs) were isolated from the blood according to the procedure of lymphoprep.

6.1.3. Antibody Phage Library Construction

Total RNAs were extracted from the isolated lymphocytes using TRIZOL® Reagent (Thermofisher, Cat. No. 15596026) according to the manufacturer's instruction, and were reverse transcribed into cDNAs with an oligo$(dT)_{20}$ primer using PrimeScript™ 1st Strand cDNA Synthesis Kit (Takara, Cat. No. 6110A) according to the manufacturer's protocol. Forward and reverse specific degenerate primers (see Chinese patent CN105555310B) were designed to amplify the VHH fragments, in which two Sf1I restriction sites were introduced. The VHH fragments were amplified by using a two-step polymerase chain reaction (PCR) and the second PCR products were digested with Sf1I and gel purified, and then inserted into phagemid vector—pFL249, which were electro-transferred into *E. coli* cells to generate the phage display VHH immune library.

A small portion of the transformed cells were diluted and streaked on 2×YT plates supplemented with 100 μg/mL ampicillin. The colonies were counted to calculate the library size. Positive clones were randomly picked and sequenced to assess the quality of the library. The rest of the transformed cells were streaked onto 245-mm square 2×YT-agar dishes supplemented with 100 μg/mL ampicillin and 2% glucose. Lawns of colonies were scraped off the dishes. A small aliquot of the cells were used for library plasmids isolation. Then the rest cells were supplemented with glycerol and stored at −80° C. as stock.

6.1.4. Phage-Display Panning

After infection with helper phage, recombinant phage particles which display VHH domains on the surface as gene III fusion proteins were produced. Phage particles were prepared according to standard methods and stored after filter sterilization at 4° C. for further research. Phage libraries were used for different panning strategies. In the first and second rounds of panning, biotinylated human CD19 antigen (biotin labeled with Sulfo-NHS-LC-Biotin Kit) was incubated with the phage libraries and subsequently captured on Streptavidin Dynabeads (Invitogen). Followed by extensive washing, bound phages were eluted with triethylamine. After two rounds of panning, phage enrichment was observed.

6.1.5. ELISA Screening

Individual library clones were inoculated and induced for expression in 96-deep-well plates. ELISA screening was performed to screen VHH clones which recognize human CD19 antigen specifically.

To identify VHH clones that bind to antigen specific cells—K562.huCD19.Luc cells, K562.huCD19.Luc cells and K562.Luc cells (negative control) were blocked with 3% BSA buffer at room temperature for 1 hour. Single clone was randomly picked from the output library and cultured in a 96-deep-well plate. When the OD600 of bacteria culture reached to 0.6-0.8, IPTG was added to induce the expression overnight. The bacteria were collected by centrifugation, and then seeded in a microwell plate.

Exemplary anti-CD19 VHH domains of the disclosure (i.e., VHH-083, VHH-111, VHH-131, 77LICA542, 77LICA519, 77LICA602, LIC1157 and LIC1159) were selected and sequenced. The CDR (e.g., as defined by Kabat or IMGT numbering scheme) and VHH sequences are summarized in Table 2 and the Sequence Listing provided herein.

6.2. Example 2—Constructions and Immune Cells Expression of VHH Chimeric Receptor Polypeptides 6.2.1. Construction of CD19 VHH CARs A nucleic acid sequence encoding a CAR backbone polypeptide comprising from the N-terminus to the C-terminus: a CD8α hinge domain, a CD8α transmembrane domain, a CD137 cytoplasmic domain and a CD3ζ cytoplasmic domain was chemically synthesized and cloned into a pre-modified lentiviral vector downstream and operably linked to a hEF1α promoter. Multi-cloning sites (MCS) in the vector allowed insertion of a nucleic acid sequence comprising a Kozak sequence (GCCGCCACC (SEQ ID NO: 78)) operably linked to a nucleic acid sequence encoding a CD8α signal peptide fused to the N-terminus of VHH fragment(s), and the upstream was operably linked to the CAR backbone sequence.

To construct a monovalent VHH-based CAR using the CAR backbone vector, a nucleic acid sequence encoding the anti-CD19 VHH domain was operably linked to the 3' of the nucleic acid sequence encoding the Kozak-CD8α signal peptide. The fusion nucleic acid sequence was chemically synthesized and cloned into the CAR backbone via the EcoRI (5'-GAATTC-3' (SEQ ID NO: 97)) and SpeI (5'-ACTAGT-3' (SEQ ID NO: 98)) restriction sites by molecular cloning techniques known in the art.

Exemplary CD19 VHH CAR constructs are listed in Table 5. Anti-CD19 scFv (FMC63 scFv) (SEQ ID NO: 99) construct was also cloned into the CAR backbone to serve as a positive control and is listed in Table 5 too.

TABLE 5

Exemplary CD19 CAR Constructs

| Exemplary CAR Code | Amino Acid Sequence | Signal Peptide | Extra-cellular antigen binding domain | Hinge & TM | Co-stimulatory signaling domain | Primary intra-cellular signaling domain |
|---|---|---|---|---|---|---|
| VHH-083 CAR | SEQ ID NO: 57 | CD8α | VHH-083 | CD8α | CD137 | CD3ζ |
| VHH-111 CAR | SEQ ID NO: 58 | CD8α | VHH-111 | CD8α | CD137 | CD3ζ |
| VHH-131 CAR | SEQ ID NO: 105 | CD8α | VHH-131 | CD8α | CD137 | CD3ζ |
| CD19 scFv CAR | SEQ ID NO: 100 | CD8α | FMC63 scFv | CD8α | CD137 | CD3ζ |

The nucleic acid sequences of VHH-083 CAR, VHH-111 CAR and VHH-131 CAR are SEQ ID NO: 68, SEQ ID NO: 69 and SEQ ID NO: 107, respectively, as shown in the Sequence Listing. In these exemplary CAR constructs, the signal peptide derived from CD8α has an amino acid sequence of SEQ ID NO: 72; the hinge derived from CD8α has an amino acid sequence of SEQ ID NO: 73; the transmembrane domain derived from CD8α has an amino acid sequence of SEQ ID NO: 74; the co-stimulatory signaling domain derived from CD137 has an amino acid sequence of SEQ ID NO: 75; and the primary intracellular signaling domain derived from CD3 (has an amino acid sequence of SEQ ID NO: 76.

6.2.2. Packaging of Lentivirus Vector

The lentivirus packaging plasmids mixture containing pMDLg.pRRE (Addgene, #12251), pRSV-REV (Addgene, #12253) and pMD2.G (Addgene, #12259) was pre-mixed with the vectors expressing CAR constructs at a pre-optimized ratio with polyetherimide (PEI). The transfection mixture was then added dropwise to the HEK293T cells and mixed gently, followed by medium replacement post 6-8 hours. The virus-containing supernatants were collected at 48 hours and 72 hours, and then centrifuged at 3000 g for 10 mins at 4° C. Post lentivirus concentration, the supernatants were carefully discarded and the virus pellets were re-suspended with D10 medium (DMEM, 10% FBS, 1 mM Sodium Pyruvate and 2 mM L-Glutamine). The harvested virus was aliquoted and stored at −80° C. immediately. The virus titer was assessed and determined by CHO mammalian cells transduction efficiency. The LV titers of CD19 CAR reached within a range of $1\times10^8$-$2\times10^8$.

6.2.3. T cell Isolation and Activation

Human PBMCs were collected from healthy donors. Human T cells were purified from PBMCs using Miltenyi Pan T cell isolation kit (Cat. #130-096-535), according to manufacturer protocol as described below. The cell number was counted and the cell suspension was centrifuged at 300 g for 10 mins at 4° C. The supernatant was then aspirated off and the cell pellets were re-suspended in 40 μL of the buffer per $10^7$ total cells. 10 μL of Pan T Cell Biotin-Antibody Cocktail was added per $10^7$ total cells, mixed thoroughly and incubated for 5 mins at 4° C. 30 μL of the buffer was then added per $10^7$ total cells. 20 μL of Pan T Cell MicroBead Cocktail was added per $10^7$ cells. The cell suspension mixture was mixed thoroughly and incubated for an additional 10 mins at 4° C. A minimum volume (vol.) of 500 μL was required for magnetic separation. In magnetic separation, an LS column was placed in the magnetic field of a suitable MACS Separator. The LS column was rinsed with 3 mL of buffer. The cell suspension was then applied onto the column and flow-through was collected containing the unlabeled cells, which represented the enriched T cell fractions. Additional T cells were collected by washing the column with 3 mL of buffer and collecting unlabeled cells that passed through. These unlabeled cells again represented the enriched T cells and were combined with the flow-through from the previous step. The pooled enriched T cells were then centrifuged and re-suspended with T cell culture medium (RPMI1640, 10% heat-inactivated fetal bovine serum (FBS) and 300 IU/mL of IL-2). The freshly isolated T cells were activated by the addition of anti-CD3/CD28 MACSiBead particles (Miltenyi, Cat. #130-111-160) in T cell culture medium according to the manufacturer protocol.

6.2.4. Generation of CD19 VHH CAR-T Cells

Based on the preliminary results of CD19 CAR-T cells generated by RNA electroporation and screened by in vitro assays, CD19 CAR-T cells were selected, designed and generated by lentivirus transduction for the efficacy analysis in human primary T cells. Additionally, CD19 scFv CAR-T cells were assessed as the positive control. Activated T cells were cultured at $0.5\times10^6$ cells in 0.5 mL medium per well of a 24-well plate. After 24 hours, when T cells were blasting, 0.5 mL of non-concentrated, or smaller volumes of concentrated viral supernatant was added; and T cells were transduced at a multiplicity of infection (MOI) of 15 by centrifugation at 1200 g for 1.5 hours at 32° C. The transduced cells were then transferred to the cell culture incubator for transgene expression under suitable conditions. T cells began to divide in a logarithmic growth pattern, which was monitored by measuring the cell number (viable cells/per mL) and viability (%). The T cells culture was replenished with fresh medium every two days. As the T cells began to rest down after approximately 7-9 days, they were ready to be harvested and cryopreserved for later analysis.

Before cryopreserving, the percentages of cells transduced (expressing VHH domain or scFv domain on T cell surface) were determined by flow cytometric analysis. The T cells were stained with LIVE/DEAD™ Fixable Dead Cell Stain Kits (Invitrogen, Cat. #L34976), VHH-based CAR-T cells were stained with Goat anti-Llama IgG FITC Conjugate (Bethyl, Cat. #A160-100F), and scFv-based CAR-T cells were stained with FITC-labeled Recombinant Protein L (Acro, Cat. #RPL-PF141) at 4° C., for 30 mins, followed by three-time washes and were re-suspended in 200 μL of DPBS with 0.5% FBS for FACS analysis on a NovoCyte Flow Cytometer (ACEA Biosciences). The FACS data was analyzed by Novoexpress software.

Figure 1B:
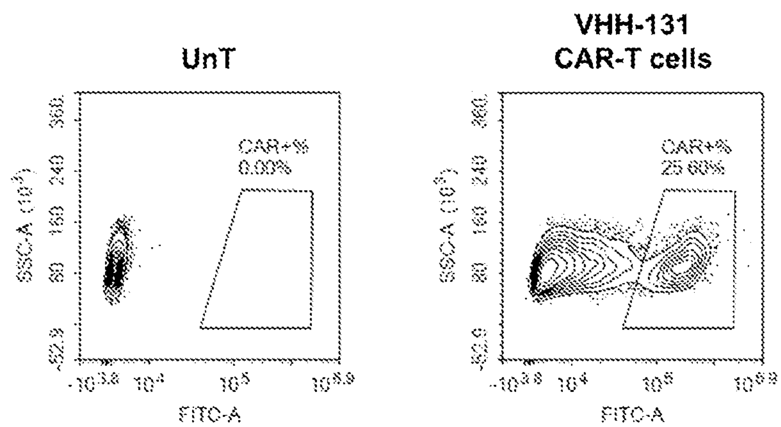
Figure 1C:
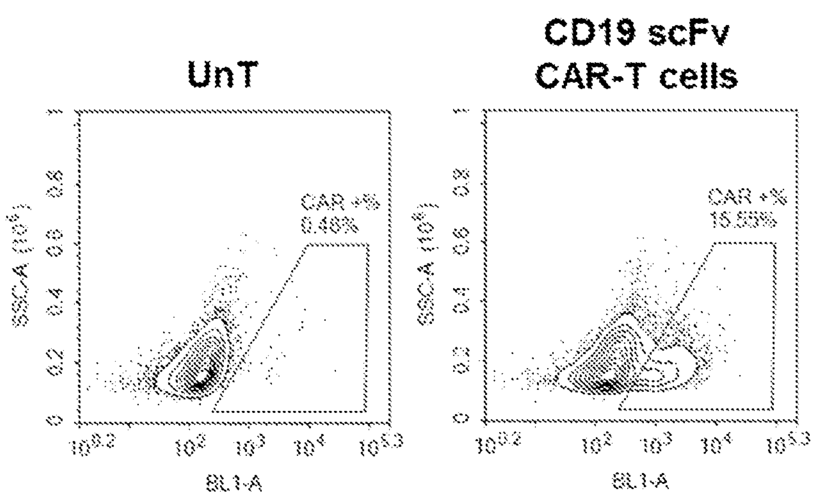
Figure 2A:
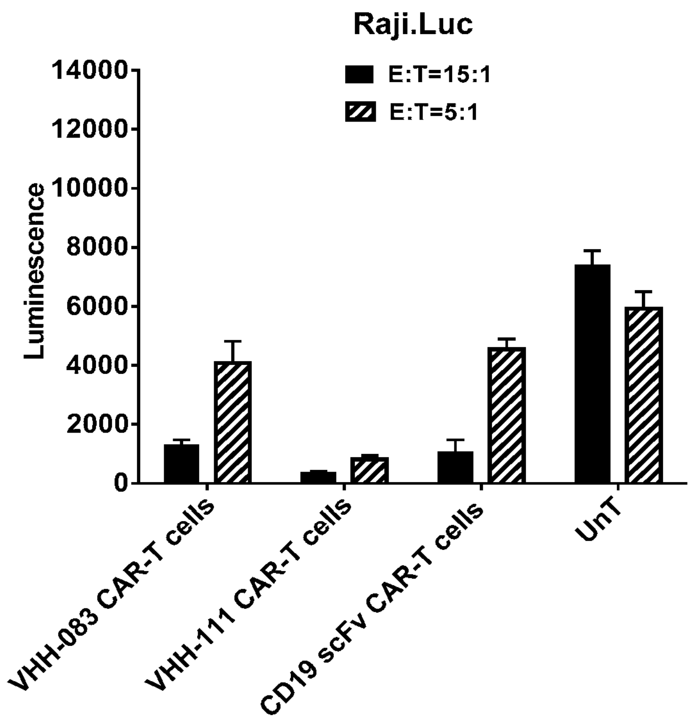
FIGS. 2A-2G show in vitro cytotoxicity of exemplary VHH-based CAR-T cells compared to that of scFv-based CAR-T cells against CD19 positive cell lines (FIGS. 2A-2D) or CD19 negative cell lines (FIGS. 2E-2G).
Figure 2B:
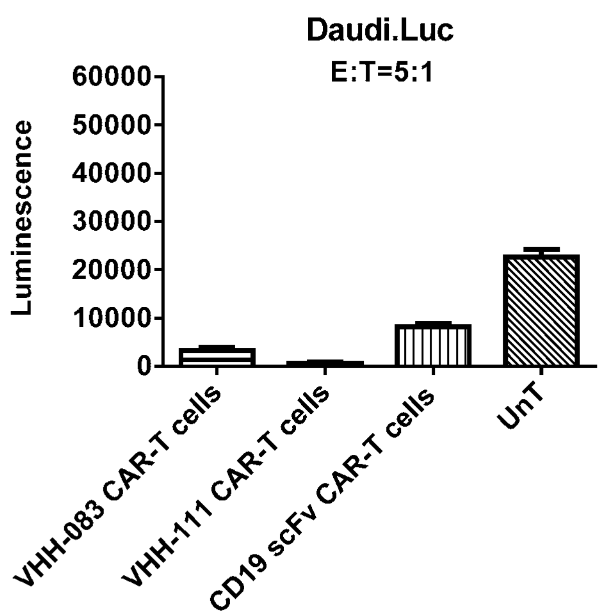
Figure 2C:
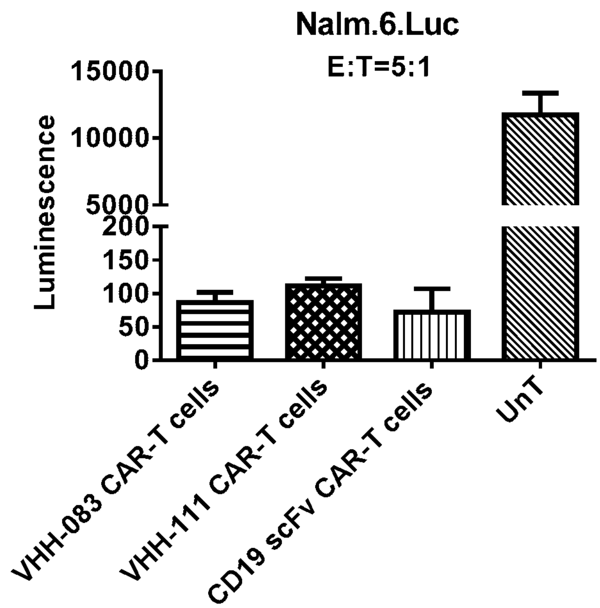
Figure 2D:
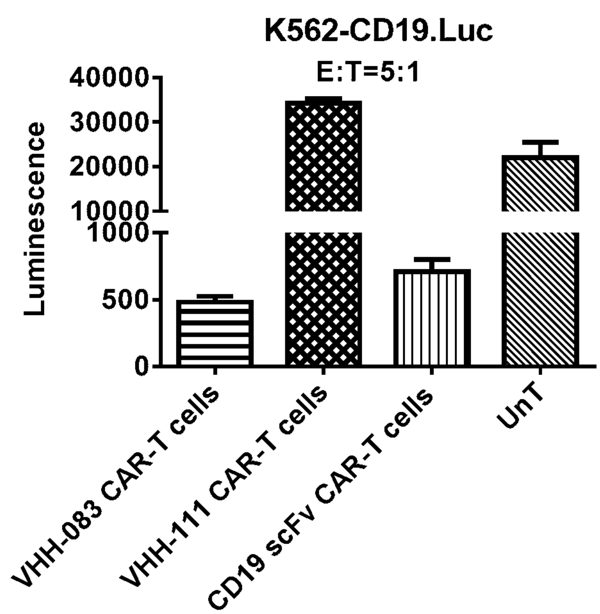
Figure 2E:
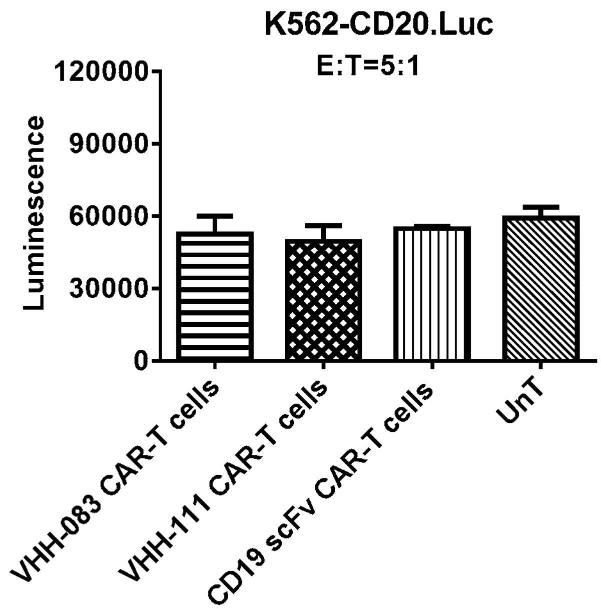
Figure 2F:
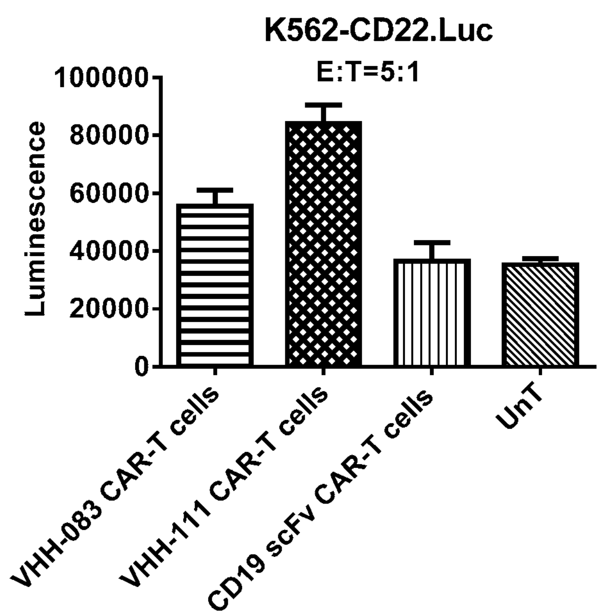
Figure 2G:
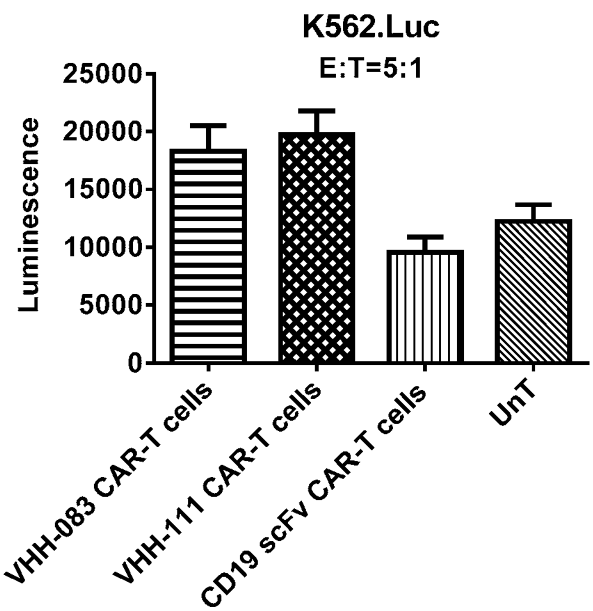
Figure 3A:
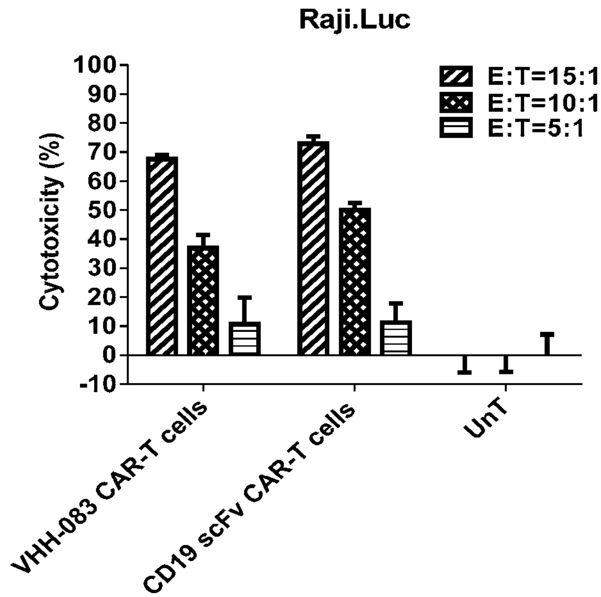
FIGS. 3A-3I show in vitro cytotoxicity of exemplary VHH-based CAR-T cells compared to that of scFv-based CAR-T cells against CD19 positive cell lines (FIGS. 3A-3D, 3F and 3G) or CD19 negative cell lines (FIGS. 3E, 3H and 3I).
Figure 3B:
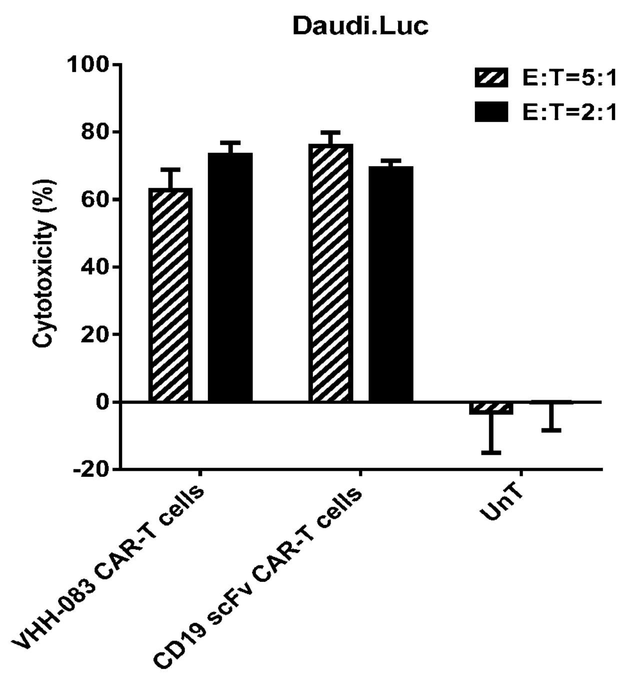
Figure 3C:
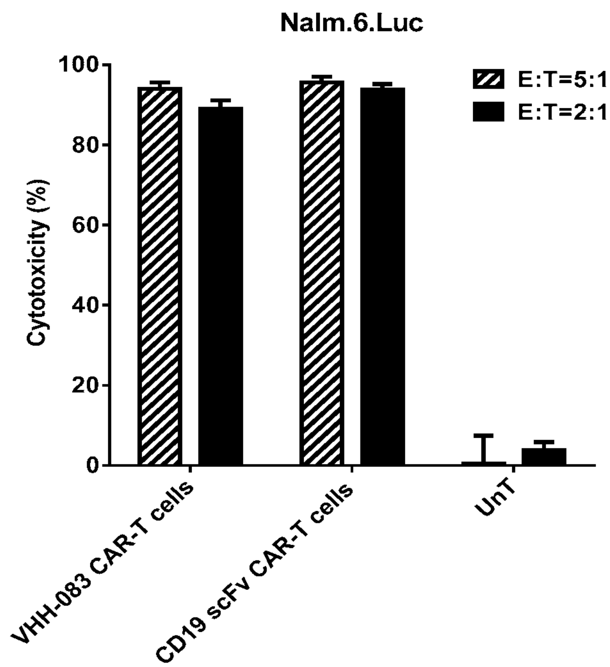
Figure 3D:
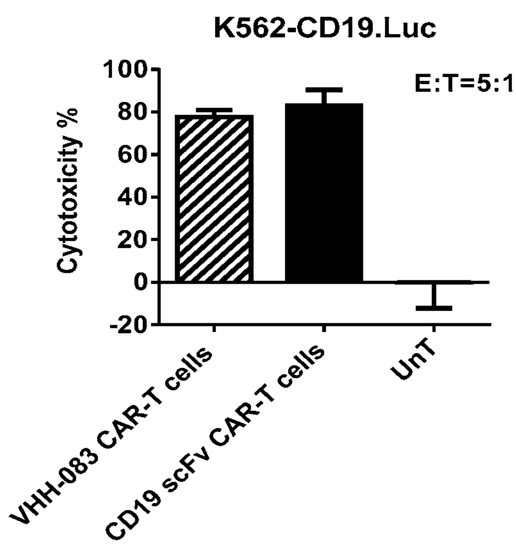
Figure 3E:
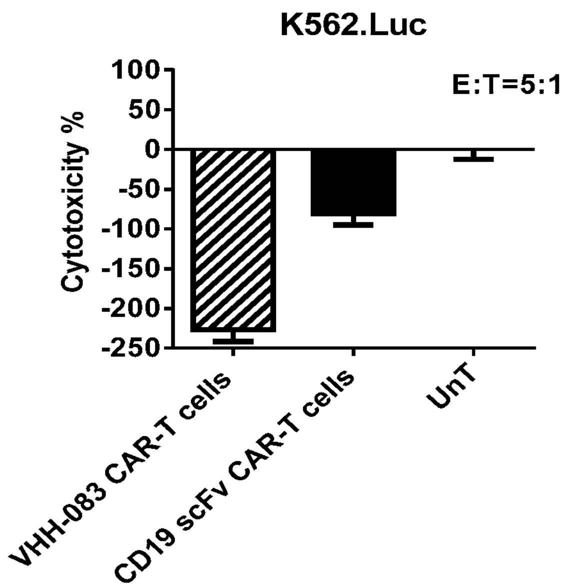
Figure 3F:
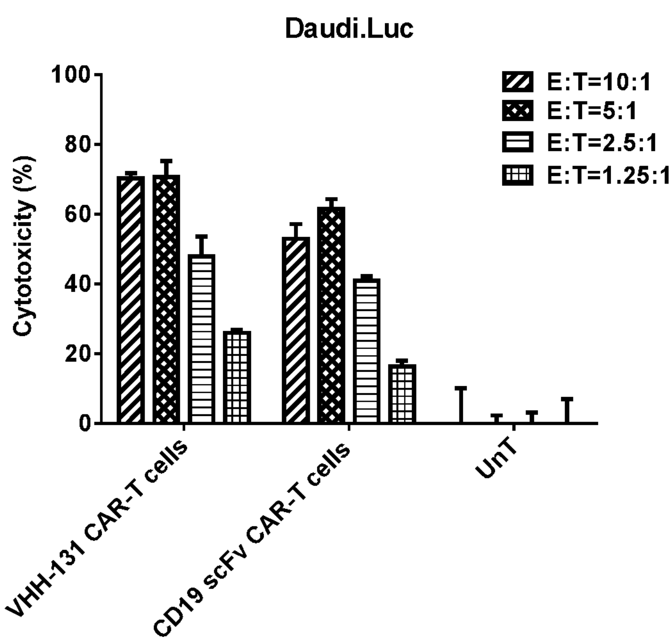
Figure 3G:
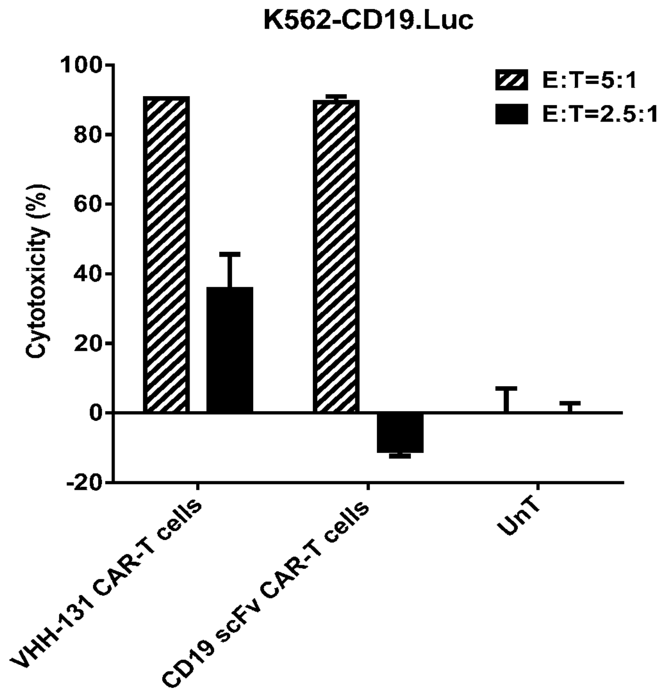
Figure 3H:
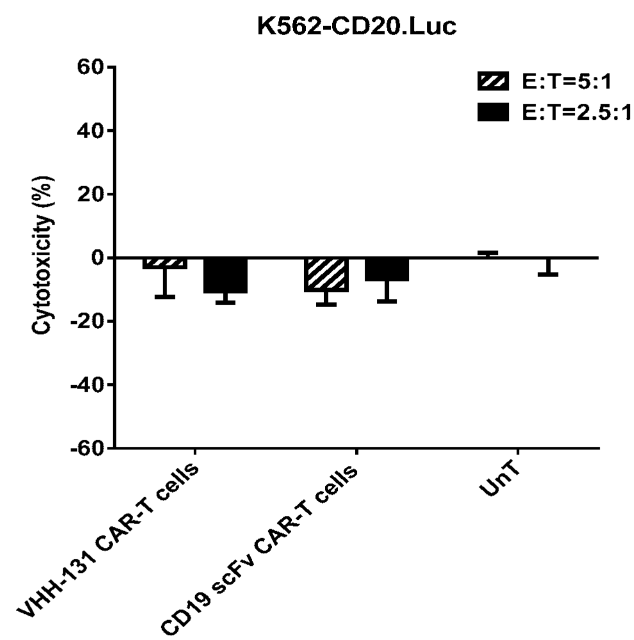
Figure 3I:
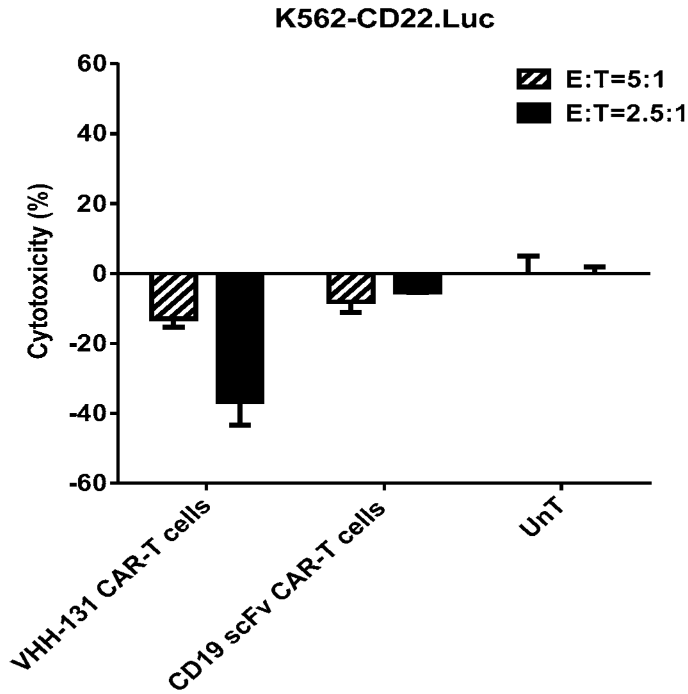

Nine days post transduction, CAR+ expression level (%) of the exemplary VHH-based CAR-T cells reached around 18%~27% (see FIG. 1). CD19 VHH CAR-T cells were expanded about 50-70 folds. The cell counts and viability (92%~98%) of the CD19 VHH CAR-T cell cultures indicated that there was no detectable negative effect of the VHH(s) on the T cells ability to proliferate and expand when compared to the un-transduced T cells (UnT), as shown in Table 6.

TABLE 6

Viability and Expansion of CD19 CAR-T Cells

| Exemplary CAR-T cell Code | CAR Positive Ratio (CAR+ %) | Cell Culture (Day 9) Viability (%) | Cell Culture (Day 9) Expansion Fold |
|---|---|---|---|
| VHH-083 CAR-T cells | 27.09 | 92 | 70 |
| VHH-111 CAR-T cells | 18.44 | 93.5 | 52 |
| CD19 scFv CAR-T cells | 15.55 | 97.7 | 62 |

6.3. Example 3-Characterization of Immune Cells Expressing CD19 Chimeric Receptor Polypeptides In Vitro 6.3.1. Expression of CD19, CD20 and CD22 Antigens on Cell Surface To evaluate the expression levels of CD19, CD20 and CD22 on the assessed target cell surface, $5\times10^5$ of cells per well were incubated with PE-labeled anti-CD19, anti-CD20 and anti-CD22 mAbs, respectively (BioLegend, Cat. #302208, #302306 & #302506, respectively), and assessed by flow cytometry with QUANTI-BRITE PE beads (BD Bioscience, Cat. #340495). The assays and data analysis were performed in accordance with the manufacturer's instructions. "Receptor Number per Cell" indicates the approximate absolute number of molecules per cell on each of the indicated cell lines and is shown in Table 7.

TABLE 7

CD19, CD20 and CD22 Receptor Number per Target Cell

| Cell line | CD19 receptor number per cell | CD20 receptor number per cell | CD22 receptor number per cell |
|---|---|---|---|
| K562.Luc | <10 | <10 | <50 |
| K562-CD19.Luc | 189789 | NA | NA |
| K562-CD20.Luc | <10 | 28303 | NA |
| K562-CD22.Luc | <10 | NA | 93339 |
| Raji.Luc | 77641 | 132614 | 34854 |
| Daudi.Luc | 49158 | 247729 | 39586 |
| Nalm.6.Luc | 32773 | <10 | 10441 |

6.3.2 Efficacy Evaluation of CD19 CAR-T Cells

To assess the cytotoxicity of CD19 VHH CAR-T cells against tumor cells, the cells generated as described above were counted and co-cultured with antigen specific cancer cells to read out the killing potency. The control CD19 scFv CAR-T cells were used in all assays to compare assay variation and/or act as an internal control. The un-transduced T cells (UnT) were used as the non-targeting T cells control. CAR-T cell killing assays were conducted towards CD19 positive cell lines—human lymphoma cell line Raji (ATCC #CCL-86), Daudi (ATCC #CCL-213), Nalm.6 (ATCC #CRL-3273) and K562-CD19 (over-expressing stably CD19 gene); and CD19 negative cell lines—K562-CD20 (over-expressing stably CD20 gene), K562-CD22 (over-expressing stably CD22 gene) and K562 (ATCC #CCL-243). All cell lines were engineered to express firefly luciferase as a reporter for cell viability/killing. The transduced cells were selected with puromycin and refreshed by the selection culture medium (Eagle's Minimum Essential Medium supplemented with 10% FBS and 2 μg/mL puromycin) in every 2-3 days. Post 3 rounds of selection, the selected cell clones were harvested and preserved for further use. The cytotoxicity of CD19 VHH CAR-T cells was measured at the effector to target cell ratios (E:T) of 15:1, 10:1, 5:1 or 2:1 for 24 hours. Assays were initiated by mixing the respective number of T cells with a constant number of target cells. The remaining luciferase activity per well was assessed by ONE-Glo luciferase assay (Promega, Cat. #E6110), to quantify the remaining viable target cells per well.

CD19 VHH CAR-T cells were constructed and screened by in vitro cytotoxicity assay. The results showed that CD19 VHH CAR-T cells exhibited different levels of cytotoxicity against Raji.Luc, Daudi.Luc, Nalm.6.Luc, and K562-CD19.Luc cells (see exemplary data as shown in FIGS. 2A-2D). No significant cytotoxicity effect was detected against negative cell lines by CD19 VHH CAR-T cells as compared to UnT control (see FIGS. 2E-2G and FIGS. 3E-3I).

One exemplary CD19 VHH CAR-T cells (VHH-083 CAR-T cells) were less potent than CD19 scFv CAR-T cells against Raji.Luc, and its potency was comparable to CD19 scFv CAR-T cells against Daudi.Luc, Nalm.6.Luc and K562-CD19 (see FIGS. 3A-3D). One exemplary CD19 VHH CAR-T cells (VHH-131 CAR-T cells) were more potent than CD19 scFv CAR-T cells against Daudi.Luc and K562-CD19.Luc (see FIGS. 3F-3G). All CD19 VHH CAR-T cells and CD19 scFv CAR-T cells showed dose-dependent killing to on-target cells (see FIGS. 3A and 3F).

The observation indicates that the CD19 VHH CARs provided herein induce T cell activation via specific recognizing CD19 expressing cells, activate T cell endogenous signaling pathway, induce activation of cytotoxic T lymphocytes (CTL) and enhance anti-tumor responses.

6.3.3. IFN-γ Release Evaluation of the CD19 CAR-T Cells

To measure cytokine production of CD19 VHH CAR-T cells in response to CD19-expressing cells, CAR-T cells were co-cultured with the CD19 positive cell lines—Raji.Luc, Daudi.Luc or Nalm.6.Luc, or the CD19 negative cell lines—K562-CD20.Luc or K562-CD22.Luc, at the E:T ratios of 15:1, 10:1, 5:1 or 2:1 for 24 hours, after which the media was harvested for the cytokine analysis using the human IFN-γ kit (Cisbio, Cat. #62HIFNGPEG) for cytokine quantification. The absorbance of each well (triplicate per teste article) was read by a multimode microplate reader (Tecan Spark).

Figure 4A:
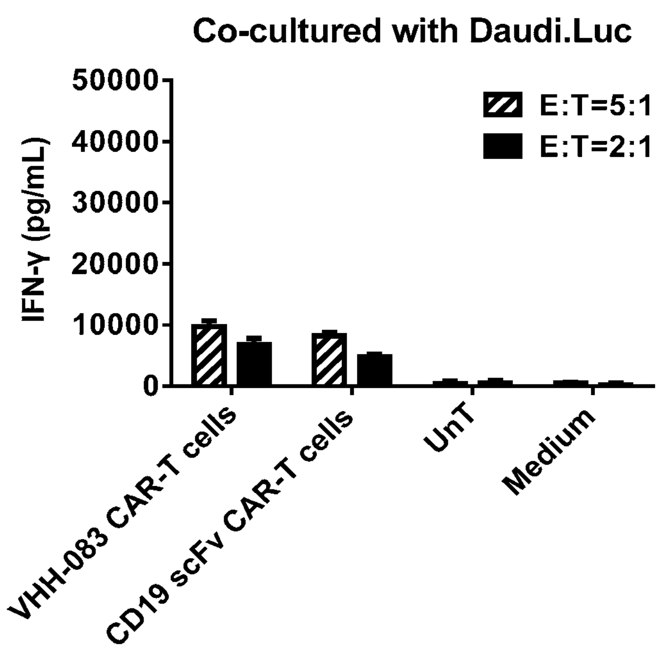
FIGS. 4A-4C show IFN-γ release level of exemplary VHH-based CAR-T cells compared to that of scFv-based CAR-T cells after co-culture with Daudi.Luc, Nalm.6.Luc, Raji.Luc, K562-CD20.Luc or K562-CD22.Luc cells at different E:T ratios for 24 hours.
Figure 4B:
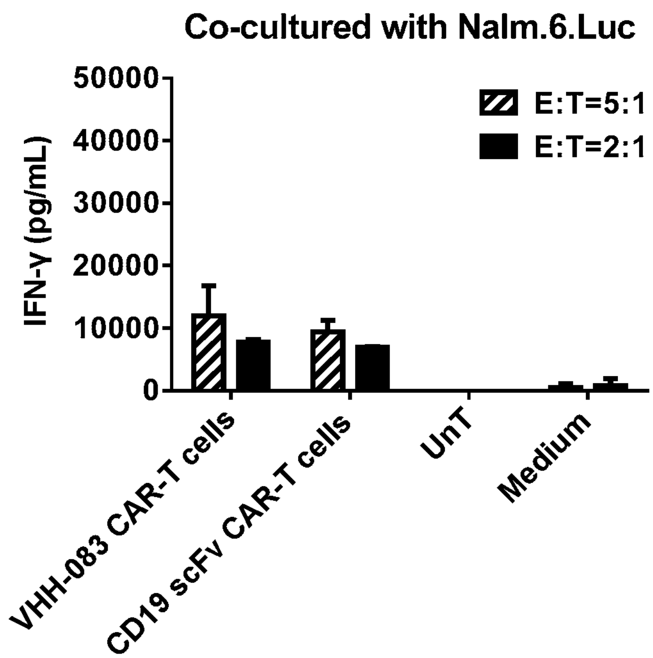
Figure 4C:
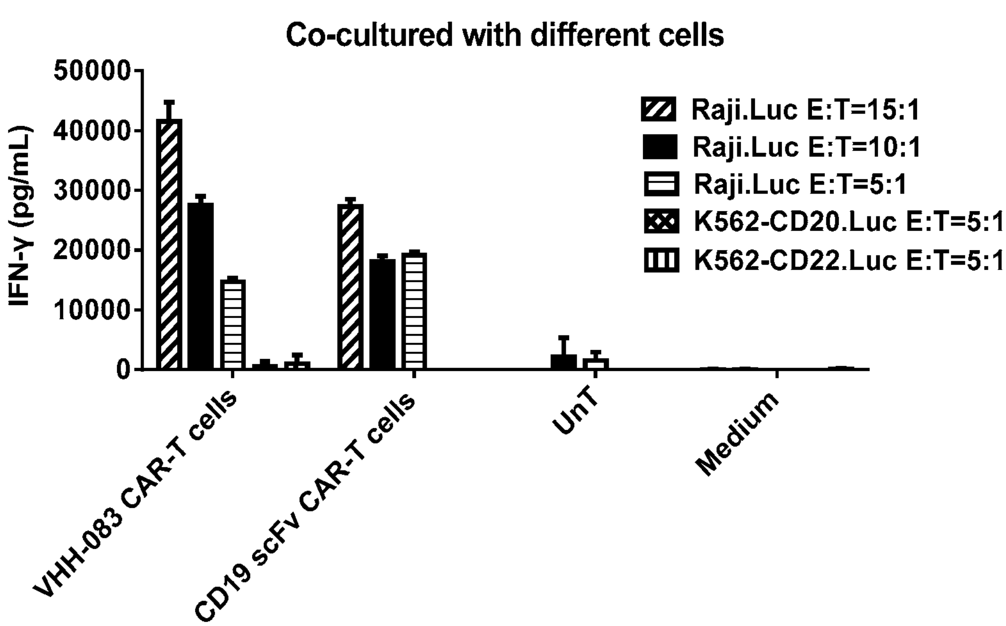

IFN-γ releasing data showed that the exemplary CD19 VHH CAR-T cells (VHH-083 CAR-T cells) produced much more IFN-γ than CD19 scFv CAR-T cells did when co-cultured with Raji.Luc (E:T=15:1 or 10:1) (see exemplary data as shown in FIG. 4C), and also produced more IFN-γ than CD19 scFv CAR-T cells did when co-cultured with Daudi.Luc and Nalm.6.Luc (see FIGS. 4A-4B). In contrast, IFN-γ release was not detectable or extremely low in cultures containing either un-transduced T cells or negative control cells K562-CD20.Luc and K562-CD22.Luc (see FIG. 4C), confirming that CD19-specificity of the CAR-T cells was required for reactivity to CD19 expressing cells.

6.4. Example 4—In Vivo Efficacy of the CD19 VHH CAR-T Cells in Tumor Xenograft Mice Anti-tumor activity of the generated CD19 VHH CAR-T cells was assessed in vivo in a Raji xenograft NCG mouse model, and CD19 scFv CAR-T cells and un-transduced cells (UnT) were evaluated as controls.

Celline: Raji (ATCC #CCL-86) is the lymphoblast-like cell line, established by Pulvertaft in 1963 from a Burkitt's lymphoma of the 11-year-old male. Raji cells were grown in RMPI medium containing 10% fetal bovine serum. This cell line grows in suspension in tissue culture flasks. This cell line persists and expands in mice when implanted intravenously. The Raji cells had been modified to express luciferase, so that tumor cell growth could also be monitored by imaging the mice. The Raji model endogenously expresses high levels of CD19, CD20 and CD22, and thus, can be used to test the in vivo efficacy of CD19-directed engineered T cells.

Mice: 5-6 weeks old NCG (NOD-Prkdcem26Cd52Il2rgem26Cd22/Nju) female mice were received from Model Animal Research Center of Nanjing University, with similar weight (around 20 g). Animals were allowed to acclimate in the animal facility for 7 days prior to experimentation. Animals were handled in accordance with ACUC regulations and guidelines.

6.4.1. In Vivo Test and Result of CD19 VHH CAR-T Cells Efficacy

To create the tumor xenograft, NCG Mice were injected intravenously with Raji.Luc. The mice were treated with the T cells 4 days post Raji.Luc tumor cell implantation. The mice were injected intravenously via the tail vein with 400 μL of the T cells for a dose of $1\times10^6$ T cells per mouse. The four mice in each group were treated with either CD19 VHH CAR-T cells, or CD19 scFv CAR-T cells, 400 μL of HBSS alone and un-transduced T cells (UnT) as controls. All the T cells were prepared from the same donor in parallel. Animal health status was monitored twice per week, including body weight measurement. Tumors growth was monitored weekly by bioluminescence imaging (BLI) until animals achieved endpoint.

Figure 5A:
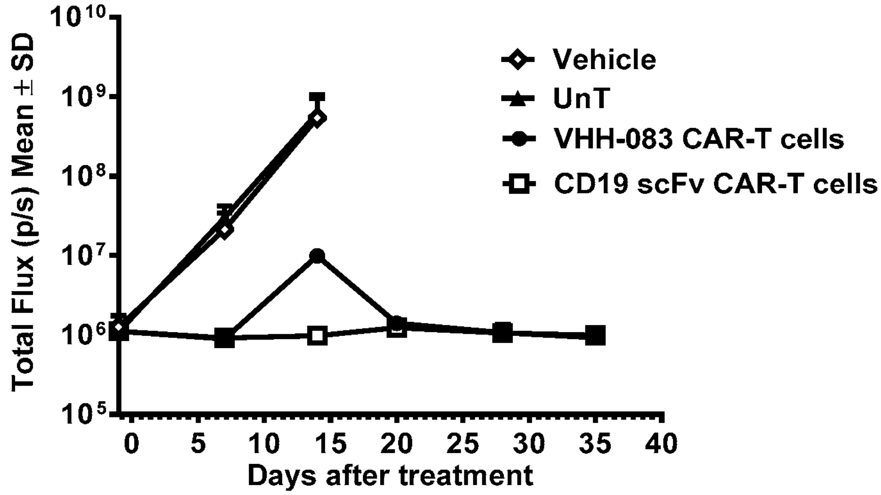
FIGS. 5A-5C show in vivo efficacy of exemplary VHH-based CAR-T cells in a Raji xenograft NCG mouse model. Mice were assessed on a regular basis to monitor tumor growth by bioluminescence imaging (FIGS. 5A-5B), and body weight (FIG. 5C).
Figure 5B:
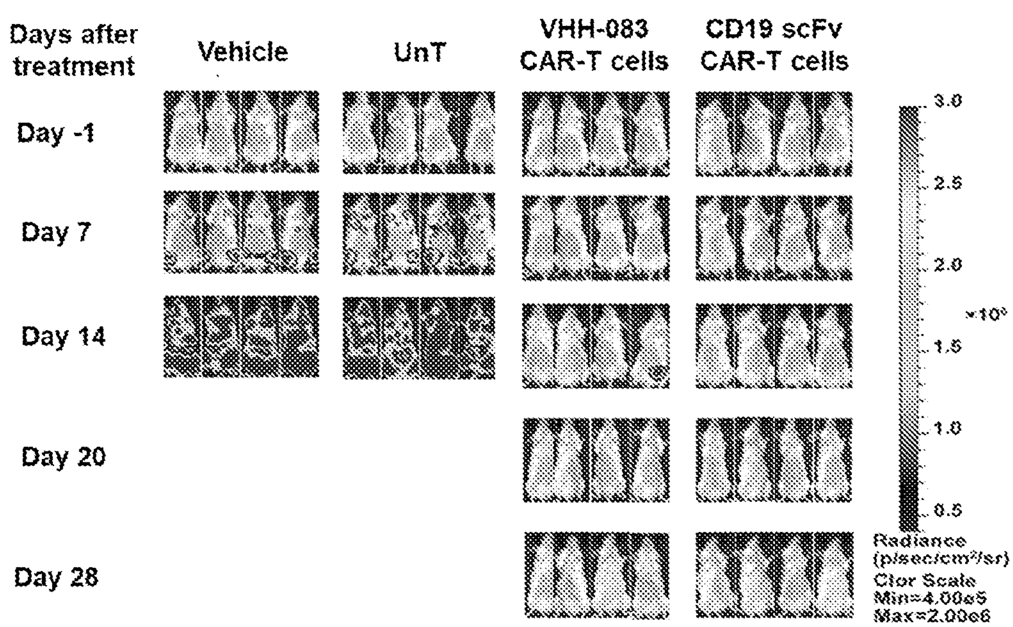
Figure 5C:
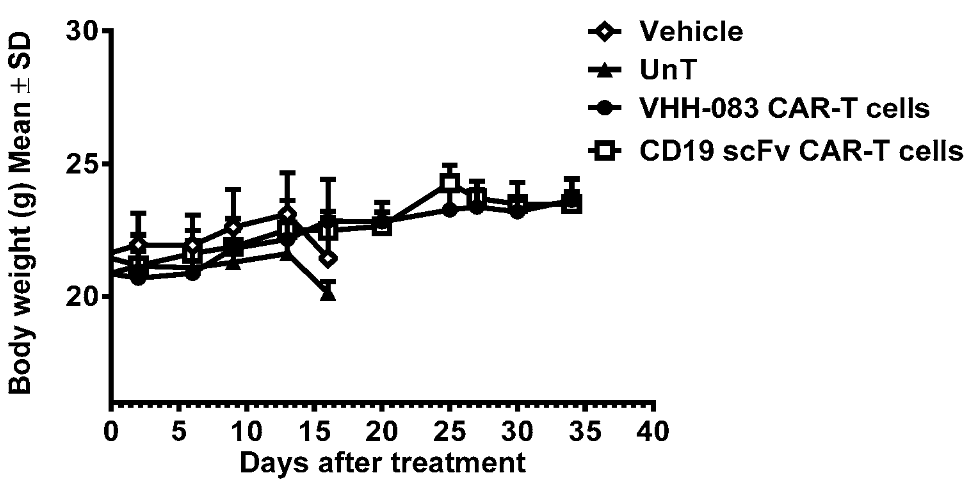

The HBSS treatment group (vehicle), which did not receive any T cells, demonstrated baseline Raji tumor growth kinetics in intravenously injected NCG mice. The UnT treatment group received non-transduced T cells as negative control for the engineered T cells. Both the HBSS and the UnT treatment groups demonstrated continuous aggressive tumor progression throughout this study and were euthanized on Day 16. VHH-083 CAR-T cells significantly inhibited tumor growth when compared to UnT treatment and showed complete tumor inhibition during the 35 days of the in vivo efficacy study, as indicated by the mean bioluminescence and the image of bioluminescence (see FIGS. 5A and 5B). In addition, the twice per week monitored mice health status was normal and the body weights were increased in CD19 VHH CAR-T cells treatment group throughout the 35 days of in vivo study (see FIG. 5C).

6.5. Example 5—Characterization of Anti-CD19 VHH-huIgG1Fc Monoclonal Antibody (mAb) Binding and On-/Off-Target Activity in Kro 6.5.1. Anti-CD19 VHH-huIgG1Fc mAb On-Target Binding to CD19 Receptor Positive Cells and $EC_{50}$ Anti-CD19 VHH sequences with human IgG1 Fc fragment sequence (SEQ ID NO: 77) were cloned into a mammalian expression vector—pcDNA3.4, to facilitate the recombinant protein expression. The DNA codons were further optimized for optimal expression in mammalian host cell—Expi293F. The antibodies were harvested from the supernatant of cell culture, one-step purified by MabSelect SuRe LX and sterilized via a 0.2 μm filter. The purified antibody concentrations were determined by A280 and reached 2-3 mg/mL with ~90% purity. Anti-CD19 Fab-huIgG1Fc mAb comprising amino acid sequences of FMC63 VH-CH1 and FMC63 VL-CL shown in SEQ ID NO: 101 and SEQ ID NO: 102 was used as a positive control for the cell surface binding assay. A CD19 positive cell line (Raji) and a negative cell line (K562) were re-suspended in complete culture medium, cells concentration was diluted to $1\times10^6$ cells/mL and the staining was performed in $2\times10^5$ cells per well. The mAbs were serially diluted from maximal concentration (3-fold reduction) and added according to the experimental plan and protocol. The mAbs and cells were co-incubated for 1 hour at 4° C. Then, the cells were washed with 200 μL of DPBS+0.5% FBS and spun at 300 g for 5 mins at 4° C. The cells were stained with the detection antibody—PE-conjugated mouse anti-human IgG1 Fc (BioLegend, Cat. #409304, 1:100) for 40 mins at 4° C. The cells were then washed again and re-suspended with 200 μL of DPBS+0.5% FBS for flow cytometric analysis on a NovoCyte Flow Cytometer (ACEA Biosciences). The FACS data was analyzed by Novoexpress software, and the MFI (median fluorescent intensity) was analyzed by GraphPad PRISM version 6.0.

Figure 6A:
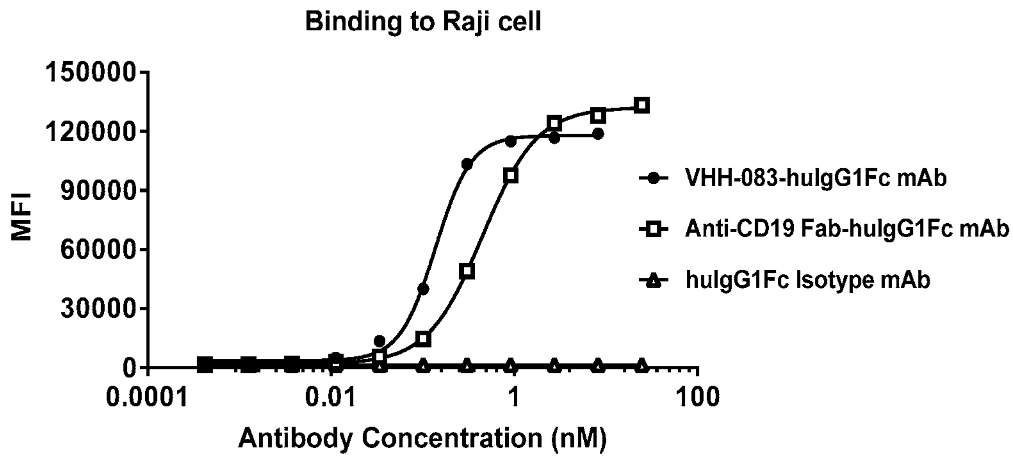
FIGS. 6A-6C show the exemplary results from studies assessing binding affinities of anti-CD19 VHH-huIgG1Fc mAbs. MFI=mean fluorescence intensity.
Figure 6B:
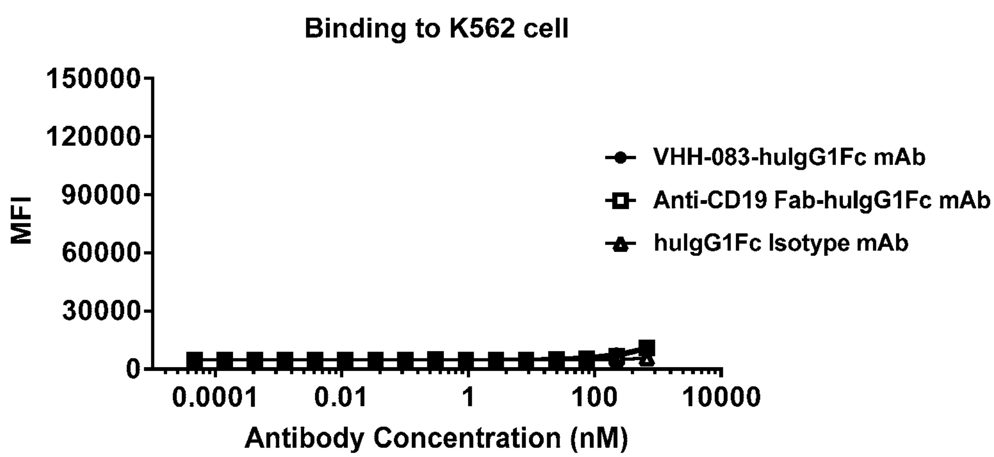
Figure 6C:
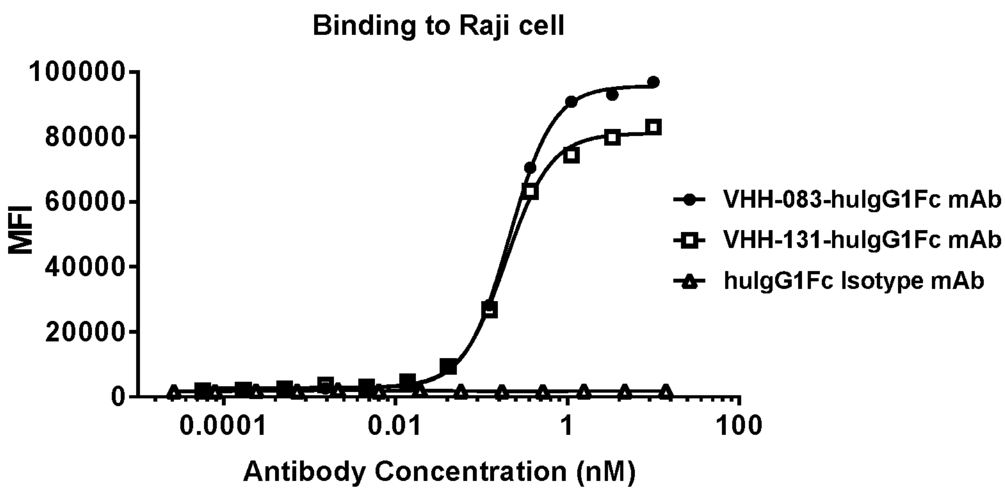

The cell surface binding data showed that exemplary anti-CD19 VHH-huIgG1Fc mAb (VHH-083-huIgG1Fc mAb and VHH-131-huIgG1Fc mAb) specifically bound to CD19 positive cells (i.e., Raji) in a dose-dependent manner, and VHH-083-huIgG1Fc mAb showed stronger binding than anti-CD19 Fab-huIgG1Fc mAb on target cells (see FIG. 6A). $EC_{50}$ of the VHH-083-huIgG1Fc mAb was 0.14 nM and $EC_{50}$ of the positive control—anti-CD19 Fab-huIgG1Fc mAb was 0.45 nM. VHH-083-huIgG1Fc mAb and anti-CD19 Fab-huIgG1Fc mAb showed no significant binding to negative cell line—K562 (see FIG. 6B). The VHH-131-huIgG1Fc mAb showed comparable binding to Raji as the VHH-083-huIgG1Fc mAb (see FIG. 6C). The term "EC50", also known as half maximal effective concentration, refers to the concentration of an antibody which induces a response halfway between the baseline and maximum after a specified exposure time.

6.5.2. Anti-CD19 VHH-huIgG1Fc mAb Off-Target Binding

To validate off-target binding, anti-CD19 VHH-huIgG1Fc mAbs were assessed with various human cell lines by using the method described above. The exemplary tested cell lines are listed in Table 8. The mAbs were incubated with $1\times10^5$ cells per well. For the tested VHH-083-huIgG1Fc mAb and VHH-131-huIgG1Fc mAb, non-specific binding to off-target cells was not observed at the concentration yielding maximum binding to Raji cells (Table 8).

TABLE 8

Anti-CD19 VHH-huIgG1Fc mAb Binding to Off-target Cells

| Cell Line | ATCC ID | Primary Site | CD19 expression level | VHH-083-huIgG1Fc mAb | VHH-131-huIgG1Fc mAb |
|---|---|---|---|---|---|
| Raji | CCL-86 | Lymphoid | + | + | + |
| Daudi | CCL-213 | Lymphoid | + | + | + |
| Nalm.6 | CRL-3273 | Lymphoid | + | + | + |
| RPMI-8226 | CCL-155 | Lymphoid | – | – | – |
| Jurkat | TIB-152 | Lymphoid | – | – | – |
| K562 | CCL-243 | Bone marrow | – | – | – |
| HL-60 | CCL-240 | Peripheral blood | – | – | – |
| THP-1 | TIB-85 | Peripheral blood | – | – | – |
| U87-MG | HTB-14 | Brain/Neuron | – | – | – |
| IMR-32 | CCL-127 | Brain/Neuron | – | – | – |
| FaDu | HTB-43 | Pharynx | – | – | – |
| A-253 | HTB-41 | Salivary gland | – | – | – |
| SK-BR-3 | HTB-30 | Breast | – | – | – |
| A549 | CCL-185 | Lung | – | – | – |
| NCI-H446 | HTB-171 | Lung | – | – | – |
| HepG2 | HB-8065 | Liver | – | – | – |
| NCI-N87 | CRL-5822 | Stomach | – | – | – |
| HEK-293T | 632180 | Kidney | – | – | – |
| PANC-1 | CRL-1469 | Pancreas | – | – | – |
| HCT 116 | CCL-247 | Colorectal | – | – | – |
| SK-OV-3 | HTB-77 | Ovary | – | – | – |
| Hela | CCL-2 | Cervix | – | – | – |
| BeWo | CCL-98 | Placenta | – | – | – |
| A375 | CRL-1619 | Skin | – | – | – |
| U-2 OS | HTB-96 | Bone | – | – | – |

6.5.3. Anti-CD19 VHH-huIgG1Fc mAb Epitope Dinning

To characterize the binding of anti-CD19 VHH to CD19 antigen, the exemplary anti-CD 19 VHH-huIgG1Fc mAb and anti-CD19 Fab-huIgG1Fc mAb were tested pairwise to assess whether they block each other's binding to a specific site of CD19 antigen. CD19 antigen was coated on the plate at a concentration of 0.5 μg/mL, 100 μL/well on a 96-well plate, with coating buffer of PBS (pH7.4). The competition mAbs were conjugated with biotin under optimal conditions and titrated to find the optimal concentration (best signal to noise ratio) for the mAbs competition test. The ELISA method was applied by following the standard protocol with the secondary antibody as streptavidin-HRP. The data showed that the exemplary VHH-083-huIgG1Fc mAb blocked anti-CD19 Fab-huIgG1Fc mAb's binding to the same epitope and the two mAbs were "binned" together (see exemplary data in Table 9).

TABLE 9

Anti-CD19 VHH-huIgG1Fc mAb Epitope Binning

| Competition mAb | OD450 Anti-CD19 VHH-huIgG1Fc mAb | OD450 Anti-CD19 Fab-huIgG1Fc mAb |
|---|---|---|
| N.A. | 1.242 | 1.310 |
| Anti-CD19 VHH-huIgG1Fc mAb | 0.372 | 0.249 |
| Anti-CD19 Fab-huIgG1Fc mAb | 0.694 | 0.178 |

6.6. Example 6—Generation and Characterization of Humanized CD19 VHH CARs 6.6.1. Humanization of Anti-CD19 VHH Antibodies To reduce the immunogenicity in human, camelid VHH antibodies were humanized, since much of the immune response occurs against the non-human antibody constant region. When different framework regions are combined with the camelid CDRS, chimeric human and camelid antibodies specific for the same antigen can elicit different effector functions, extending their therapeutic benefits. Mono-specific camelid VHHs were humanized by using sequence-based approaches and framework shuffling to most homologous human germline sequence or related scaffold. The non-compatibility of camelid CDRs being supported by non-native human framework scaffold and elimination of key conformational residues were resolved by in silico CDR-grafting, homology structural modeling (tertiary conformation & fold), sequence alignment, structure based-back mutation design and reintroduction of key conformational residues from camelid VHH antibody. The antibody humanization process may not only eliminate steric clashes but also restore function in relation to binding affinity to its antigen.

Universal humanized VHH framework h-NbBcII10FGLA (Protein Data Bank, PDB code: 3EAK) designed by Cécile Vincke et al. was adopted for humanization design based on sequence homology. The homologous modeling of camelid VHH was performed using the modeling software MODELLER. According to alignment with human germline gene, IGHV3-64*04 was chosen as one human acceptor for anti-CD19 VHH. Relative solvent accessibility of the amino acids was calculated according to the three-dimensional structure of the protein. If one of the amino acids of VHH was exposed to a solvent, it would be replaced with the original amino acid. The exemplary humanized VHH domains (i.e., huVHH-773, huVHH-776, A592H1, A592H2, A592H3, and A592H4) generated herein are shown in Table 2, and the corresponding sequences are provided in the Sequence Listing provided herein.

6.6.2. Characterization of Humanized CD19 VHH CAR-T Cells

Exemplary humanized CD19 VHH CARs (including huVHH-773 CAR and huVHH-776 CAR) were generated using the method described above. The amino acid sequence of huVHH-773 CAR is SEQ ID NO: 62. The amino acid sequence of huVHH-776 CAR is SEQ ID NO: 63. The nucleic acid sequence of huVHH-773 CAR is SEQ ID NO: 70. The nucleic acid sequence of huVHH-776 CAR is SEQ ID NO: 71.

The humanized CD19 VHH CAR-T cells were then generated by lentivirus transduction in human primary T cells and were assessed by in vitro efficacy study according to the standard method. The transduced T cells showed different CAR expression levels (%) with humanized CD19 VHH CAR. Exemplary humanized CD19 VHH CAR-T cells' viability was about 86%~-92%, CAR positive (CAR+) was about 14%~17% and the expansion folds were within 17-20 in a 7-day culture, indicating that there was no detectable negative effect of humanized VHH on the T cells' capability to proliferate and expand when compared to the un-transduced T cells (UnT).

Humanized CD19 VHH CAR-T cells generated as described above were counted and co-cultured with antigen specific cancer cell lines to assess the killing potency, parental camelid CD19 VHH CAR-T cells and CD19 scFv CAR-T cells were used as control and the un-transduced T cells (UnT) were used as non-targeting T cells control. Humanized CD19 VHH CAR-T cell killing assay was conducted towards CD19 positive cell lines—Raji (ATCC #CCL-86), Nalm.6 (ATCC #CRL-3273) and K562-CD19, and negative cell line—K562 (ATCC #CCL-243). All the cell lines were engineered in-house to express firefly luciferase as a reporter for cell viability/killing. The transduced cells were selected with puromycin and refreshed by the selection culture medium (Eagle's Minimum Essential Medium supplemented with 10% FBS and 2 μg/mL of puromycin) in every 2-3 days. Post three rounds of selections, the selected cell clones were harvested and preserved for further use. The cytotoxicity of humanized CD19 VHH CAR-T cells was measured at an effector cells to target cells ratio (E:T) of 20:1, 15:1, 10:1, 5:1 or 2.5:1 for 24 hours. Assays were initiated by mixing the respective number of T cells with a constant number of target cells. The remaining luciferase activity per well was assessed by ONE-Glo luciferase assay (Promega, Cat. #E6110), to quantify the remaining viable target cells per well.

Figure 7A:
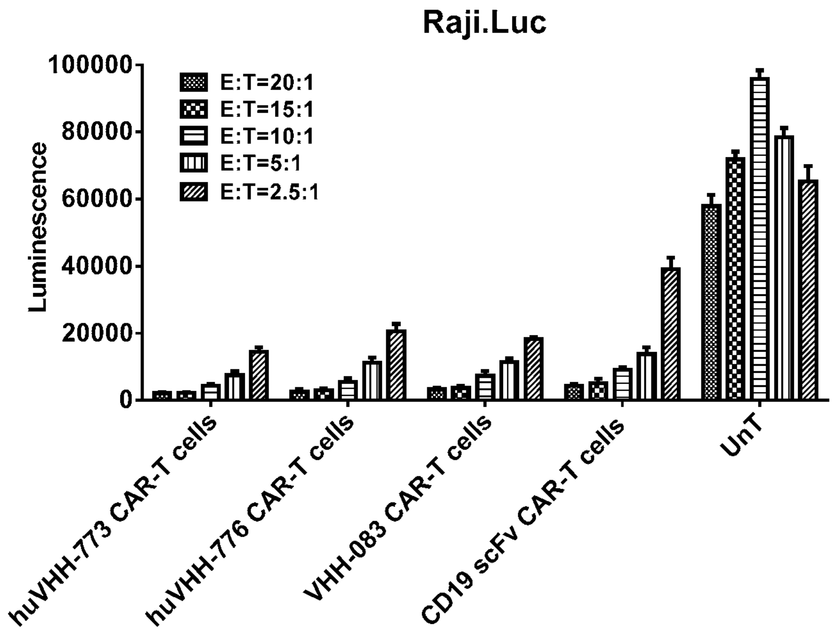
FIGS. 7A-7D show the cytotoxicity of the exemplary humanized CD19 VHH CAR-T cells on four cell lines at different effector cells to target cells ratios (E:T) of 20:1, 15:1, 10:1, 5:1 or 2.5:1.
Figure 7B:
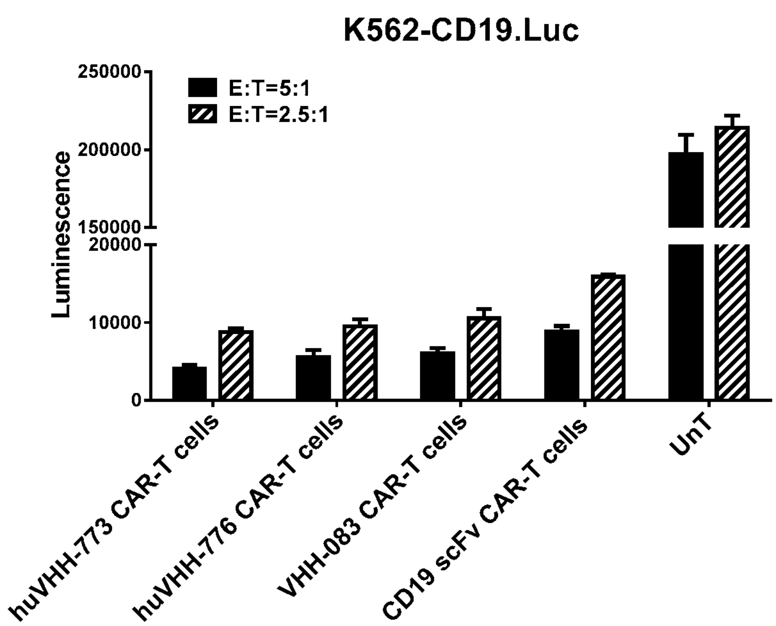
Figure 7C:
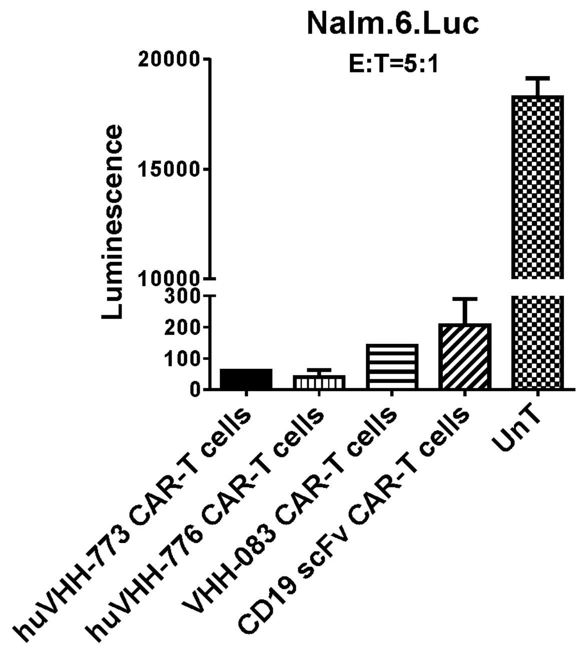
Figure 7D:
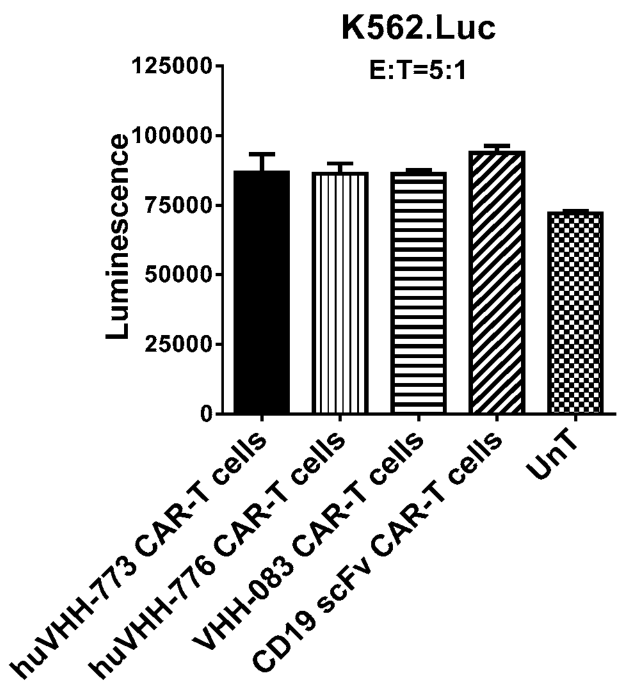

The data of the humanized CD19 VHH CAR-T cells (including huVHH-773 CAR-T cells and huVHH-776 CAR-T cells) showed that the CAR-T cells induced lysis of antigen specific target cells and exhibited higher potency or maintained potency against the target cells (see exemplary data as shown in FIGS. 7A-7C). No significant cytotoxicity effect was detected against negative cell line—K562.Luc by humanized CD19 VHH CAR-T cells as compared to UnT control (see FIG. 7D).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed:

1. An anti-CD19 single domain antibody (sdAb) comprising:

(i) a CDR1 comprising the amino acid sequence of SEQ ID NO: 1; a CDR2 comprising the amino acid sequence of SEQ ID NO: 8; and a CDR3 comprising the amino acid sequence of SEQ ID NO: 15;

(ii) a CDR1 comprising the amino acid sequence of SEQ ID NO: 22 or 108; a CDR2 comprising the amino acid sequence of SEQ ID NO: 29; and a CDR3 comprising the amino acid sequence of SEQ ID NO: 36;

(iii) a CDR1 comprising the amino acid sequence of SEQ ID NO: 2; a CDR2 comprising the amino acid sequence of SEQ ID NO: 9; and a CDR3 comprising the amino acid sequence of SEQ ID NO: 16;

(iv) a CDR1 comprising the amino acid sequence of SEQ ID NO: 23 or 109; a CDR2 comprising the amino acid sequence of SEQ ID NO: 30; and a CDR3 comprising the amino acid sequence of SEQ ID NO: 37;

(v) a CDR1 comprising the amino acid sequence of SEQ ID NO: 3; a CDR2 comprising the amino acid sequence of SEQ ID NO: 10; and a CDR3 comprising the amino acid sequence of SEQ ID NO: 17;

(vi) a CDR1 comprising the amino acid sequence of SEQ ID NO: 24 or 110; a CDR2 comprising the amino acid sequence of SEQ ID NO: 31; and a CDR3 comprising the amino acid sequence of SEQ ID NO: 38;

(vii) a CDR1 comprising the amino acid sequence of SEQ ID NO: 4; a CDR2 comprising the amino acid sequence of SEQ ID NO: 11; and a CDR3 comprising the amino acid sequence of SEQ ID NO: 18;

(viii) a CDR1 comprising the amino acid sequence of SEQ ID NO: 25 or 111; a CDR2 comprising the amino acid sequence of SEQ ID NO: 32; and a CDR3 comprising the amino acid sequence of SEQ ID NO: 39;

(ix) a CDR1 comprising the amino acid sequence of SEO ID NO: 5: a CDR2 comprising the amino acid sequence of SEQ ID NO: 12; and a CDR3 comprising the amino acid sequence of SEQ ID NO: 19;

(x) a CDR1 comprising the amino acid sequence of SEQ ID NO: 26 or 112; a CDR2 comprising the amino acid sequence of SEQ ID NO: 33; and a CDR3 comprising the amino acid sequence of SEQ ID NO: 40;

(xi) a CDR1 comprising the amino acid sequence of SEQ ID NO: 6; a CDR2 comprising the amino acid sequence of SEQ ID NO: 13; and a CDR3 comprising the amino acid sequence of SEQ ID NO: 20;

(xii) a CDR1 comprising the amino acid sequence of SEQ ID NO: 27 or 113; a CDR2 comprising the amino acid sequence of SEQ ID NO: 34; and a CDR3 comprising the amino acid sequence of SEQ ID NO: 41;

(xiii) a CDR1 comprising the amino acid sequence of SEQ ID NO: 7; a CDR2 comprising the amino acid sequence of SEQ ID NO: 14; and a CDR3 comprising the amino acid sequence of SEQ ID NO: 21;

(xiv) a CDR1 comprising the amino acid sequence of SEQ ID NO: 28 or 114; a CDR2 comprising the amino acid sequence of SEQ ID NO: 35; and a CDR3 comprising the amino acid sequence of SEQ ID NO: 42; or (xv) a CDR1 comprising the amino acid sequence of SEQ ID NO: 1; a CDR2 comprising the amino acid sequence of SEQ ID NO: 8; and a CDR3 comprising the amino acid sequence of SEQ ID NO: 50; or (xvi) a CDR1 comprising the amino acid sequence of SEQ ID NO: 22 or 108; a CDR2 comprising the amino acid sequence of SEQ ID NO: 103; and a CDR3 comprising the amino acid sequence of SEQ ID NO: 36.

2. The anti-CD19 sdAb of claim 1, further comprising one or more FR regions as set forth in SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, and/or SEQ ID NO: 104.

3. The anti-CD19 sdAb of claim 1, wherein anti-CD19 sdAb comprises or consists of an amino acid sequence having at least 75%, 80%, 85%, 90%, 95%, 96%, 97%, 98%, 99%, sequence identity with the sequence of SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, or SEQ ID NO: 104.

4. The anti-CD19 sdAb of claim 1, wherein anti-CD19 sdAb is a camelid sdAb or a humanized sdAb.

5. The anti-CD19 sdAb of claim 1, wherein the anti-CD19 sdAb is genetically fused or chemically conjugated to an agent.

6. A chimeric antigen receptor (CAR), comprising:

(a) an extracellular antigen binding domain comprising the anti-CD19 sdAb of claim 1;

(b) a transmembrane domain; and (c) an intracellular signaling domain.

7. The CAR of claim 6, further comprising a signal peptide located at the N-terminus of the polypeptide.

8. The CAR of claim 6, further comprising a hinge domain located between the C-terminus of the extracellular antigen binding domain and the N-terminus of the transmembrane domain.

9. The CAR of claim 6, wherein the extracellular antigen binding domain further comprises one or more additional antigen binding domain(s).

10. The CAR of claim 9, wherein the one or more additional antigen binding domain(s) bind to one or more antigen(s) selected from a group consisting of CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

11. An isolated nucleic acid comprising a nucleic acid sequence encoding the CAR of claim 6.

12. A vector comprising the isolated nucleic acid of claim 11.

13. An engineered immune effector cell, comprising the CAR of claim 6.

14. The engineered immune effector cell of claim 13, wherein the immune effector cell is a T cell or B cell.

15. A pharmaceutical composition, comprising the engineered immune effector cell of claim 13, and a pharmaceutically acceptable excipient.

16. A method of treating a disease or disorder in a subject, comprising administering to the subject an effective amount of the engineered immune effector cell of claim 13, wherein the disease or disorder is a B cell associated disease or disorder and/or CD19 associated disease or disorder.

17. The method of claim 16, wherein the disease or disorder is selected from a group consisting of marginal zone lymphoma, diffuse large B cell lymphoma (DLBCL), mantle cell lymphoma (MCL), primary central nervous system (CNS) lymphoma, primary mediastinal B cell lymphoma (PMBL), small lymphocytic lymphoma (SLL), B cell prolymphocytic leukemia (B-PLL), follicular lymphoma (FL), burkitt lymphoma, primary intraocular lymphoma, chronic lymphocytic leukemia (CLL), acute lymphoblastic leukemia (ALL), hairy cell leukemia (HCL), precursor B lymphoblastic leukemia, non-hodgkin lymphoma (NHL), high-grade B-cell lymphoma (HGBL), and multiple myelomia (MM).

18. An anti-CD19 single domain antibody (sdAb) comprising:

(i) a CDR1, a CDR2, and a CDR3 having the amino acid sequences of the CDR1, CDR2, and CDR3, respectively, as set forth in SEQ ID NO: 43;

(ii) a CDR1, a CDR2, and a CDR3 having the amino acid sequences of the CDR1, CDR2, and CDR3, respectively, as set forth in SEQ ID NO: 44;

(iii) a CDR1, a CDR2, and a CDR3 having the amino acid sequences of the CDR1, CDR2, and CDR3, respectively, as set forth in SEQ ID NO: 45;

(iv) a CDR1, a CDR2, and a CDR3 having the amino acid sequences of the CDR1, CDR2, and CDR3, respectively, as set forth in SEQ ID NO: 46;

(v) a CDR1, a CDR2, and a CDR3 having the amino acid sequences of the CDR1, CDR2, and CDR3, respectively, as set forth in SEQ ID NO: 47;

(vi) a CDR1, a CDR2, and a CDR3 having the amino acid sequences of the CDR1, CDR2, and CDR3, respectively, as set forth in SEQ ID NO: 48;

(vii) a CDR1, a CDR2, and a CDR3 having the amino acid sequences of the CDR1, CDR2, and CDR3, respectively, as set forth in SEQ ID NO: 49;

(viii) a CDR1, a CDR2, and a CDR3 having the amino acid sequences of the CDR1, CDR2, and CDR3, respectively, as set forth in SEQ ID NO: 51;

(ix) a CDR1, a CDR2, and a CDR3 having the amino acid sequences of the CDR1, CDR2, and CDR3, respectively, as set forth in SEQ ID NO: 52;

(x) a CDR1, a CDR2, and a CDR3 having the amino acid sequences of the CDR1, CDR2, and CDR3, respectively, as set forth in SEQ ID NO: 53;

(xi) a CDR1, a CDR2, and a CDR3 having the amino acid sequences of the CDR1, CDR2, and CDR3, respectively, as set forth in SEQ ID NO: 54;

(xii) a CDR1, a CDR2, and a CDR3 having the amino acid sequences of the CDR1, CDR2, and CDR3, respectively, as set forth in SEQ ID NO: 55;

(xiii) a CDR1, a CDR2, and a CDR3 having the amino acid sequences of the CDR1, CDR2, and CDR3, respectively, as set forth in SEQ ID NO: 56; or (xiv) a CDR1, a CDR2, and a CDR3 having the amino acid sequences of the CDR1, CDR2, and CDR3, respectively, as set forth in SEQ ID NO: 104.

19. The anti-CD19 sdAb of claim 18, wherein the CDR1, CDR2 or CDR3 are determined according to the Kabat numbering scheme, the IMGT numbering scheme, the AbM numbering scheme, the Chothia numbering scheme, the Contact numbering scheme, or a combination thereof.

20. A chimeric antigen receptor (CAR), comprising an amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, and SEQ ID NO: 105.

* * * * *